United States Patent
Nakayama et al.

(10) Patent No.: US 11,518,916 B2
(45) Date of Patent: Dec. 6, 2022

(54) LENS ADHESIVE, CEMENTED LENS, AND IMAGING MODULE

(71) Applicant: FUJIFILM Corporation, Tokyo (JP)

(72) Inventors: Takafumi Nakayama, Kanagawa (JP); Naozumi Shiraiwa, Kanagawa (JP); Naoyuki Morooka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 226 days.

(21) Appl. No.: 16/912,073

(22) Filed: Jun. 25, 2020

(65) Prior Publication Data

US 2020/0325367 A1     Oct. 15, 2020

Related U.S. Application Data

(63) Continuation of application No. PCT/JP2018/047423, filed on Dec. 25, 2018.

(30) Foreign Application Priority Data

Dec. 26, 2017   (JP) .............................. JP2017-249703
Jul. 2, 2018    (JP) .............................. JP2018-125970

(51) Int. Cl.
| | | |
|---|---|---|
| C09J 133/14 | (2006.01) | |
| C07D 277/82 | (2006.01) | |
| C07D 339/06 | (2006.01) | |
| C07D 417/04 | (2006.01) | |
| C08F 20/38 | (2006.01) | |
| G02B 3/00 | (2006.01) | |

(52) U.S. Cl.
CPC .......... *C09J 133/14* (2013.01); *C07D 277/82* (2013.01); *C07D 339/06* (2013.01); *C07D 417/04* (2013.01); *C08F 20/38* (2013.01); *G02B 3/00* (2013.01)

(58) Field of Classification Search
CPC .............................. C09J 133/14; C07D 277/82
See application file for complete search history.

(56) References Cited

U.S. PATENT DOCUMENTS

| | | | |
|---|---|---|---|
| 11,078,180 B2 * | 8/2021 | Morooka ............... | G02B 1/041 |
| 2010/0261018 A1 | 10/2010 | Turshani et al. | |
| 2011/0310721 A1 | 12/2011 | Arishima et al. | |
| 2013/0237630 A1 | 9/2013 | Morooka et al. | |
| 2015/0197592 A1 | 7/2015 | Someya et al. | |
| 2015/0277006 A1 | 10/2015 | Takasago et al. | |
| 2017/0342181 A1 | 11/2017 | Morooka | |
| 2018/0002276 A1 | 1/2018 | Kadomoto et al. | |
| 2018/0066189 A1 | 3/2018 | Ishii et al. | |
| 2018/0305486 A1 | 10/2018 | Nakayama et al. | |
| 2018/0362847 A1 | 12/2018 | Saito et al. | |
| 2020/0199095 A1 | 6/2020 | Morooka et al. | |

FOREIGN PATENT DOCUMENTS

| | | |
|---|---|---|
| EP | 0 131 468 A2 | 1/1985 |
| JP | S60-038411 A | 2/1985 |
| JP | H02-029401 A | 1/1990 |
| JP | H10-067977 A | 3/1998 |
| JP | 2002-047335 A | 2/2002 |
| JP | 2004-083855 A | 3/2004 |

(Continued)

OTHER PUBLICATIONS

Office Action dated Jul. 6, 2021 in Japanese Application No. 2019-561682.

(Continued)

*Primary Examiner* — Golam M Shameem
(74) *Attorney, Agent, or Firm* — Sughrue Mion, PLLC

(57) ABSTRACT

According to the present invention, a lens adhesive including a compound represented by General Formula 1 is provided.

$Pol_1-Sp_1-L_1-Ar-L_2-Sp_2-Pol_2$     (General Formula 1)

In the formula, Ar is an aromatic ring group represented by General Formula 2-2 and the like.

General Formula 2-2

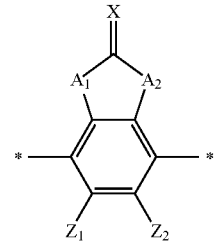

In the formula, $Z_1$ and $Z_2$ each represent a hydrogen atom, a methyl group, and the like; $A_1$ and $A_2$ each represent —S— and the like; X represents $C(Rz)_2$ and the like (where Rz is a substituent, and two Rz's may form a ring); $L_1$ and $L_2$ each represent a single bond, —O—, —OC(=O)—, —OC(=O)O—, —OC(=O)NH—, and the like; $Sp_1$ and $Sp_2$ each represent a single bond or a linking group such as a linear alkylene group; $Pol_1$ and $Pol_2$ each represent a hydrogen atom or a polymerizable group; and a compound represented by General Formula 1 has at least one polymerizable group. Using the lens adhesive, it is possible to provide a cemented lens that is unlikely to deteriorate due to light, and an imaging module having high durability.

6 Claims, 1 Drawing Sheet

(56) References Cited

FOREIGN PATENT DOCUMENTS

| | | |
|---|---|---|
| JP | 2005-325331 A | 11/2005 |
| JP | 2007-238883 A | 9/2007 |
| JP | 2008-107767 A | 5/2008 |
| JP | 2012-001498 A | 1/2012 |
| JP | 2012-021068 A | 2/2012 |
| JP | 2012-052016 A | 3/2012 |
| JP | 2012-107191 A | 6/2012 |
| JP | 2012-523485 A | 10/2012 |
| JP | 2013-071956 A | 4/2013 |
| JP | 2014-080572 A | 5/2014 |
| JP | 2016-053709 A | 4/2016 |
| JP | 2016-075911 A | 5/2016 |
| JP | 2016-081035 A | 5/2016 |
| WO | 2006/095610 A1 | 9/2006 |
| WO | 2013/018526 A1 | 2/2013 |
| WO | 2016/114211 A1 | 7/2016 |
| WO | 2016/114347 A1 | 7/2016 |
| WO | 2016/140245 A1 | 9/2016 |
| WO | 2017/043438 A1 | 3/2017 |
| WO | 2017/098988 A1 | 6/2017 |
| WO | 2017/115649 A1 | 7/2017 |
| WO | 2019/044863 A1 | 3/2019 |

OTHER PUBLICATIONS

Dumur et al., "Novel Fused D-A Dyad and A-D-A Triad Incorporating Tetrathiafulvalene and p-Benzoquinone", J. Org. Chem., vol. 69, No. 6, 2004, pp. 2164-2177.

Sun et al., "Benzoquinone derived I,3-dithiole-2-ones and thiones" Journal of Chemical Crystallography, vol. 27, No. 9, 1997, pp. 515-526.

International Search Report dated Mar. 12, 2019 from the International Searching Authority in International Application No. PCT/JP2018/047423.

International Preliminary Report on Patentability dated Jun. 30, 2020 from the International Bureau in International Application No. PCT/JP2018/047423.

Written Opinion dated Mar. 12, 2019 from the International Bureau in International Application No. PCT/JP2018/047423.

* cited by examiner

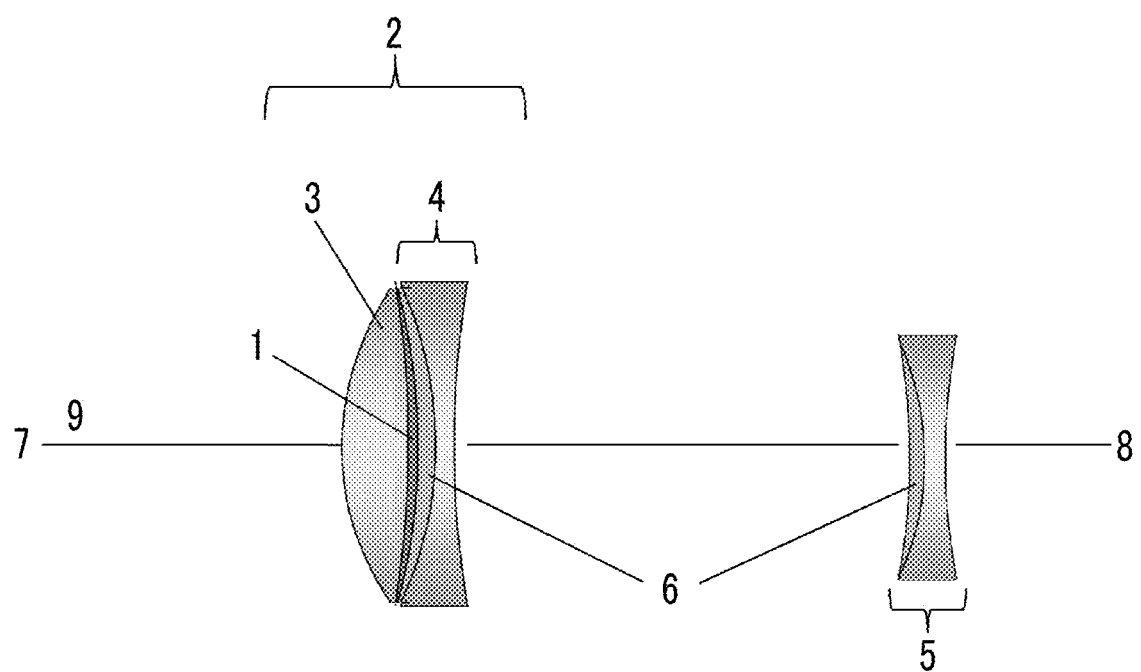

LENS ADHESIVE, CEMENTED LENS, AND IMAGING MODULE

CROSS-REFERENCE TO RELATED APPLICATIONS

This application is a continuation of PCT International Application No. PCT/JP2018/047423 filed on Dec. 25, 2018, which claims priorities under 35 U.S.C § 119 (a) to Japanese Patent Applications Nos. 2017-249703 and 2018-125970 filed on Dec. 26, 2017 and Jul. 2, 2018, respectively, and the entire contents of which are incorporated herein by reference.

BACKGROUND OF THE INVENTION

1. Field of the Invention

The present invention relates to a lens adhesive, a cemented lens, and an imaging module.

2. Description of the Related Art

In recent years, resin cured materials that can be mass-produced and have excellent workability have been used for optical lenses of imaging modules such as cameras, video cameras or camera-equipped mobile phones, videophones and camera-equipped door phones.

WO2017/115649A and JP2014-080572A disclose a compound having a diphenylfluorene skeleton or a skeleton similar thereto as a monomer used for forming the above-mentioned resin cured material. WO2017/115649A and JP2014-080572A report that a cured material having a small Abbe number can be molded using the above compound. By setting an Abbe number of a resin cured material forming an optical member to a small number, it is possible to correct chromatic aberration occurring in an optical lens used in an imaging module that requires miniaturization.

In addition, although it is possible to design optical lenses having various characteristics by cementing a plurality of single lenses, JP2012-523485A reports an adhesive having a high refractive index and a viscosity suitable for adhesion of a lens produced from a resin material.

Meanwhile, WO2016/114347A discloses a liquid crystal monomer having an aromatic ring group such as benzodithiol and benzothiazole.

SUMMARY OF THE INVENTION

Because a resin cured material deteriorates due to ultraviolet light, there is a problem of durability of an optical lens in an imaging module including an optical lens using the resin cured material. In particular, a resin cured material having a small Abbe number containing an aromatic-ring-containing compound as disclosed in WO2017/115649A or JP2014-080572A is likely to deteriorate due to light, because it absorbs light up to a long wavelength side (about 320 nm to 400 nm) in an ultraviolet light wavelength range. The inventors of the present invention have conceived of using an adhesive layer in a lens to reduce an influence of ultraviolet light on a resin cured material, but the adhesive disclosed in JP2012-523485A does not have a function of sufficiently inhibiting a deterioration due to light in a resin cured material.

An object of the present invention is to provide a lens adhesive capable of increasing durability of an optical lens. In particular, an object of the present invention is to provide a lens adhesive capable of increasing durability of an optical lens used in an imaging module.

The inventors of the present invention have paid attention to the compound disclosed in WO2016/114347A which absorbs ultraviolet light but still has excellent fastness with respect to ultraviolet irradiation, and have conceived of using, as an adhesive, a compound that has an aromatic ring group such as benzodithiol and benzothiazole but does not show a birefringent property as the compound disclosed in WO2016/114347A to produce an optical lens that is a cemented lens, and therefore have completed the present invention.

That is, the present invention provides the following <1> to <17>.

<1> A lens adhesive comprising a compound represented by General Formula 1.

$$Pol_1\text{-}Sp_1\text{-}L_1\text{-}Ar\text{-}L_2\text{-}Sp_2\text{-}Pol_2 \qquad \text{(General Formula 1)}$$

In General Formula 1, Ar is any of aromatic rings represented by General Formulas 2-1 to 2-4.

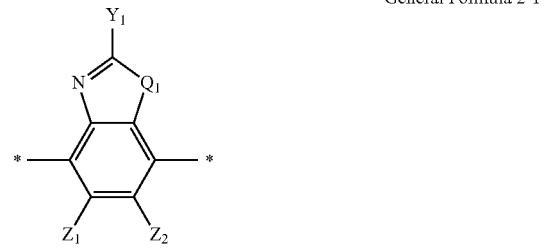

General Formula 2-1

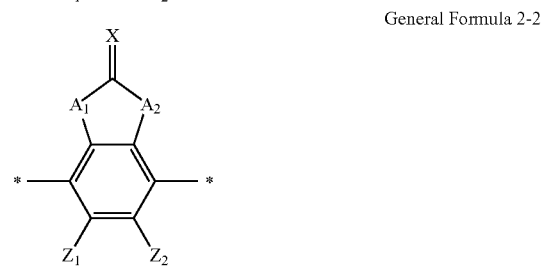

General Formula 2-2

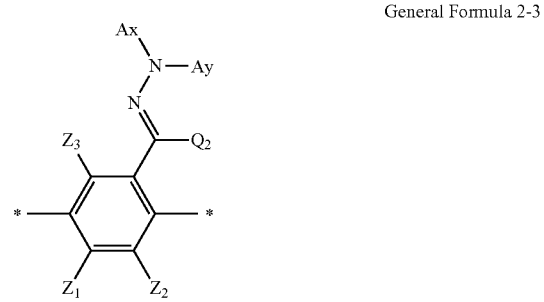

General Formula 2-3

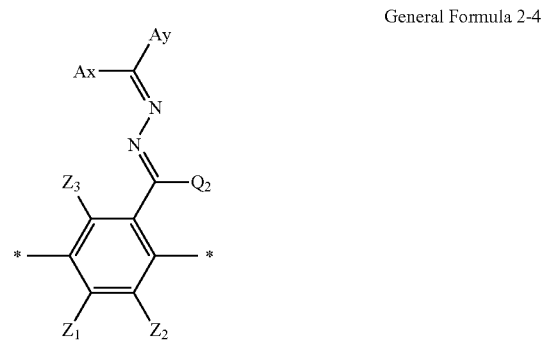

General Formula 2-4

In the formulas, $Q_1$ represents —S—, —O—, or $NR_{11}$—, where $R_{11}$ represents a hydrogen atom or an alkyl group having 1 to 6 carbon atoms, $Y_1$ represents an alkyl group which has 1 to 6 carbon atoms and may have a substituent; an aromatic hydrocarbon group which has 6 to 12 carbon atoms and may have a substituent; or an aromatic heterocyclic group which has 3 to 12 carbon atoms and may have a substituent, $Z_1$, $Z_2$, and $Z_3$ each independently represent a hydrogen atom, an aliphatic hydrocarbon group which has 1 to 20 carbon atoms and may have a substituent, an alkoxy group which has 1 to 20 carbon atoms and may have a substituent, an alicyclic hydrocarbon group which has 3 to 20 carbon atoms and may have a substituent, a monovalent aromatic hydrocarbon group which has 6 to 20 carbon atoms and may have a substituent, a halogen atom, a cyano group, a nitro group, $-NR_{12}R_{13}$, or $SR_{12}$, where $Z_1$ and $Z_2$ may be bonded to each other to form an aromatic hydrocarbon ring which may have a substituent or an aromatic heterocyclic ring which may have a substituent, and $R_{12}$ and $R_{13}$ each independently represent a hydrogen atom or an alkyl group having 1 to 6 carbon atoms, $A_1$ and $A_2$ each independently represent a group selected from the group consisting of —O—, $-NR_{21}$—, —S—, and CO—, where $R_{21}$ represents a hydrogen atom or a substituent, X represents O, S, C to which a hydrogen atom or a substituent is bonded, or N to which a hydrogen atom or a substituent is bonded, Ax represents an organic group which has 1 to 30 carbon atoms and has at least one aromatic ring selected from the group consisting of an aromatic hydrocarbon ring and an aromatic heterocyclic ring; and Ay represents a hydrogen atom, an alkyl group which has 1 to 6 carbon atoms and may have a substituent, or an organic group which has 1 to 30 carbon atoms and has at least one aromatic ring selected from the group consisting of an aromatic hydrocarbon ring and an aromatic heterocyclic ring, where the aromatic ring included in Ax and Ay may have a substituent, and Ax and Ay may be bonded to each other to form a ring which may have a substituent, $Q_2$ represents a hydrogen atom, or an alkyl group which has 1 to 6 carbon atoms and may have a substituent, $L_1$ and $L_2$ each independently represent a single bond, or a linking group selected from the group consisting of —O—, —S—, —C(=O)—, —OC(=O)—, —C(=O)O—, —OC(=O)O—, $-NR_{101}C(=O)$—, $-C(=O)NR_{102}$—, —OC(=O)$NR_{103}$—, $-NR_{104}C(=O)O$—, —SC(=O)—, and C(=O)S—, where $R_{101}$, $R_{102}$, $R_{103}$, and $R_{104}$ each independently represent -$Sp_3$-$Pol_3$ or a halogen atom, $Sp_1$ and $Sp_2$ each represent a single bond, or a linking group selected from the group consisting of a linear alkylene group which has 1 to 30 carbon atoms and may have a substituent, and a group in which one or two or more non-adjacent —$CH_2$—'s are substituted by —O—, —S—, —C(=O)—, —OC(=O)—, —C(=O)O—, —OC(=O)O—, —$NR_{201}$C(=O)—, —C(=O)$NR_{202}$—, —OC(=O)$NR_{203}$—, —$NR_{204}$C(=O)O—, —SC(=O)—, or —C(=O)S— in a linear alkylene group which has 1 to 30 carbon atoms and may have a substituent, where $R_{201}$, $R_{202}$, $R_{203}$, and $R_{204}$ each independently represent -$Sp_4$-$Pol_4$ or a halogen atom, $Sp_3$ and $Sp_4$ each independently represent a single bond or a divalent linking group, and $Pol_1$, $Pol_2$, $Pol_3$, and $Pol_4$ each independently represent a hydrogen atom or a polymerizable group, and in which the compound represented by General Formula 1 has at least one polymerizable group.

<2> The lens adhesive according to <1>, in which Ar is an aromatic ring represented by General Formula 2-2.

<3> The lens adhesive according to <1>, in which any of $L_1$ or $L_2$ is —O—, —OC(=O)—, —OC(=O)O—, or O—C(=O)NH—.

<4> The lens adhesive according to <1> or <2>, in which any of $L_1$ or $L_2$ is —O—; and any of $Sp_1$ or $Sp_2$ is a linking group selected from the group consisting of a linear alkylene group which has 1 to 30 carbon atoms and may have a substituent, and a group in which one or two or more non-adjacent —$CH_2$—'s are substituted by —O—, —S—, —C(=O)—, —OC(=O)—, —C(=O)O—, —OC(=O)O—, —$NR_{201}$C(=O)—, —C(=O)$NR_{202}$—, —OC(=O)$NR_{203}$—, —$NR_{204}$C(=O)O—, —SC(=O)—, or —C(=O)S— in a linear alkylene group which has 2 to 30 carbon atoms and may have a substituent and in which a terminal on an $L_1$ side or an $L_2$ side is —$CH_2$—.

<5> The lens adhesive according to any one of <1> to <4>, in which any of $Pol_1$ or $Pol_2$ is a (meth)acryloyloxy group.

<6> The lens adhesive according to any one of <1> to <5>, in which the lens adhesive includes a polymer having an ethylenically unsaturated group.

<7> A cemented lens consisting of: a lens A; an adhesive layer; and a lens B in this order, in which the adhesive layer is a layer obtained by curing the lens adhesive according to any one of <1> to <6>.

<8> The cemented lens according to <7>, in which the lens A is a glass lens, and the lens B is a resin lens or a compound lens having a resin layer on a surface thereof.

<9> The cemented lens according to <8>, in which an Abbe number of the resin lens or a resin cured material forming the resin layer in the lens B is 30 or less.

<10> The cemented lens according to <8>, in which the resin lens or a resin cured material forming the resin layer in the lens B is a cured material of a composition containing a compound represented by General Formula (A).

General Formula (A)

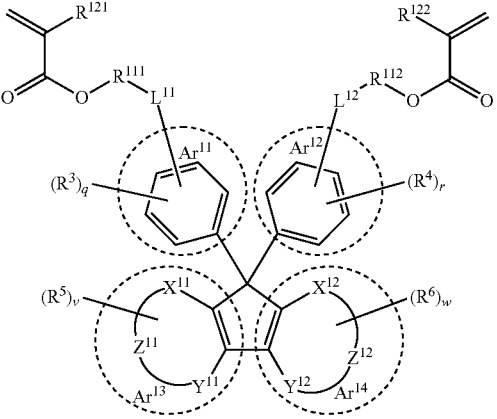

In General Formula (A), $Ar^{11}$ and $Ar^{12}$ each independently represent an aryl group containing a benzene ring surrounded by a broken line or a heteroaryl group containing a benzene ring surrounded by a broken line as one of rings constituting a fused ring, $X^{11}$, $Y^{11}$, $X^{12}$, and $Y^{12}$ each independently represent an oxygen atom, a sulfur atom, a nitrogen atom, or a carbon atom; $Z^{11}$ represents an atomic group which forms a 5- to 7-membered aromatic ring together with $X^{11}$—C=C—$Y^{11}$, and which contains at least one selected from an oxygen atom, a sulfur atom, a nitrogen atom, or a carbon atom; and $Z^{12}$ represents an atomic group which forms a 5- to 7-membered aromatic ring together with $X^{12}$—C=C—$Y^{12}$, and which contains at least one selected from an oxygen atom, a sulfur atom, a nitrogen atom, or a carbon atom, $Ar^{13}$ and $Ar^{14}$ each independently represent an arylene group containing an aromatic ring surrounded by a broken line or a heteroarylene group containing an aromatic ring surrounded by a broken line, where at least one of $Ar^{13}$ or $Ar^{14}$ is a group other than a phenylene group, $R^3$ to $R^6$ each independently represent a substituent; q and r each independently are an integer of 0 to 4; v is an integer of 0 or more, where a maximum number of v is a maximum number of substituents capable of being substituted on the ring formed by $X^{11}$—C=C—$Y^{11}$ and $Z^{11}$; and w is an integer of 0 or more, where a maximum number of w is a maximum number of substituents capable of being substituted on the ring formed by $X^{12}$—C=C—$Y^{12}$ and $Z^{12}$, $L^{11}$ and $L^{12}$ each independently represent a single bond, an oxygen atom, a sulfur atom, or an ester bond, $R^{111}$ and $R^{112}$ each independently represent a single bond or a divalent linking group, $R^{121}$ and $R^{122}$ each independently represent a hydrogen atom or a methyl group, and in a case where $Ar^{11}$ to $Ar^{14}$ each independently are a fused ring group containing an aromatic ring surrounded by a broken line as one of rings constituting a fused ring, a group having $L^{11}$ as a linking group, a group having $L^{12}$ as a linking group, and $R^3$ to $R^6$ each independently may be substituted on an aromatic ring surrounded by a broken line, or may be substituted on a ring constituting the fused ring other than the aromatic ring surrounded by the broken line.

<11> The cemented lens according to any one of <8> to <10>, in which the lens B is the compound lens, and the resin layer is in contact with the adhesive layer.

<12> An imaging module that images an object with a lens optical system to form an image, in which the lens optical system includes the cemented lens according to any one of <7> to <11>, and a lens A, an adhesive layer, and a lens B are disposed in this order from a side of the object toward a surface on which the image is formed.

<13> The imaging module according to <12>, in which the lens optical system includes a lens C, the lens C is a resin lens or a compound lens having a resin layer, and the lens C is disposed between the lens B and the surface on which the image is formed.

<14> The imaging module according to <13>, in which an Abbe number of the resin lens or a resin cured material forming the resin layer in the lens C is 30 or less.

<15> The imaging module according to <13>, in which the resin lens or a resin cured material forming the resin layer in the lens C is a cured material of a composition containing a compound represented by General Formula (A).

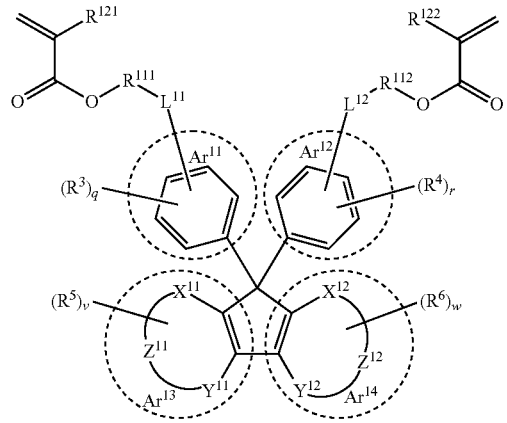

General Formula (A)

In General Formula (A), $Ar^{11}$ and $Ar^{12}$ each independently represent an aryl group containing a benzene ring surrounded by a broken line or a heteroaryl group containing a benzene ring surrounded by a broken line as one of rings constituting a fused ring, $X^{11}$, $Y^{11}$, $X^{12}$, and $Y^{12}$ each independently represent an oxygen atom, a sulfur atom, a nitrogen atom, or a carbon atom; $Z^{11}$ represents an atomic group which forms a 5- to 7-membered aromatic ring together with $X^{11}$—C=C—$Y^{11}$, and which contains at least one selected from an oxygen atom, a sulfur atom, a nitrogen atom, or a carbon atom; and $Z^{12}$ represents an atomic group which forms a 5- to 7-membered aromatic ring together with $X^{12}$—C=C—$Y^{12}$, and which contains at least one selected from an oxygen atom, a sulfur atom, a nitrogen atom, or a carbon atom, $Ar^{13}$ and $Ar^{14}$ each independently represent an arylene group containing an aromatic ring surrounded by a broken line or a heteroarylene group containing an aromatic ring surrounded by a broken line, where at least one of $Ar^{13}$ or $Ar^{14}$ is a group other than a phenylene group, $R^3$ to $R^6$ each independently represent a substituent; q and r each independently are an integer of 0 to 4; v is an integer of 0 or more, where a maximum number of v is a maximum number of substituents capable of being substituted on the ring formed by $X^{11}$—C=C—$Y^{11}$ and $Z^{11}$; and w is an integer of 0 or more, where a maximum number of w is a maximum number of substituents capable of being substituted on the ring formed by $X^{12}$—C=C—$Y^{12}$ and $Z^{12}$, $L^{11}$ and $L^{12}$ each independently represent a single bond, an oxygen atom, a sulfur atom, or an ester bond, $R^{111}$ and $R^{112}$ each independently represent a single bond or a divalent linking group, $R^{121}$ and $R^{122}$ each independently represent a hydrogen atom or a methyl group, and in a case where $Ar^{11}$ to $Ar^{14}$ each independently are a fused ring group containing an aromatic ring surrounded by a broken line as one of rings constituting a fused ring, a group having $L^{11}$ as a linking group, a group having $L^{12}$ as a linking group, and $R^3$ to $R^6$ each independently may be substituted on an aromatic ring surrounded by a broken line, or may be substituted on a ring constituting the fused ring other than the aromatic ring surrounded by the broken line.

<16> Application of a compound represented by General Formula 1 to a lens adhesive.

<17> Use of a compound represented by General Formula 1 to produce a lens adhesive.

According to the present invention, a lens adhesive is provided. The lens adhesive of the present invention absorbs ultraviolet light and has excellent fastness with respect to ultraviolet irradiation. By using the lens adhesive of the present invention, it is possible to improve durability of an optical lens used in an imaging module or the like, that is, durability of, particularly, an optical lens containing a resin cured material. By using the lens adhesive of the present invention, it is possible to provide a cemented lens that is unlikely to deteriorate due to light even in a case of being used in an imaging module or the like. In addition, by using the lens adhesive of the present invention, it is possible to provide an imaging module having high durability.

BRIEF DESCRIPTION OF THE DRAWINGS

FIG. 1 is a diagram showing an example of a lens optical system including an adhesive layer formed from a lens adhesive of the present invention.

DESCRIPTION OF THE PREFERRED EMBODIMENTS

Hereinafter, the present invention will be described in detail. The description of constituent elements described below can be made based on representative embodiments and specific examples, but the present invention is not limited to such embodiments. Numerical ranges expressed using "to" in the present specification mean a range including numerical values described before and after "to" as the lower limit and the upper limit.

In the present specification, "(meth)acrylate" refers to any one or both of acrylate and methacrylate, and "(meth)acryloyl" refers to any one or both of acryloyl and methacryloyl. The monomer in the present invention is a compound distinguished from oligomers and polymers and having a weight-average molecular weight of 1,000 or less.

In the present specification, in a case where an aliphatic hydrocarbon group is referred to, it represents a group obtained by removing one hydrogen atom from a linear or branched alkane, a linear or branched alkene, or a linear or branched alkyne. In the present specification, the aliphatic hydrocarbon group is preferably an alkyl group obtained by removing any one of hydrogen atoms from a linear or branched alkane.

In the present specification, in a case where an alkyl group is referred to, it represents a linear or branched alkyl group. Examples of alkyl groups include a methyl group, an ethyl group, a propyl group, an isopropyl group, a butyl group, an isobutyl group, a sec-butyl group, a tert-butyl group, a pentyl group, a 1-methylbutyl group, a 3-methylbutyl group, a hexyl group, a 1-methylpentyl group, a 4-methylpentyl group, a heptyl group, a 1-methylhexyl group, a 5-methylhexyl group, an octyl group, a 1-methylheptyl group, a nonyl group, a 1-methyloctyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, and the like. The same applies to an alkyl group in groups (for example, an alkoxy group, an alkoxycarbonyl group, an acyl group, and the like) containing an alkyl group.

In addition, in the present specification, examples of linear alkylene groups include groups obtained by removing each hydrogen atom bonded to a terminal carbon from a linear alkyl group among the above-mentioned alkyl groups.

In the present specification, examples of alicyclic hydrocarbon rings include cyclopropane, cyclobutane, cyclopentane, cyclohexane, cycloheptane, cyclooctane, cyclononane, and cyclodecane.

In the present specification, examples of unsaturated hydrocarbon rings include indene, indane, and fluorene.

In the present specification, in a case where an alicyclic hydrocarbon group is referred to, it represents a cycloalkyl group obtained by removing any one of hydrogen atoms from cycloalkane. Examples of alicyclic hydrocarbon groups include a cyclopropyl group, a cyclobutyl group, a cyclopentyl group, a cyclohexyl group, a cycloheptyl group, a cyclooctyl group, a cyclononyl group, a cyclodecyl group, and the like, where a cycloalkyl group having 3 to 12 carbon atoms is preferable.

In the present specification, a cycloalkylene group represents a divalent group obtained by removing any two hydrogen atoms from cycloalkane. Examples of cycloalkylene groups include a cyclohexylene group.

In the present specification, in a case where an aromatic ring is referred to, it means any one or both of an aromatic hydrocarbon ring and an aromatic heterocyclic ring.

In the present specification, examples of aromatic hydrocarbon ring include benzene, biphenyl, biphenylene, naphthalene, anthracene, and phenanthrene.

In the present specification, in a case where an aromatic hydrocarbon group is referred to, it represents a monovalent group obtained by removing any one of hydrogen atoms from an aromatic hydrocarbon ring. Examples thereof include a phenyl group, a biphenyl group, a 1-naphthyl group, a 2-naphthyl group, a 1-anthracenyl group, a 2-anthracenyl group, a 3-anthracenyl group, a 4-anthracenyl group, a 9-anthracenyl group, a 1-phenanthryl group, a 2-phenanthryl group, a 3-phenanthryl group, a 4-phenanthryl group, a 9-phenanthryl group, and the like. In the present specification, in a case where a divalent aromatic hydrocarbon group is referred to, it represents a divalent group obtained by removing any two hydrogen atoms from an aromatic hydrocarbon ring. Examples thereof include a divalent group obtained by removing any one of hydrogen atoms from the above-mentioned (monovalent) aromatic hydrocarbon group.

In the present specification, examples of aromatic heterocyclic rings include furan, thiophene, pyrrole, imidazole, isothiazole, isoxazole, pyridine, pyrazine, quinoline, benzofuran, benzothiazole, benzoxazole, and the like.

In the present specification, in a case where an aromatic heterocyclic group is referred to, it represents a monovalent group obtained by removing any one of hydrogen atoms from an aromatic heterocyclic ring. Examples of monovalent aromatic heterocyclic groups include a furyl group, a thienyl group (preferably a 2-thienyl group), a pyrrolyl group, an imidazolyl group, an isothiazolyl group, an isoxazolyl group, a pyridyl group, a pyrazinyl group, a quinolyl group, a benzofuranyl group (preferably a 2-benzofuranyl group), a benzothiazolyl group (preferably a 2-benzothiazolyl group), a benzoxazolyl group (preferably a 2-benzoxazolyl group), and the like. In the present specification, in a case where a divalent aromatic heterocyclic group is referred to, it represents a divalent group obtained by removing any two hydrogen atoms from an aromatic heterocyclic ring. Examples thereof include a divalent group obtained by removing any one of hydrogen atoms from the above-mentioned (monovalent) aromatic heterocyclic group.

<Lens Adhesive>

A lens adhesive of the embodiment of the present invention includes a compound represented by General Formula 1. The lens adhesive may further include other components in addition to the compound represented by General Formula 1. Specific examples of other components include additives such as a polymer, a monomer, a dispersant, a plasticizer, a thermal stabilizer, or a mold release agent which are other than the components described above, in addition to a (meth)acrylate monomer and a polymerization initiator.

A viscosity of the lens adhesive including the compound represented by General Formula 1 is preferably 60 to 5,000 mPa·s or less, more preferably 80 to 3,000 mPa·s, and even more preferably 100 to 2,000 mPa·s. By setting a viscosity of the lens adhesive within the above range, it is possible to improve handleability in a case of adhesion, thereby forming a high-quality adhesive layer.

[Compound Represented by General Formula (A)]

The lens adhesive of the embodiment of the present invention includes the compound represented by General Formula 1.

$$Pol_1\text{-}Sp_1\text{-}L_1\text{-}Ar\text{-}L_2\text{-}Sp_2\text{-}Pol_2 \qquad \text{(General Formula 1)}$$

In the formula, Ar is any of aromatic ring groups represented by General Formulas 2-1 to 2-4.

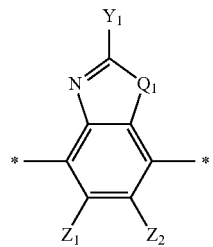

General Formula 2-1

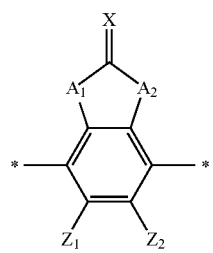

General Formula 2-2

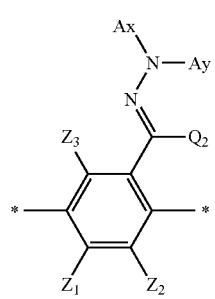

General Formula 2-3

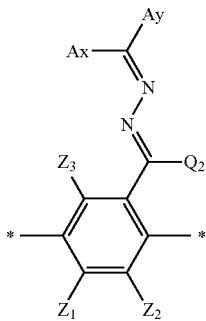

General Formula 2-4

In General Formulas 2-1 to 2-4, $Q_1$ represents —S—, —O—, or $NR_{11}$—, and $R_{11}$ represents a hydrogen atom or an alkyl group having 1 to 6 carbon atoms.

$Y_1$ represents an alkyl group which has 1 to 6 carbon atoms and may have a substituent; an aromatic hydrocarbon group which has 6 to 12 carbon atoms and may have a substituent; or an aromatic heterocyclic group which has 3 to 12 carbon atoms and may have a substituent, $Z_1$, $Z_2$, and $Z_3$ each independently represent a hydrogen atom, an aliphatic hydrocarbon group which has 1 to 20 carbon atoms and may have a substituent, an alkoxy group which has 1 to 20 carbon atoms and may have a substituent, an alicyclic hydrocarbon group which has 3 to 20 carbon atoms and may have a substituent, a monovalent aromatic hydrocarbon group which has 6 to 20 carbon atoms and may have a substituent, a halogen atom, a cyano group, a nitro group, $-NR_{12}R_{13}$, or $SR_{12}$, where, $Z_1$ and $Z_2$ may be bonded to each other to form an aromatic hydrocarbon ring which may have a substituent or an aromatic heterocyclic ring which may have a substituent, and $R_{12}$ and $R_{13}$ each independently represent a hydrogen atom or an alkyl group having 1 to 6 carbon atoms.

$A_1$ and $A_2$ each independently represent a group selected from the group consisting of —O—, —$NR_{21}$— (where $R_{21}$ represents a hydrogen atom or a substituent), —S—, and —C(=O)—; and X represents O, S, C to which a hydrogen atom or a substituent is bonded, or N to which a hydrogen atom or a substituent is bonded.

Ax represents an organic group which has 1 to 30 carbon atoms and has at least one aromatic ring selected from the group consisting of an aromatic hydrocarbon ring and an aromatic heterocyclic ring; and Ay represents a hydrogen atom, an alkyl group which has 1 to 6 carbon atoms and may have a substituent, or an organic group which has 1 to 30 carbon atoms and has at least one aromatic ring selected from the group consisting of an aromatic hydrocarbon ring and an aromatic heterocyclic ring, where, the aromatic ring included in Ax and Ay may have a substituent, and Ax and Ay may be bonded to each other to form a ring which may have a substituent.

$Q_2$ represents a hydrogen atom, or an alkyl group which has 1 to 6 carbon atoms and may have a substituent.

The symbol * indicates a binding position with $L_1$ or $L_2$.

Regarding definitions and preferable ranges of respective substituents in General Formulas 2-1 to 2-4, descriptions of $Y^1$, $Q^1$, and $Q^2$ which relate to a compound (A) described in JP2012-021068A can be respectively referred to for $Y_1$, $Z_1$, and $Z_2$; descriptions of $A_1$, $A_2$, and X which relate to a compound represented by General Formula (I) described in JP2008-107767A can be respectively referred to for $A_1$, $A_2$, and X; descriptions of $A^x$, $A^y$, and $Q^1$ which relate to a compound represented by General Formula (I) described in WO2013/018526A can be respectively referred to for Ax, Ay, and $Q_2$ of General Formula 2-3; and descriptions regarding $A^a$, $A^b$, and $Q^{11}$ which relate to a compound represented by General Formula (II) described in WO2013/018526A can be respectively referred to for Ax, Ay, and $Q_2$ of General Formula 2-4. Regarding $Z_3$, a description of $Q^1$ relating to a compound (A) described in JP2012-021068A can be referred to.

X in General Formula 2-2 is preferably C to which two substituents are bonded, and both $A_1$ and $A_2$ are preferably —S—. In General Formula 2-3, as a ring in a case where Ax and Ay are bonded to each other to form a ring which may have a substituent, the ring is preferably an alicyclic hydrocarbon ring, an aromatic hydrocarbon ring, or an aromatic heterocyclic ring, and is more preferably an aromatic heterocyclic ring. In General Formula 2-4, as a ring in a case where Ax and Ay are bonded to each other to form a ring which may have a substituent, the ring is preferably an unsaturated hydrocarbon ring.

Ar in General Formula 1 is preferably an aromatic ring group represented by General Formula 2-2.

The aromatic ring group represented by General Formula 2-2 is particularly preferably an aromatic ring group represented by General Formula 2-2-1.

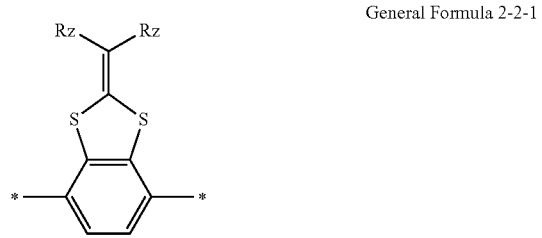

General Formula 2-2-1

In the formula, Rz represents a substituent. Examples of substituents shown by Rz include a substituent that is shown as a substituent of $Sp_1$ to be described later, and the like. Two Rz's may be the same as or different from each other. In addition, two Rz's may be bonded to each other to form a ring. A ring formed in this case is preferably a 5-membered ring or a 6-membered ring, is more preferably a 5-membered ring or a 6-membered ring containing nitrogen or oxygen as an element constituting the ring, and is particularly preferably a ring represented by any of the following formulas.

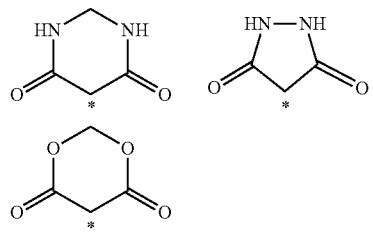

In the above formula, each * represents a position of a carbon atom to which two Rz's are bonded in General Formula 2-2-1. In addition, the ring represented by the above formula may have a substituent in nitrogen or carbon. In this case, the substituent is preferably an alkyl group having 1 to 6 carbon atoms, and is more preferably a linear alkyl group having 1 to 4 carbon atoms.

The aromatic ring group represented by General Formula 2-2-1 is preferably an aromatic ring group in which at least one Rz is a cyano group, or an aromatic ring group in which two Rz's are bonded to form a ring, and is more preferably an aromatic ring group in which two Rz's are both cyano groups.

The reason for this is because, in the lens adhesive including the compound represented by General Formula 1 having such an aromatic ring group, an effect of increasing absorption in an ultraviolet range while maintaining high transmittivity in a visible light region can become more remarkable.

In General Formula 1, $L_1$ and $L_2$ each independently represent a single bond, or a linking group selected from the group consisting of —O—, —S—, —C(=O)—, —OC(=O)—, —C(=O)O—, —OC(=O)O—, —$NR_{101}$C(=O)—, —C(=O)$NR_{102}$—, —OC(=O)$NR_{103}$—, —$NR_{104}$C(=O)O—, —SC(=O)—, and C(=O)S—. In the description of the above-mentioned linking group, the left side is bonded to Ar, and the right side is bonded to $Sp_1$ or $Sp_2$. $R_{101}$, $R_{102}$, $R_{103}$, and $R_{104}$ each independently represent -$Sp_3$-$Pol_3$ or a halogen atom. $L_1$ and $L_2$ each independently preferably are —O—, —OC(=O)—, —C(=O)O—, —OC(=O)O—, —$NR_{101}$C(=O)—, —C(=O)$NR_{102}$—, —OC(=O)$NR_{103}$—, or —$NR_{104}$C(=O)O—, more preferably are —O—, —OC(=O)—, —OC(=O)O—, or —OC(=O)$NR_{103}$, and even more preferably are —O—.

$L_1$ and $L_2$ may be the same as or different from each other, but they are preferably the same.

$Sp_1$ and $Sp_2$ each represent a single bond, or a linking group selected from the group consisting of a linear alkylene group which has 1 to 30 carbon atoms and may have a substituent, and a group in which one or two or more non-adjacent —$CH_2$—'s are substituted by —O—, —S—, —C(=O)—, —OC(=O)—, —C(=O)O—, —OC(=O)O—, —$NR_{201}$C(=O)—, —C(=O)$NR_{202}$—, —OC(=O)$NR_{203}$—, —$NR_{204}$C(=O)O—, —SC(=O)—, or —C(=O)S— in a linear alkylene group which has 1 to 30 carbon atoms and may have a substituent.

$R_{201}$, $R_{202}$, $R_{203}$, and $R_{204}$ each independently represent -$Sp_4$-$Pol_4$ or a halogen atom.

$Sp_1$ and $Sp_2$ may be the same as or different from each other, but they are preferably the same.

In a linking group in which —$CH_2$— is substituted with other divalent groups selected from the group consisting of —O—, —S—, —C(=O)—, —OC(=O)—, —C(=O)O—, —OC(=O)O—, —$NR_{201}$C(=O)—, —C(=O)$NR_{202}$—, —OC(=O)$NR_{203}$—, —$NR_{204}$C(=O)O—, —SC(=O)—, and —C(=O)S— in a linear alkylene group having 2 to 30 carbon atoms represented by $Sp_1$ and $Sp_2$, it is preferable that the other substituted divalent groups be not directly bonded to $L_1$ or $L_2$. That is, a site substituted by the other divalent group is preferably not an $L_1$ side terminal of $Sp_1$, and an $L_2$ side terminal of $Sp_2$. That is, a terminal on an $L_1$ side or an $L_2$ side is preferably —$CH_2$—. Accordingly, a group, in which one or two or more non-adjacent —$CH_2$—'s are substituted by any of the above-described other groups in a linear alkylene group which has 1 to 30 carbon atoms and may have a substituent, is preferably a group in which a terminal on the $L_1$ side or the $L_2$ side is —$CH_2$—, in a group in which one or two or more non-adjacent —$CH_2$—'s are substituted by any of the above-described other groups in a linear alkylene group which has 2 to 30 carbon atoms and may have a substituent.

It is more preferable that the divalent linking groups represented by $Sp_1$ and $Sp_2$ each independently represent a linking group selected from the group consisting of groups in which one or two or more non-adjacent —CH₂—'s are substituted by —O—, —C(=O)—, —OC(=O)—, —C(=O)O—, —OC(=O)O—, —NR₂₀₁C(=O)—, —C(=O)NR₂₀₂—, —OC(=O)NR₂₀₃—, or —NR₂₀₄C(=O)O— in a linear alkylene group which has 1 to 20 carbon atoms and may have a substituent, and a linear alkylene group which has 2 to 20 carbon atoms and may have a substituent. It is even more preferable that the divalent linking groups represented by Sp₁ and Sp₂ each independently represent a linking group selected from the group consisting of groups in which one or two or more non-adjacent —CH₂—'s are substituted by —O—, —C(=O)—, —OC(=O)—, or —C(=O)O— in a linear alkylene group which has 1 to 10 carbon atoms and may have a substituent, and a linear alkylene group which has 2 to 10 carbon atoms and may have a substituent. It is particularly preferable that the divalent linking groups represented by Sp₁ and Sp₂ each independently represent a linking group selected from the group consisting of groups in which one or two or more non-adjacent —CH₂—'s are substituted by —O—, —C(=O)—, —OC(=O)—, or —C(=O)O— in a linear alkylene group which has 1 to 10 carbon atoms and which has no substituent or has a methyl group as a substituent, and a linear alkylene group which has 2 to 10 carbon atoms and which has no substituent or has a methyl group as a substituent.

Sp₃ and Sp₄ each independently represent a single bond or a divalent linking group. Examples of divalent linking groups include the following linking groups, and linking groups selected from the group consisting of two or more combinations of the following linking groups.

A linear alkylene group that may have a substituent; a cycloalkylene group that may have a substituent (for example, a trans-1,4-cyclohexylene group); a divalent aromatic hydrocarbon group that may have a substituent (for example, a 1,4-phenylene group); a divalent aromatic heterocyclic group that may have a substituent; —O—; —S—; —C(=O)—; —OC(=O)—; —C(=O)O—; —OC(=O)O; —NR₂₀₁C(=O)—; —C(=O)NR₂₀₂—; —OC(=O)NR₂₀₃—; —NR₂₀₄C(=O)O—; —SC(=O)—; and —C(=O)S—.

Examples of Sp₃ and Sp₄ which are divalent linking groups respectively include a linear alkylene group that may have a substituent; a cycloalkylene group that may have a substituent; a divalent aromatic hydrocarbon group that may have a substituent; a divalent aromatic heterocyclic group that may have a substituent; two or more linking groups which are selected from the group consisting of a linear alkylene group that may have a substituent, a cycloalkylene group that may have a substituent, a divalent aromatic hydrocarbon group that may have a substituent, and a divalent aromatic heterocyclic group that may have a substituent, and which are bonded via a linking group selected from the group consisting of a single bond, —O—, —C(=O)—, —OC(=O)—, —C(=O)O—, —OC(=O)O—, —NR₂₀₁C(=O)—, and —C(=O)NR₂₀₂—; and the like.

The divalent linking groups respectively represented by Sp₃ and Sp₄ is preferably a single bond or a linear alkylene group which has 1 to 10 carbon atoms and may have a substituent, is more preferably a linear alkylene group which has 1 to 5 carbon atoms and may have a substituent, is even more preferably a linear alkylene group which has 1 to 3 carbon atoms and may have a substituent, and is particularly preferably an unsubstituted linear alkylene group.

In the description of the linking group, the left side is bonded to L₁, L₂, or N (in the case of Sp₃ and Sp₄), and the right side is bonded to Pol₁, Pol₂, Pol₃, or Pol₄.

Pol₁, Pol₂, Pol₃, and Pol₄ each independently represent a hydrogen atom or a polymerizable group. Examples of polymerizable groups include polymerizable groups represented by Formulas Pol-1 to Pol-6.

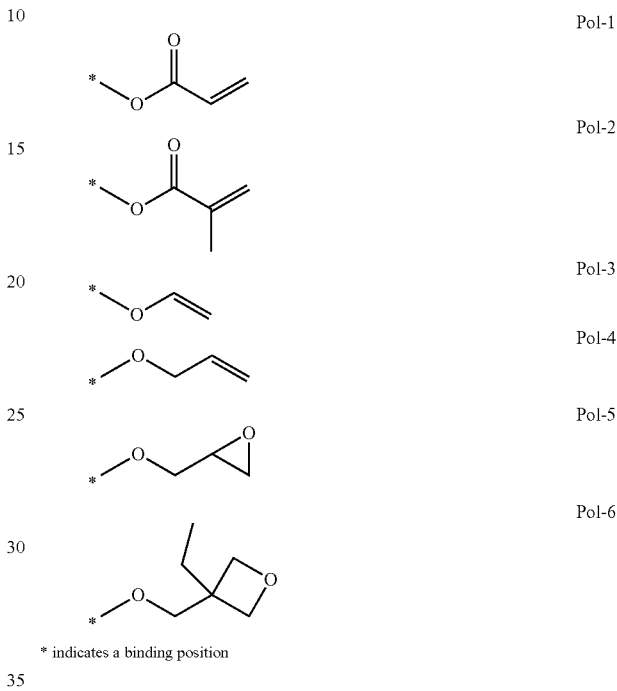

* indicates a binding position

Among them, (meth)acryloyloxy groups (Pol-1, Pol-2) are preferable as polymerizable groups.

Any one of Pol₁ or Pol₂ is preferably a polymerizable group, and more preferably a (meth)acryloyloxy group. Both of Pol₁ and Pol₂ are even more preferably (meth)acryloyloxy groups.

Pol₁ and Pol₂ may be the same as or different from each other, but they are preferably the same.

The compound represented by General Formula 1 has at least one polymerizable group. The compound represented by General Formula 1 preferably has at least two polymerizable groups.

Any of Pol₃ or Pol₄ is preferably a hydrogen atom.

R₁₀₁, R₁₀₂, R₁₀₃, and R₁₀₄ each independently represent -Sp₃-Pol₃ or a halogen atom. R₁₀₁, R₁₀₂, R₁₀₃, and R₁₀₄ each independently preferably are a hydrogen atom, an alkyl group having 1 to 4 carbon atoms, or a halogen atom.

R₂₀₁, R₂₀₂, R₂₀₃, and R₂₀₄ each independently represent -Sp₄-Pol₄ or a halogen atom. R₂₀₁, R₂₀₂, R₂₀₃, and R₂₀₄ each independently preferably are a hydrogen atom, an alkyl group having 1 to 4 carbon atoms, or a halogen atom.

A substituent referred to in the case of referring to the phrase "may have a substituent" regarding the substituents in Sp₁, Sp₂, Sp₃, Sp₄, and General Formulas 2-1 to 2-4 is not particularly limited. Examples thereof include an alkyl group, a cycloalkyl group, an alkoxy group, an acyl group, an acyloxy group, an alkoxycarbonyl group, an amide group, an amino group, a halogen atom, a nitro group, and a cyano group, and a substituent selected from the group consisting of groups composed of a combination of two or more substituents among the above-mentioned substituents.

The substituent may be a group represented by -Sp$_5$-Pol$_5$. Sp$_5$ and Pol$_5$ each are synonymous with Sp$_1$ and Pol$_1$, and their preferable ranges are also the same. The number of substituents is not particularly limited, and 1 to 4 substituents may be present. In a case where there are two or more substituents, the two or more substituents may be the same as or different from each other.

Examples of specific structures of Pol$_1$-Sp$_1$-L$_1$- or Pol$_2$-Sp$_2$-L$_2$- include the following structures.

Pol$_1$-Sp$_1$-L$_1$- or Pol$_2$-Sp$_2$-L$_2$- may be the same as or different from each other, but they are preferably the same.

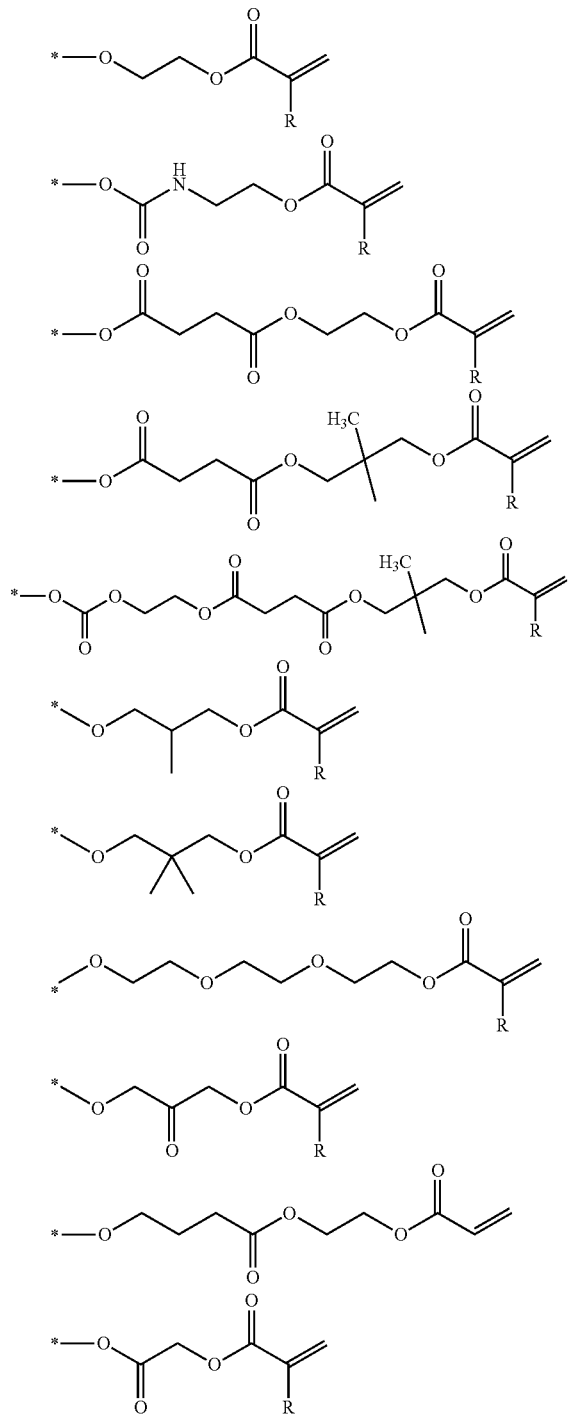

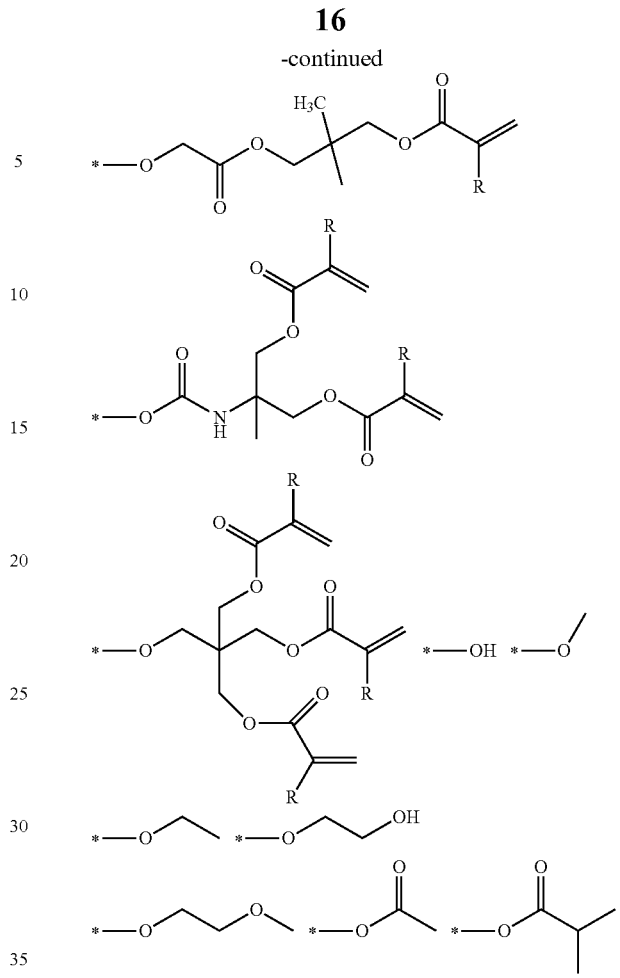

(R represents a hydrogen atom or a methyl group, and * represents a binding position with Ar.)

In the present specification, the following structure shows mixture of two partial structures of which methyl groups are respectively bonded to any one carbon of an ethylene group.

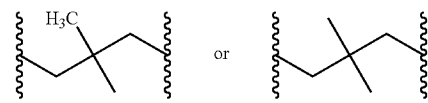

As described above, in a case where the compound represented by General Formula 1 has a structure in which a substituent is substituted on a linear alkylene group, structural isomers having different substitution positions of the substituent may be present. The compound represented by General Formula 1 may be a mixture of such structural isomers.

The compound represented by General Formula 1 is preferably a non-liquid crystalline compound.

Specific examples of the compound represented by General Formula 1 which is preferably used in the lens adhesive of the embodiment of the present invention are listed below, but the compounds are not limited to the following compounds. In the following structural formulas, Me represents a methyl group, Et represents an ethyl group, nPr represents an n-propyl group, iPr represents an isopropyl group, nBu represents an n-butyl group, and tBu represents a t-butyl group.

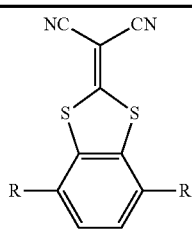
| | |
|---|---|
| 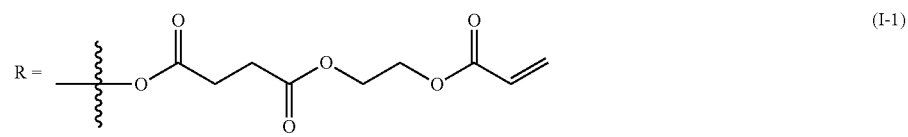 | (I-1) |
| 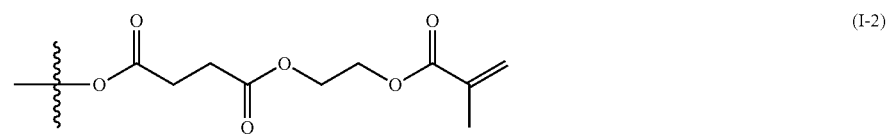 | (I-2) |
| 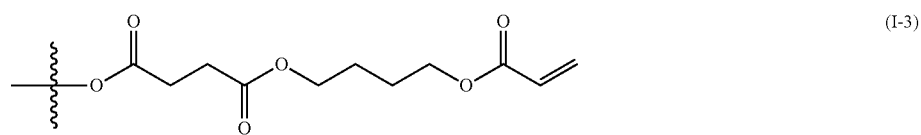 | (I-3) |
| 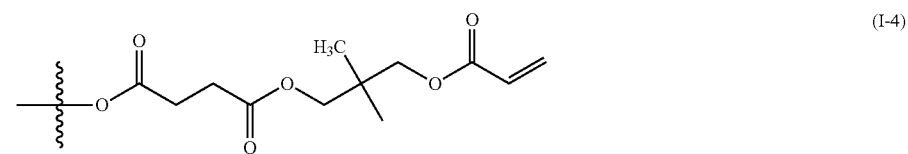 | (I-4) |
| 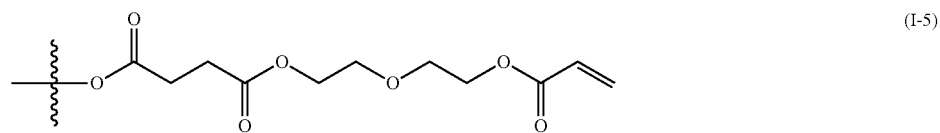 | (I-5) |
| 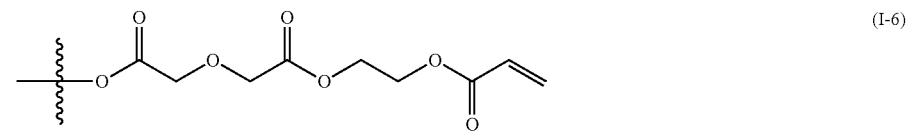 | (I-6) |
| 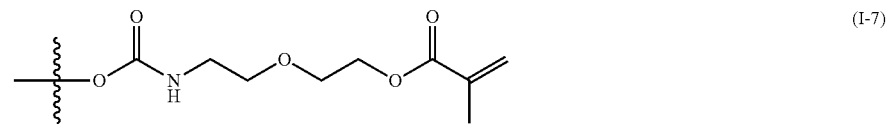 | (I-7) |
| 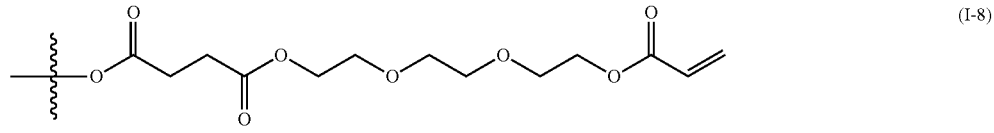 | (I-8) |
| 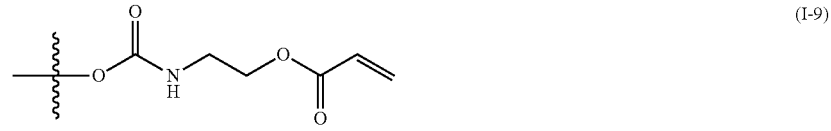 | (I-9) |
| 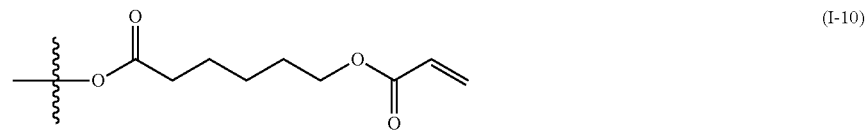 | (I-10) |

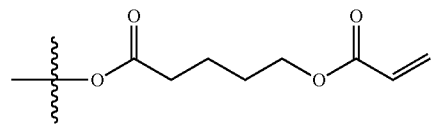 [SMILES: *OC(=O)CCCCOC(=O)C=C]
(I-11)
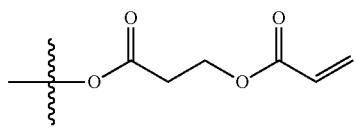 [SMILES: *OC(=O)CCOC(=O)C=C]
(I-12)
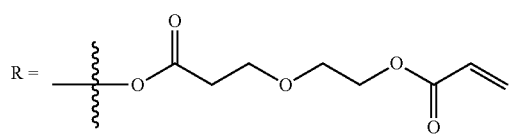 [SMILES: *OC(=O)CCOCCOC(=O)C=C]
(I-13)
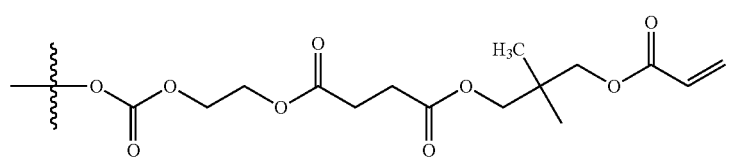
(I-14)
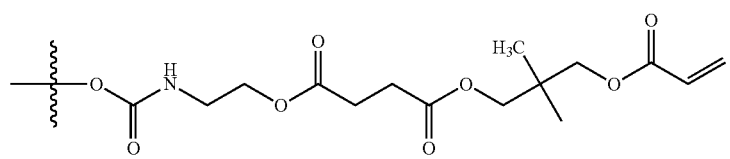 [SMILES: *OC(=O)NCCOC(=O)CCC(=O)OCC(C)(C)COC(=O)C=C]
(I-15)
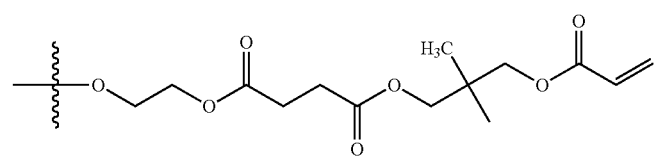 [SMILES: *OCCOC(=O)CCC(=O)OCC(C)(C)COC(=O)C=C]
(I-16)
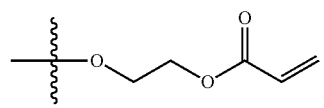
(I-17)
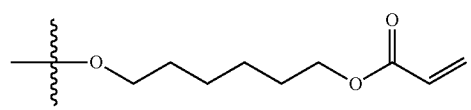 [SMILES: *OCCCCCCOC(=O)C=C]
(I-18)
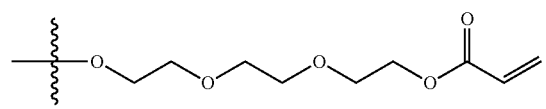 [SMILES: *OCCOCCOCCOC(=O)C=C]
(I-19)
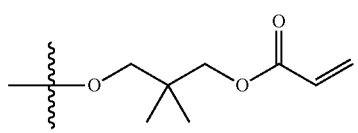 [SMILES: *OCC(C)(C)COC(=O)C=C]
(I-20)
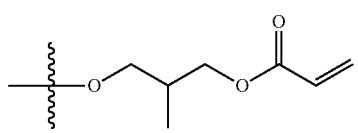 [SMILES: *OCC(C)COC(=O)C=C]
(I-21)

-continued
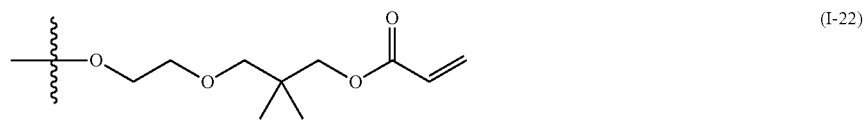 (I-22)
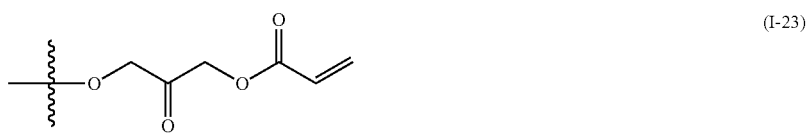 (I-23)
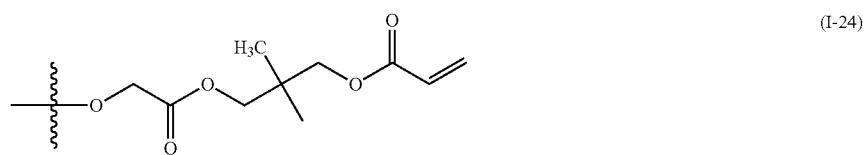 (I-24)
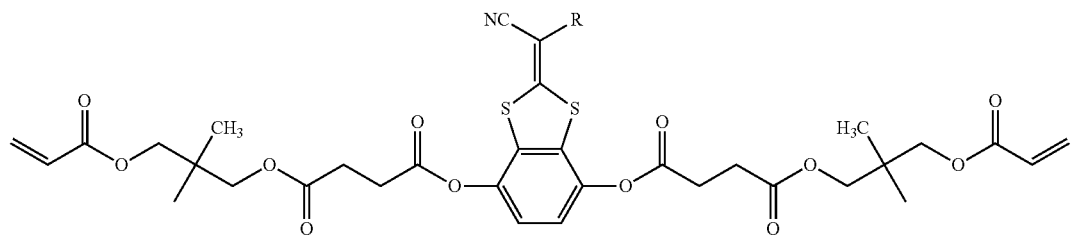
 (III-1)
R =
 (III-2)
 (III-3)
 (III-4)
R =  (III-5)
 (III-6)
 (III-7)

-continued
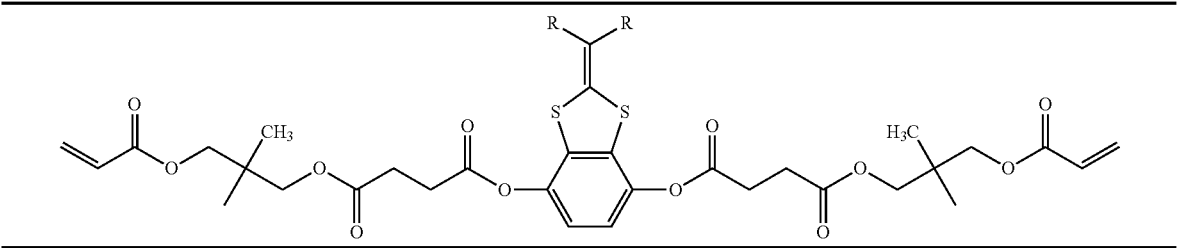
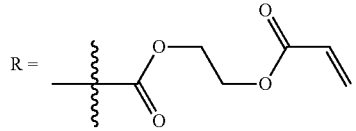 [SMILES: *C(=O)OCCOC(=O)C=C] (III-8)
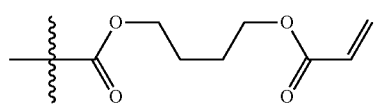 [SMILES: *C(=O)OCCCCOC(=O)C=C] (III-9)
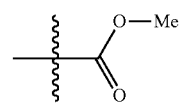 (III-10)
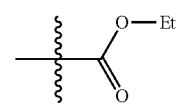 (III-11)
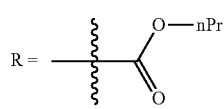 (III-12)
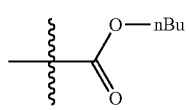 (III-13)
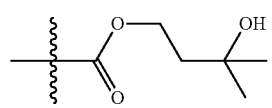 (III-14)
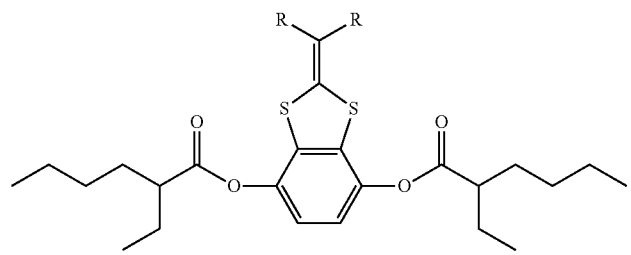
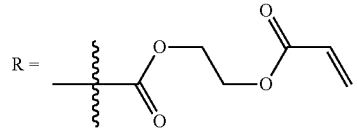 (III-15)
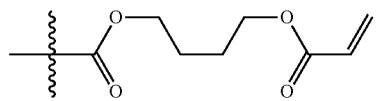 [SMILES: *C(=O)OCCCCOC(=O)C=C] (III-16)

-continued
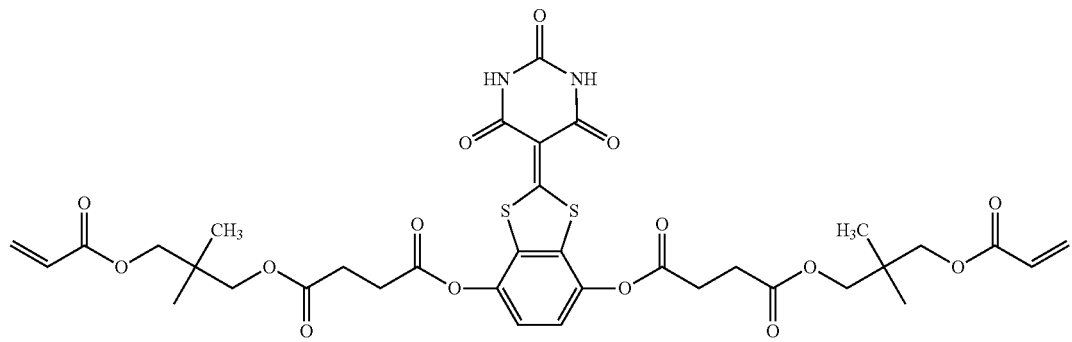 [SMILES: C=CC(=O)OCC(C)(C)COC(=O)CCC(=O)Oc1ccc(OC(=O)CCC(=O)OCC(C)(C)COC(=O)C=C)c2c1SC(=C1C(=O)NC(=O)NC1=O)S2]
(III-17)
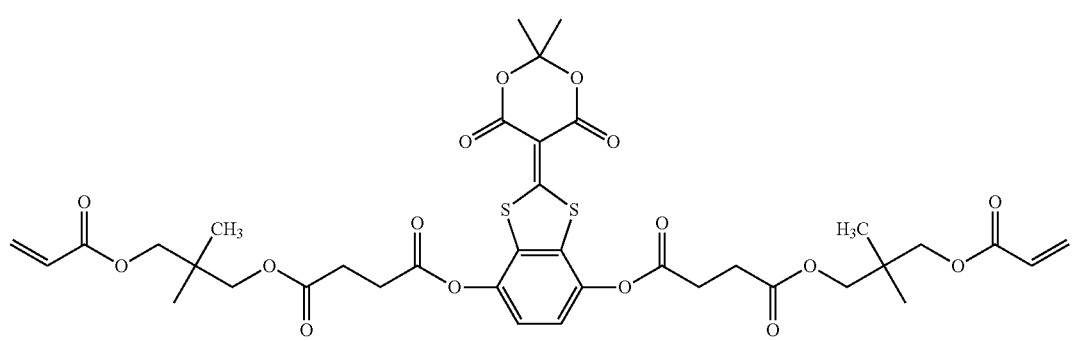 [SMILES: C=CC(=O)OCC(C)(C)COC(=O)CCC(=O)Oc1ccc(OC(=O)CCC(=O)OCC(C)(C)COC(=O)C=C)c2c1SC(=C1C(=O)OC(C)(C)OC1=O)S2]
(III-18)
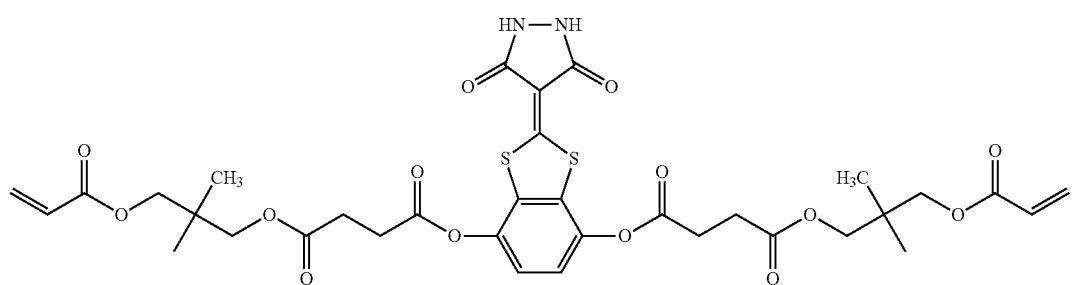 [SMILES: C=CC(=O)OCC(C)(C)COC(=O)CCC(=O)Oc1ccc(OC(=O)CCC(=O)OCC(C)(C)COC(=O)C=C)c2c1SC(=C1C(=O)NNC1=O)S2]
(III-19)
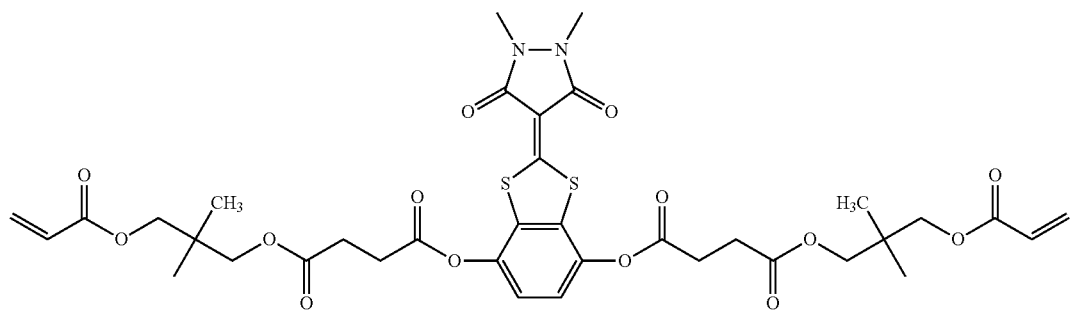 [SMILES: C=CC(=O)OCC(C)(C)COC(=O)CCC(=O)Oc1ccc(OC(=O)CCC(=O)OCC(C)(C)COC(=O)C=C)c2c1SC(=C1C(=O)N(C)N(C)C1=O)S2]
(III-20)
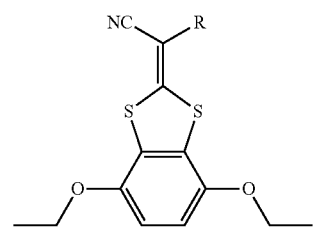
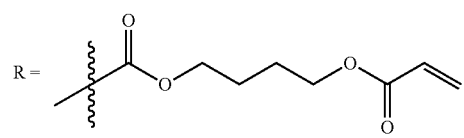 [SMILES: *C(=O)OCCCCOC(=O)C=C]
(III-21)

-continued
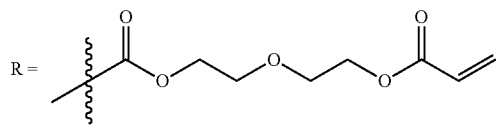 [SMILES: *C(=O)OCCOCCOC(=O)C=C]
(III-22)
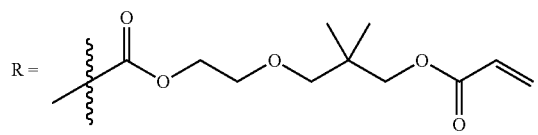 [SMILES: *C(=O)OCCOCC(C)(C)COC(=O)C=C]
(III-23)
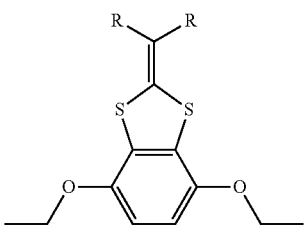
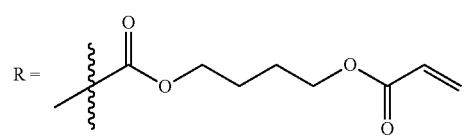 [SMILES: *C(=O)OCCCCOC(=O)C=C]
(III-24)
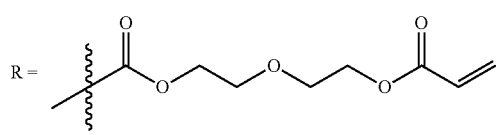 [SMILES: *C(=O)OCCOCCOC(=O)C=C]
(III-25)
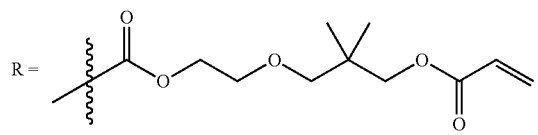
(III-26)
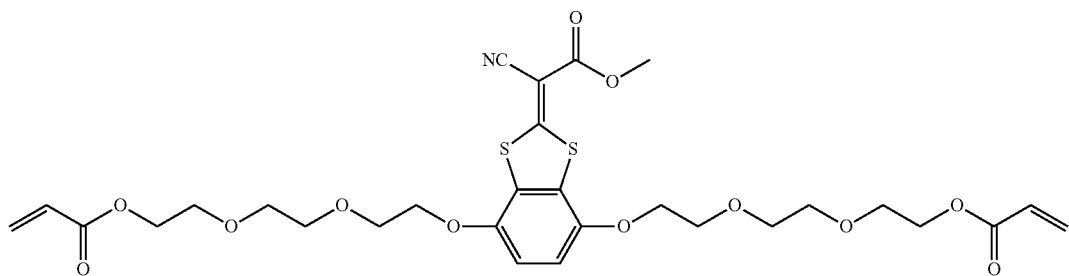 [SMILES: C=CC(=O)OCCOCCOCCOc1ccc(OCCOCCOCCOC(=O)C=C)c2c1SC(=C(C#N)C(=O)OC)S2]
(III-27)
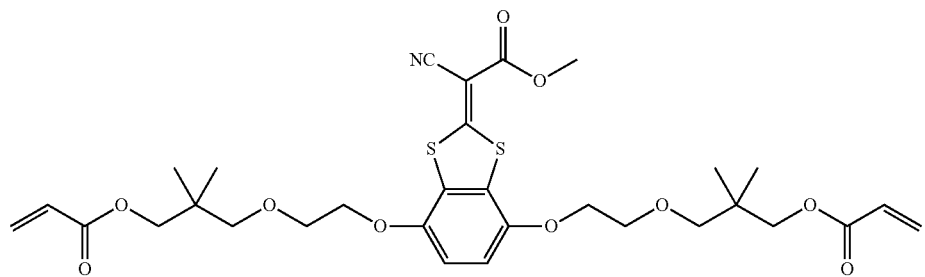 [SMILES: C=CC(=O)OCC(C)(C)COCCOc1ccc(OCCOCC(C)(C)COC(=O)C=C)c2c1SC(=C(C#N)C(=O)OC)S2]
(III-28)

-continued
(III-29)
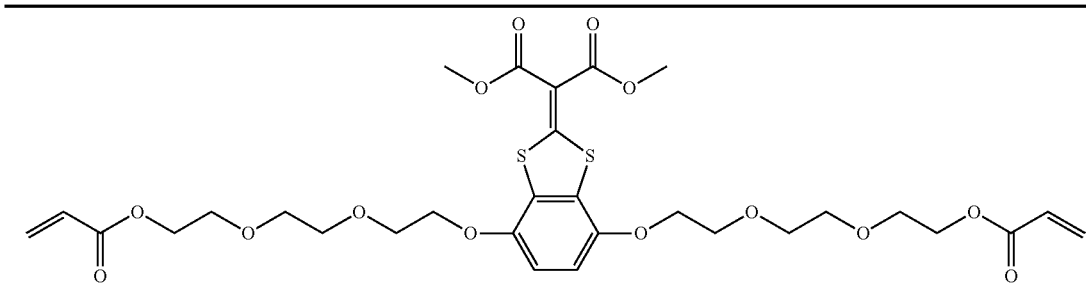
(III-30)
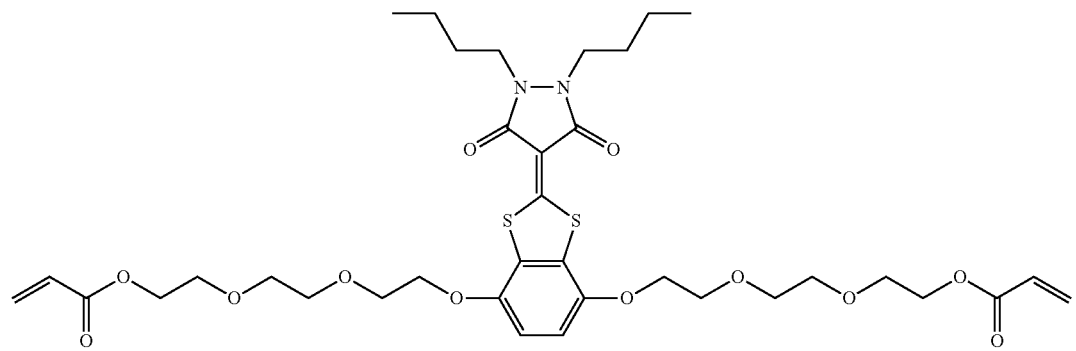 [SMILES: C=CC(=O)OCCOCCOCCOc1ccc(OCCOCCOCCOC(=O)C=C)c2c1SC(=C1C(=O)N(CCCC)N(CCCC)C1=O)S2]
(III-31)
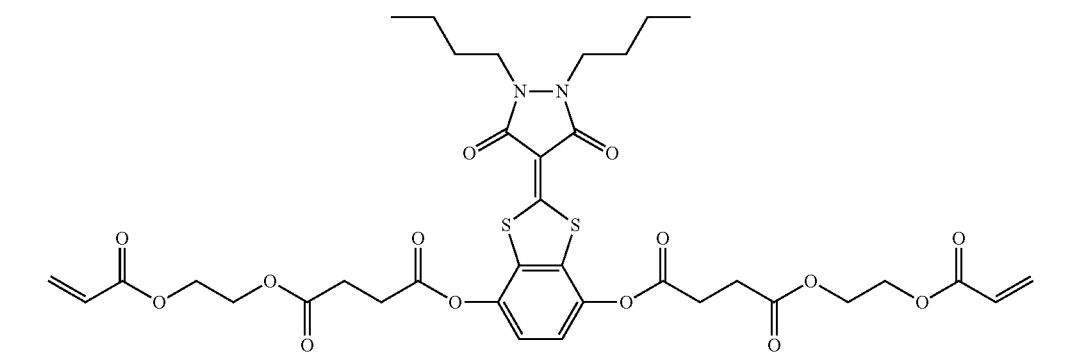 [SMILES: C=CC(=O)OCCOC(=O)CCC(=O)Oc1ccc(OC(=O)CCC(=O)OCCOC(=O)C=C)c2c1SC(=C1C(=O)N(CCCC)N(CCCC)C1=O)S2]
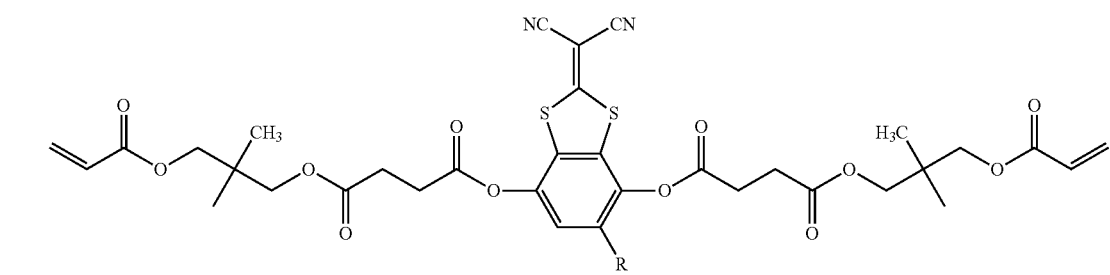
(IV-1)
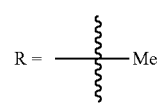
(IV-2)
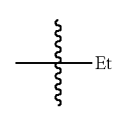
(IV-3)
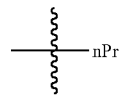

-continued
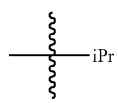 (IV-4)
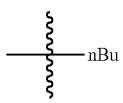 (IV-5)
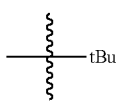 (IV-6)
R = 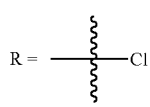 (IV-7)
 (IV-8)
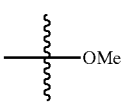 (IV-9)
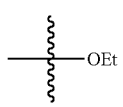 (IV-10)
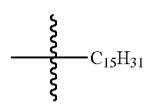 (IV-11)
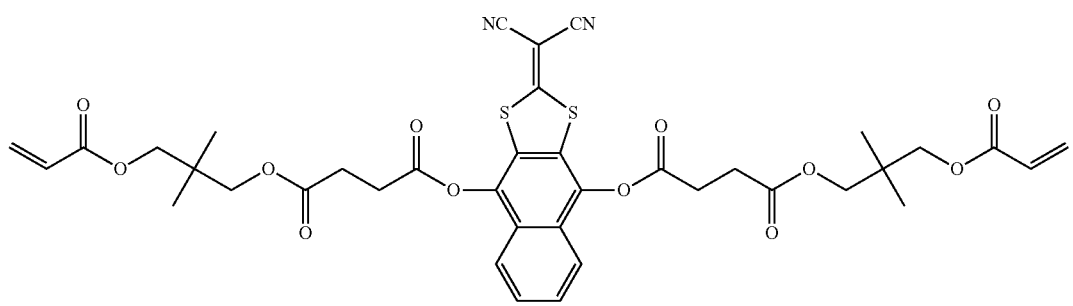 [SMILES: C=CC(=O)OCC(C)(C)COC(=O)CCC(=O)Oc1c2c(c(OC(=O)CCC(=O)OCC(C)(C)COC(=O)C=C)c3ccccc13)SC(=C(C#N)C#N)S2] (IV-12)
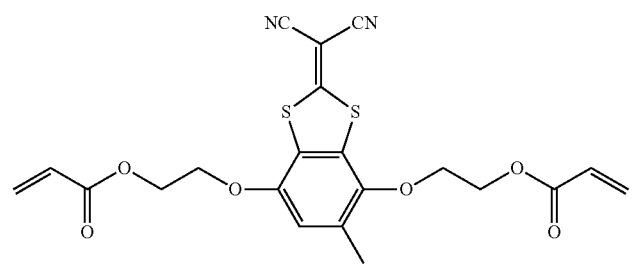 [SMILES: C=CC(=O)OCCOc1cc(C)c(OCCOC(=O)C=C)c2c1SC(=C(C#N)C#N)S2] (IV-13)

-continued
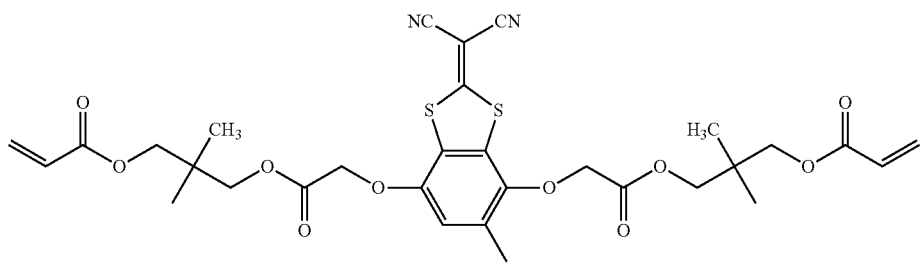 [SMILES: C=CC(=O)OCC(C)(C)COC(=O)COc1cc(C)c(OCC(=O)OCC(C)(C)COC(=O)C=C)c2c1SC(=C(C#N)C#N)S2]
(IV-14)
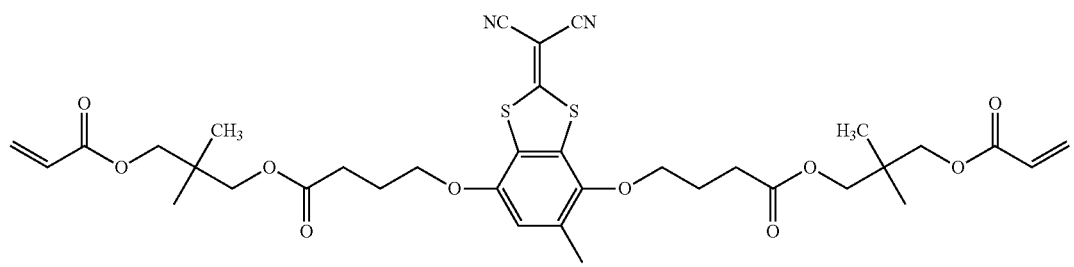 [SMILES: C=CC(=O)OCC(C)(C)COC(=O)CCCOc1cc(C)c(OCCCC(=O)OCC(C)(C)COC(=O)C=C)c2c1SC(=C(C#N)C#N)S2]
(IV-15)
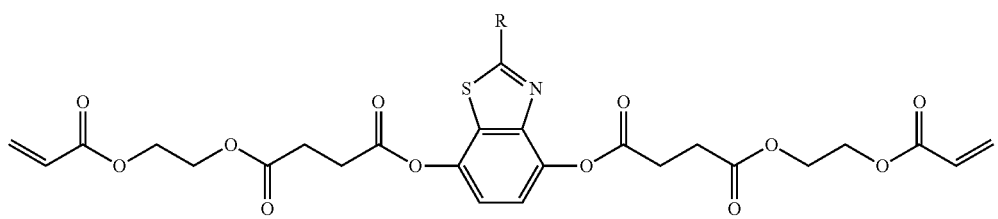
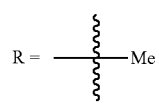
(V-1)
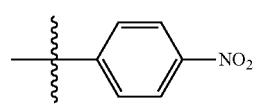
(V-2)
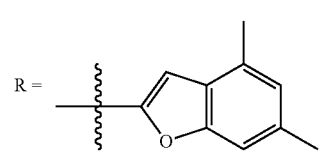 [SMILES: *c1cc2c(C)cc(C)cc2o1]
(V-3)
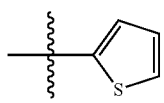
(V-4)
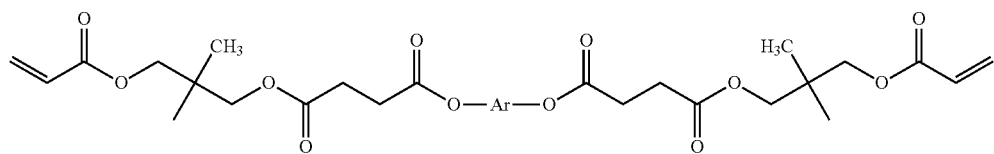

-continued
Ar = 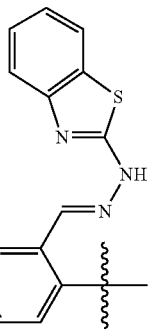 (VI-1)
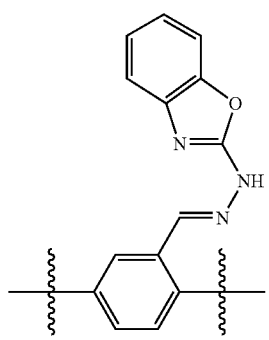 [SMILES: *c1ccc(*)c(/C=N/Nc2nc3ccccc3o2)c1] (VI-2)
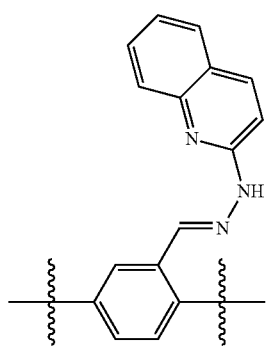 [SMILES: *c1ccc(*)c(/C=N/Nc2ccc3ccccc3n2)c1] (VI-3)
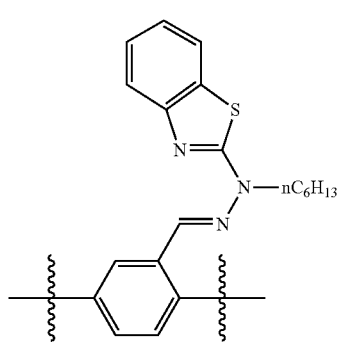 (VI-4)
Ar = 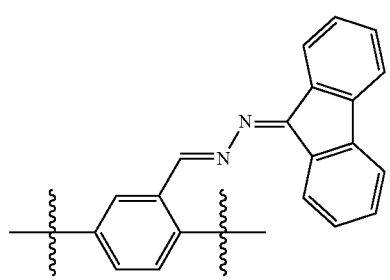 (VI-6)

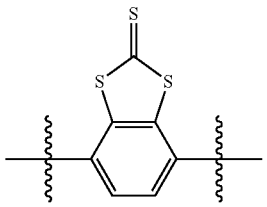 [SMILES: *c1ccc(*)c2sc(=S)sc12]

(VI-7)

The compound represented by General Formula 1 has one or two or more asymmetric carbons in some cases, and regarding stereochemistry of such asymmetric carbons, compounds represented by General Formula 1 each independently can be any of an (R) isomer or an (S) isomer. In addition, the compound represented by Formula (A) may be a mixture of stereoisomers such as optical isomers or diastereoisomers. In other words, the compound represented by Formula (A) may be any kind of stereoisomer, may be any mixture of stereoisomers, or may be a racemate.

A content of the compound represented by General Formula 1 in the lens adhesive is preferably 10% by mass to 90% by mass, is more preferably 15% by mass to 85% by mass, and is even more preferably 20% by mass to 80% by mass with respect to a total mass of the lens adhesive. By setting the content to 90% by mass or less, a viscosity can be set within a preferable range.

Two or more compounds represented by General Formula 1 may be contained in the lens adhesive. In a case where two or more compounds represented by General Formula 1 are contained, the total content thereof is preferably within the above range.

[Polymer]

The lens adhesive may include a polymer or an oligomer (hereinafter also referred to as a "polymer") for the purpose of adjusting a viscosity or a Young's modulus of a cured material. The polymer is not particularly limited, but is preferably a polymer having an ethylenically unsaturated group. The ethylenically unsaturated group may be contained in any of the inside of a main chain, a terminal of the main chain, and a side chain of the polymer. The ethylenically unsaturated group is not particularly limited, but is preferably an ethylenically unsaturated bond derived from butadiene or isoprene, or a (meth)acryloyl group.

The polymer contained in the lens adhesive is preferably a polymer selected from the group consisting of a conjugated diene polymer and a polyurethane resin having an ethylenically unsaturated group, and is more preferably a polymer having a polybutadiene structure, a polymer having a polyisoprene structure, and a polymer selected from the group consisting of urethane (meth)acrylates.

Commercially available products of a polymer having a polybutadiene structure include, for example, NIPOL BR series (manufactured by Zeon Corporation), UBEPOL BR series (manufactured by UBE INDUSTRIES, LTD.), NISSO-PB series (manufactured by Nippon Soda Co., Ltd.), KURARAY LIQUID RUBBER LBR series and KURARAY LIQUID RUBBER L-SBR series (manufactured by Kuraray Co., Ltd.), and the like.

Commercially available products of a polymer having a polyisoprene structure include, for example, NIPOL IR series (manufactured by Zeon Corporation), KURARAY LIQUID RUBBER LIR series and KURARAY LIQUID RUBBER UC series (manufactured by Kuraray Co., Ltd.), and the like.

Commercially available products of urethane (meth)acrylate include, for example, UV-3200, UV-3000B, UV-3700B, UV-3210EA, UV-2000B, and UV-3630 of SHIKOH (registered trademark) series (all of which are manufactured by Nippon Synthetic Chemical Industry Co., Ltd.), EBECRYL 230 and EBECRYL 9227EA (which are manufactured by Daicel Psytech Co., Ltd.), AU-3040, AU-3050, AU-3090, AU-3110, and AU-3120 of Hi-Cope AU (registered trademark) series (all of which are manufactured by TOKUSHIKI CO., Ltd.), and the like.

A molecular weight of the polymer is preferably 1,000 or more, more preferably 3,000 or more, and even more preferably 5,000 or more in terms of weight-average molecular weight (GPC, in terms of polystyrene). In addition, a molecular weight of the polymer is preferably 500,000 or less, more preferably 300,000 or less, and even more preferably 100,000 or less in terms of weight-average molecular weight (GPC, in terms of polystyrene).

A content of the polymer is preferably 50% by mass or less, more preferably 40% by mass or less, and even more preferably 30% by mass or less with respect to a total mass of the lens adhesive.

[(Meth)Acrylate Monomer]

The lens adhesive may include a (meth)acrylate monomer. The (meth)acrylate monomer may be a polyfunctional (meth)acrylate monomer having two or more (meth)acryloyl groups in a molecule, or may be a monofunctional (meth)acrylate monomer having one (meth)acryloyl group in a molecule.

Specific examples of (meth)acrylate monomers include a (meth)acrylate monomer described in paragraphs 0037 to 0046 of JP2012-107191A.

Examples of (meth)acrylate monomers that can be preferably used in the present invention include a monofunctional (meth)acrylate monomer having an aromatic ring such as a monomer 1 (phenoxyethyl acrylate) or a monomer 2 (benzyl acrylate); a (meth)acrylate monomer having an aliphatic group such as a monomer 3 (2-ethylhexyl acrylate), a monomer 4 (1,6-hexanediol dimethacrylate), or a monomer 5 (1,6-hexanediol dimethacrylate); and a (meth)acrylate monomer having a hydroxyl group such as a monomer 6 (2-hydroxyethyl acrylate), a monomer 7 (hydroxypropyl acrylate), or a monomer 8 (4-hydroxybutyl acrylate). A molecular weight of the (meth)acrylate monomer is preferably 100 to 500.

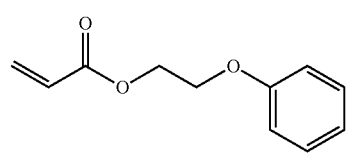

Monomer 1

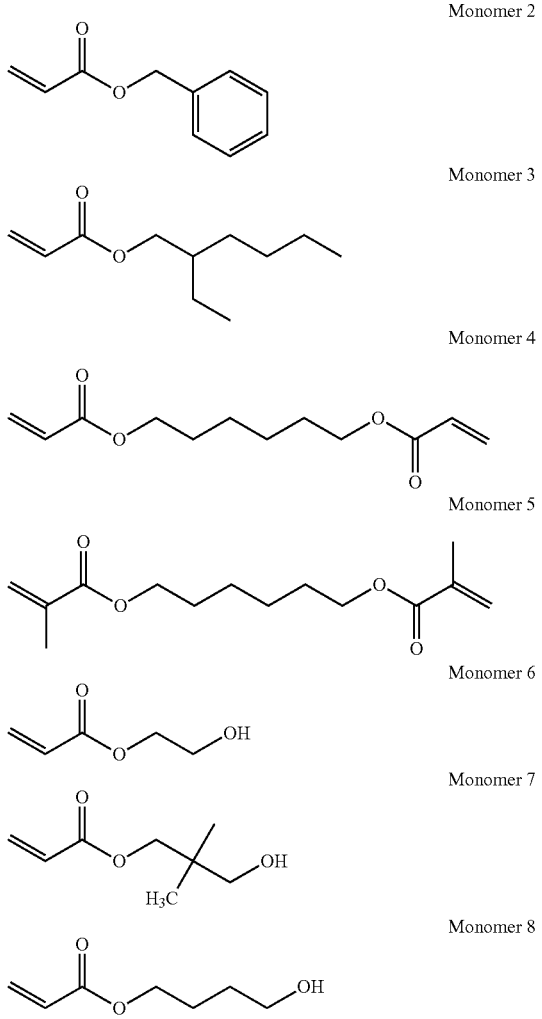

Monomer 2
Monomer 3
Monomer 4
Monomer 5
Monomer 6
Monomer 7
Monomer 8

A method of obtaining the (meth)acrylate monomer is not particularly limited, and the compound may be commercially available or may be produced by synthesis. In a case where the compound is commercially available, for example, it is possible to preferably use VISCOAT #192 PEA (monomer 1) (manufactured by OSAKA ORGANIC CHEMICAL INDUSTRY LTD.), VISCOAT #160 BZA (monomer 2) (manufactured by OSAKA ORGANIC CHEMICAL INDUSTRY LTD.), 2EHA (monomer 3) (manufactured by Toagosei Co., Ltd.), A-HD-N (monomer 4) (manufactured by Shin-Nakamura Chemical Co., Ltd.), HD-N (monomer 5) (manufactured by Shin-Nakamura Chemical Co., Ltd.), HEA (monomer 6) (manufactured by OSAKA ORGANIC CHEMICAL INDUSTRY LTD.), LIGHT ESTER HOP-A (N) (monomer 7) (manufactured by KYOEISHA CHEMICAL Co., LTD.), and 4-HBA (monomer 8) (manufactured by OSAKA ORGANIC CHEMICAL INDUSTRY LTD.).

In a case where the lens adhesive of the embodiment of the present invention contains a (meth)acrylate monomer, a content of the (meth)acrylate monomer is preferably 5% to 90% by mass, more preferably 10% to 85% by mass, and even more preferably 20% to 80% by mass, with respect to a total mass of the lens adhesive. By adjusting an amount of (meth)acrylate monomer in the lens adhesive, it is possible to adjust a function of relaxing stress when a cured material is deformed by heat.

[Polymerization Initiator]
<Photo-Radical Polymerization Initiator>

The lens adhesive preferably contains a photo-radical polymerization initiator. Specifically, the following compounds can be used as the photo-radical polymerization initiator. Examples of the photo-radical polymerization initiator include bis(2,6-dimethoxybenzoyl)-2,4,4-trimethylpentylphosphine oxide, bis(2,6-dimethylbenzoyl)-2,4,4-trimethylpentylphosphine oxide, bis(2,4,6-trimethylbenzoyl)-2,4,4-trimethylpentylphosphine oxide, bis(2,6-dichlorobenzoyl)-2,4,4-trimethylpentylphosphine oxide, 1-phenyl-2-hydroxy-2-methylpropan-1-one, 1-hydroxycyclohexyl phenyl ketone, 1-(4-isopropylphenyl)-2-hydroxy-2-methylpropan-1-one, 1,2-diphenylethanedione, methylphenyl glyoxylate, 1-[4-(2-hydroxyethoxy)-phenyl]-2-hydroxy-2-methyl-1-propan-1-one, 2-hydroxy-1-{4-[4-(2-hydroxy-2-methyl-propionyl)-benzyl]phenyl}-2-methyl-propan-1-one, 2,2-dimethoxy-1,2-diphenylethan-1-one, 2-methyl-1-(4-methylthiophenyl)-2-morpholinopropan-1-one, 2-benzyl-2-dimethylamino-1-(4-morpholinophenyl)-butanone-1,2,4,6-trimethylbenzoyl-diphenyl-phosphine oxide, and bis(2,4,6-trimethylbenzoyl)-phenylphosphine oxide.

Among the above examples, in the present invention, BASF's IRGACURE 184 (1-hydroxycyclohexyl phenyl ketone), IRGACURE 819 (bis(2,4,6-trimethylbenzoyl)-phenylphosphine oxide), IRGACURE 651 (2,2-dimethoxy-1,2-diphenylethane-1-one), 1-[4-(2-hydroxyethoxy)-phenyl]-2-hydroxy-2-methyl-1-propan-1-one, or 2-methyl-1-(4-methylthiophenyl)-2-morpholinopropan-1-one may be preferably used as the photo-radical polymerization initiator.

A content of the photo-radical polymerization initiator is preferably 0.01% to 5.0% by mass, more preferably 0.05% to 1.0% by mass, and even more preferably 0.05% to 0.5% by mass, with respect to a total mass of the lens adhesive.

(Thermal Radical Polymerization Initiator)

The lens adhesive may include a thermal radical polymerization initiator in addition to the photo-radical polymerization initiator. By further including a thermal radical polymerization initiator, it is possible to promote curing of a region where light does not reach.

Specifically, the following compounds can be used as the thermal radical polymerization initiator. Examples of thermal radical polymerization initiators include 1,1-di(t-hexylperoxy)cyclohexane, 1,1-di(t-butylperoxy)cyclohexane, 2,2-di(4,4-di-(t-butylperoxy)cyclohexyl)propane, t-hexylperoxyisopropyl monocarbonate, t-butylperoxy-3,5,5-trimethylhexanoate, t-butylperoxy laurate, dicumyl peroxide, di-t-butyl peroxide, t-butylperoxy-2-ethylhexanoate, t-hexylperoxy-2-ethylhexanoate, cumene hydroperoxide, t-butyl hydroperoxide, t-butylperoxy-2-ethylhexyl, 2,3-dimethyl-2,3-diphenylbutane, and the like.

In a case where the lens adhesive contains both photo-radical polymerization initiator and thermal radical polymerization initiator, a total content of the photo-radical polymerization initiator and the thermal radical polymerization initiator is preferably 0.01% to 5% by mass, more preferably 0.05% to 1.0% by mass, and even more preferably 0.05% to 0.5% by mass, with respect to a total mass of the lens adhesive.

<Cemented Lens>

A cemented lens can be produced by adhesion of two or more lenses using the lens adhesive of the embodiment of the present invention. For example, a lens A and a lens B are allowed to adhere using the lens adhesive of the embodiment of the present invention, and thereby a cemented lens including the lens A, an adhesive layer, and the lens B in this order can be produced.

The cemented lens produced using the lens adhesive of the embodiment of the present invention has a structure having the adhesive layer that absorbs ultraviolet light and has excellent fastness with respect to ultraviolet irradiation, and therefore it can be used as an optical lens having an ultraviolet cut function. In a device such as an imaging module in which this cemented lens is used, a component member including a resin cured material that is easily affected by ultraviolet rays is disposed on a side opposite to an incident side of external light with respect to the cemented lens, and thereby a deterioration due to light is prevented. In addition, even when the cemented lens itself has a lens made of a resin cured material, this lens is designed to be on the side opposite to the incident side of external light with respect to the adhesive layer at the time of use, and thereby high durability can be obtained.

The cemented lens can be obtained by superimposing two lenses using the lens adhesive of the embodiment of the present invention, and then curing the adhesive to form the adhesive layer as described later. The curing is preferably performed after removing air bubbles mixed into the adhesive after the superimposition.

[Adhesive Layer]

The adhesive layer is a layer obtained by curing the lens adhesive of the embodiment of the present invention. For example, in the production of the cemented lens, the adhesive layer is formed by applying the lens adhesive of the embodiment of the present invention to a surface of any one of the lenses to be cemented, superimposing the other lens, and then performing curing. The curing can be performed by performing at least light irradiation. In addition, a step of further heating may be performed after light irradiation.

As a light source used for light irradiation, a light source that emits light having a wavelength at which the photoradical polymerization initiator reacts can be optionally selected. For example, a halogen xenon lamp, a metal halide lamp, a low pressure mercury lamp, a high pressure mercury lamp, an ultrahigh pressure mercury lamp, a germicidal lamp, a xenon lamp, a light emitting diode (LED) light source lamp, or the like is suitably used. Selective irradiation of light having a narrow range of wavelengths may be performed using a laser. The atmosphere during photoirradiation is preferably air or an inert gas purged atmosphere and is more preferably an atmosphere purged with nitrogen until an oxygen concentration becomes 1% or less.

A heating temperature in a case of performing a heating step is 60° C. or higher, is preferably 70° C. to 200° C., more preferably 70° C. to 190° C., and even more preferably 80° C. to 180° C.

A thickness of the adhesive layer is preferably 10 to 50 μm, and more preferably 20 to μm. In a case where the thickness is 10 m or more, an effect of absorbing ultraviolet rays can be sufficiently obtained. In addition, in a case where the thickness is 50 μm or less, it is possible to improve transmittance in a short wavelength range (400 to 430 nm) of visible light while exhibiting high adhesiveness.

As will be described later in Examples, the adhesive layer formed from the lens adhesive containing the compound represented by General Formula 1 has high heat shock resistance. In the present specification, heat shock resistance refers to an ability to relax stress when the adhesive layer is deformed by heat.

A refractive index of the adhesive layer at a wavelength of 587 nm is preferably 1.51 or more, more preferably 1.53 or more, and even more preferably 1.55 or more. The reason for this is because a difference in refractive indices from a lens to be cemented becomes small.

In addition, a cut-off wavelength of the adhesive layer having a thickness of 30 μm is preferably 380 nm or less, more preferably 385 nm or less, and even more preferably 390 nm or less. A wavelength at which transmittance of the adhesive layer becomes 0.5% or less is defined as a cut-off wavelength. The transmittance of the adhesive layer can be measured using a spectrophotometer (for example, UV-2550 manufactured by Shimadzu Corporation).

In the lens adhesive of the embodiment of the present invention, a refractive index and a cut-off wavelength of the adhesive layer can be adjusted to the above ranges by adjusting an amount of the compound represented by General Formula 1.

[Lens A and Lens B]

The lens A and the lens B are lenses forming the cemented lens. In the present specification, in a case of using the cemented lens, a lens closer to the incident side of external light (an object (an object to be imaged) side) is referred to as the lens A, and a lens farther away therefrom is referred to as the lens B.

In the cemented lens including the lens A, the adhesive layer, and the lens B in this order, a material forming the lens A and the lens B is not particularly limited, but a case in which at least one of the lens A or the lens B is a glass lens is preferable, a case in which the lens A is a glass lens, and the lens B is a resin lens or a compound lens having a resin layer on the surface thereof is more preferable, and a case in which the lens A is a glass lens, and the lens B is a compound lens having a resin layer on the surface thereof is even more preferable.

When the lens B is a compound lens, it is preferable that the resin layer be in contact with the adhesive layer in the cemented lens. The reason for this is because, by employing a configuration in which the adhesive layer that is resin and the resin layer are in direct contact with each other, a difference in refractive indices between the layers can be minimized, and thereby interface reflection within the cemented lens can be reduced. Another reason for this is because, by providing the adhesive layer on the surface of the resin layer having a large surface roughness as compared with glass, surface unevenness of the resin layer is flattened, and thereby light scattering due to roughness of the surface of the resin layer can be prevented.

The type of lenses used as each of the lens A, the lens B, and a lens C to be described later is not particularly limited, and examples thereof include a disk-shaped convex lens, a concave lens, a meniscus lens, an aspheric lens, and a cylindrical lens having a cylindrical lens surface, a ball lens, a rod lens, and the like.

(Glass Lens)

Known glass lenses can be used without limitation. Examples of commercially available glass lenses include BK7 manufactured by OHARA INC.

When the compound lens includes a glass lens, the same glass lens can be used.

(Resin Lens and Compound Lens)

The resin lens refers to a lens made of a resin cured material.

In the present specification, the compound lens refers to a lens including a layer made of glass and a resin layer. The resin layer is a layer made of a resin cured material. Each layer included in the compound lens may be a lens (a single lens), and in this case, it is preferable that axes of each single lens (a line connecting the center of curvature of two spherical surfaces) coincide with each other. The compound lens may have a resin layer on the surface thereof or in the inside thereof, but the compound lens used as the lens B preferably has a resin layer on the surface thereof. A typical example of the compound lens used as the lens B is a compound lens in which a resin layer is formed on the surface of a glass lens.

In a case where the lens B is a resin lens or a compound lens, a resin cured material constituting the resin layer of the resin lens or the compound lens is not particularly limited, but a resin cured material having a small Abbe number is preferable. The resin cured material having a small Abbe number generally absorbs light in a ultraviolet light wavelength range on a long wavelength side (about 320 nm to 400 nm), and thus it is likely to deteriorate due to light. However, in the lens adhesive of the embodiment of the present invention, by controlling a structure of the compound contained therein, and a film thickness when the adhesive layer is formed, light can be absorbed up to the long wavelength side in the ultraviolet range, and therefore a deterioration due to light can be significantly inhibited. Specifically, an Abbe number of the resin cured material is preferably 30 or less, and more preferably 25 or less.

A partial dispersion ratio θg, F of the resin cured material constituting the resin lens or a resin layer of the compound lens constituting the lens B is preferably high. A partial dispersion ratio θg, F is not particularly limited, but it is preferably 0.65 or more, and more preferably 0.70 or more. In addition, a partial dispersion ratio θg, F is not particularly limited, but it is preferably 2 or less.

An Abbe number (νd) and a partial dispersion ratio (θg, F) of the resin cured material are values calculated by the following formulas.

$$\nu d=(nd-1)/(nF-nC)$$

$$\theta g,F=(ng-nF)/(nF-nC)$$

Where, nd represents a refractive index at a wavelength of 587.56 nm, nF represents a refractive index at a wavelength of 486.13 nm, nC represents a refractive index at a wavelength of 656.27 nm, and ng represents a refractive index at a wavelength of 435.83 nm.

An Abbe number of the resin cured material can be specifically obtained using a Kalnew precision refractometer, KPR-2000 (manufactured by Shimadzu Device Corporation) or an Abbe meter (manufactured by ATAGO CO., LTD.).

Examples of resins forming the resin cured material having an Abbe number of 30 or less include resins containing a structure of 9,9'-diarylfluorene, naphthalene, biphenyl, carbazole, benzothiazole, benzotriazole, and the like (specifically, for example, resins disclosed in JP1985-038411A (JP-S60-038411A), JP1998-067977A (JP-H10-067977A), JP2002-047335A, JP2004-083855A, JP2005-325331A, JP2007-238883A, JP2012-052016A, JP2012-001498A, JP2016-075911A, WO2006/095610A, JP1990-029401A (JP-H02-029401), and the like).

In addition, a cured material of a composition containing the compound represented by General Formula (A) is also preferably used.

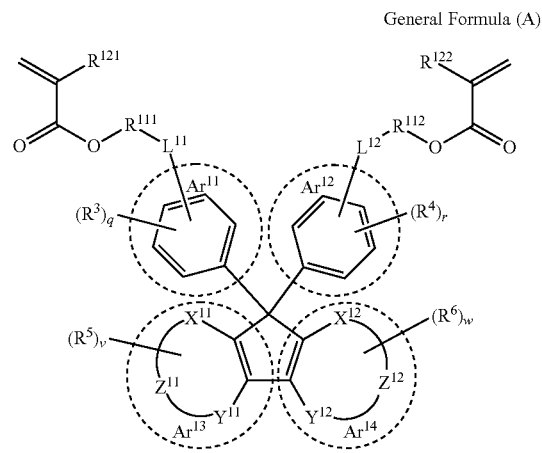

General Formula (A)

In General Formula (A), $Ar^{11}$ and $Ar^{12}$ each independently represent an aryl group containing a benzene ring surrounded by a broken line or a heteroaryl group containing a benzene ring surrounded by a broken line as one of rings constituting a fused ring, $X^{11}$, $Y^{11}$, $X^{12}$, and $Y^{12}$ each independently represent an oxygen atom, a sulfur atom, a nitrogen atom, or a carbon atom; $Z^{11}$ represents an atomic group which forms a 5- to 7-membered aromatic ring together with $X^{11}$—C=C—$Y^{11}$, and which contains at least one selected from an oxygen atom, a sulfur atom, a nitrogen atom, or a carbon atom; and Z represents an atomic group which forms a 5- to 7-membered aromatic ring together with $X^{12}$—C=C—$Y^{12}$, and which contains at least one selected from an oxygen atom, a sulfur atom, a nitrogen atom, or a carbon atom, $Ar^{13}$ and $Ar^{14}$ each independently represent an arylene group containing an aromatic ring surrounded by a broken line or a heteroarylene group containing an aromatic ring surrounded by a broken line, where at least one of $Ar^1$ or $Ar^1$ is a group other than a phenylene group, $R^3$ to $R^6$ each independently represent a substituent; q and r each independently are an integer of 0 to 4; v is an integer of 0 or more, where a maximum number of v is a maximum number of substituents capable of being substituted on the ring formed by $X^{11}$—C=C—$Y^{11}$ and $Z^{11}$; and w is an integer of 0 or more, where a maximum number of w is a maximum number of substituents capable of being substituted on the ring formed by $X^{12}$—C=C—$Y^{12}$ and $Z^{12}$, $L^{11}$ and $L^{12}$ each independently represent a single bond, an oxygen atom, a sulfur atom, or an ester bond, $R^{111}$ and $R^{112}$ each independently represent a single bond or a divalent linking group, $R^{121}$ and $R^{122}$ each independently represent a hydrogen atom or a methyl group, and in a case where $Ar^{11}$ to $Ar^{14}$ each independently are a fused ring group containing an aromatic ring surrounded by a broken line as one of rings constituting a fused ring, a group having $L^{11}$ as a linking group, a group having $L^{12}$ as a linking group, and $R^3$ to $R^6$ each independently may be substituted on an aromatic ring surrounded by a broken line, or may be substituted on a ring constituting the fused ring other than the aromatic ring surrounded by the broken line.

In General Formula (A), the substituents represented by $R^3$ to $R^6$ are not particularly limited, and examples thereof include a halogen atom, a halogenated alkyl group, an alkyl group, an alkenyl group, an acyl group, a hydroxyl group, a hydroxyalkyl group, an alkoxy group, an aryl group, a heteroaryl group, an aliphatic cyclic group, a cyano group, and the like.

In General Formula (A), the divalent linking group represented by each of $R^{111}$ and $R^{112}$ includes a linking group having at least one selected from an ether bond, an ester bond, a thioether bond, a thioester bond, an amide bond, a carbonate bond, and an alkylene group. The alkylene group is also preferably a branched alkylene group in which one or more alkyl groups are substituted in a linear alkylene group.

Specific examples of respective partial structures in a case where the compound represented by General Formula (A) is divided into partial structures A to D as follows, and specific examples of compounds represented by General Formula (A) as a combination of the respective partial structures are shown below. However, the compound represented by General Formula (A) and the respective partial structures are not limited to the following examples. The letter "Me" in the following structural formulas represents a methyl group.

General Formula (A)

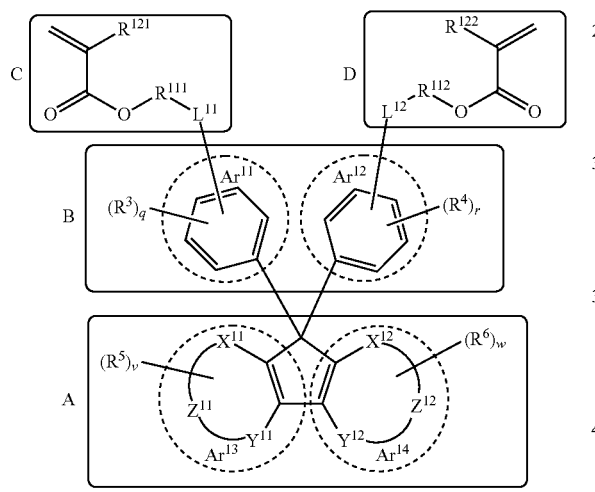

(Specific Examples of Partial Structure A)

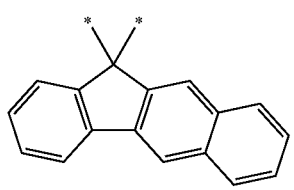
(A-1)

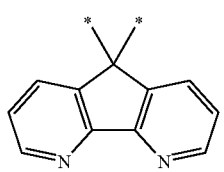
(A-2)

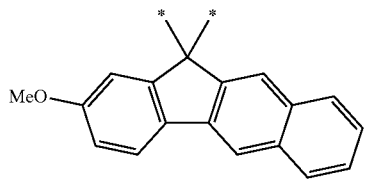
(A-3)

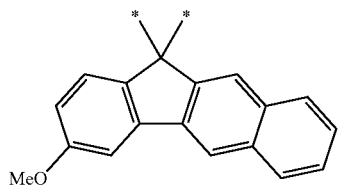
(A-4)

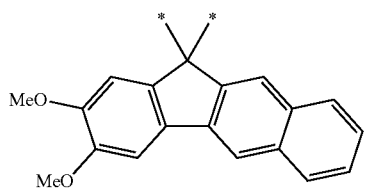
(A-5)

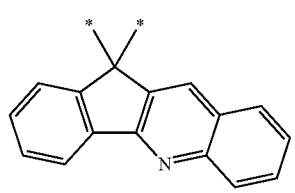
(A-6)

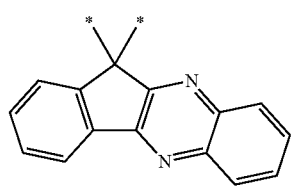
(A-7)

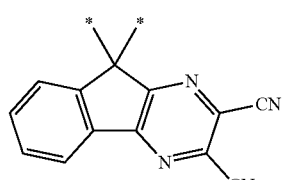
(A-8)

The symbol * indicates a binding position with the partial structure B.

Among them, A-1, A-3, A-4, A-5, A-6, and A-7 are preferable, A-1, A-5, and A-7 are more preferable, and A-5 and A-7 are particularly preferable.

(Specific Examples of Partial Structure B)

Hereinafter, a structure in which any two combinations selected from the group consisting of B-1, B-2, B-3, B-4, and B-5 are used as $Ar^{11}$ and $Ar^{12}$ will be exemplified.

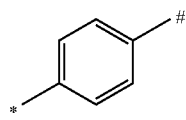
(B-1)

-continued (B-2)

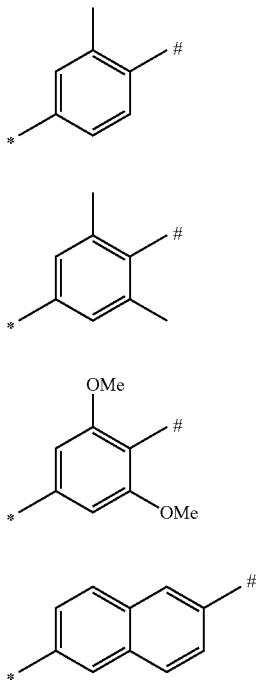

(B-3)

(B-4)

(B-5)

The symbol * indicates a binding position with the partial structure A, and the symbol # indicates a binding position with the partial structure C or D.

It is preferable that both $Ar^{11}$ and $Ar^{12}$ be B-1, both $Ar^{11}$ and $Ar^{12}$ be B-2, both $Ar^{11}$ and $Ar^{12}$ be B-3, or both $Ar^{11}$ and $Ar^{12}$ be B-4, and it is more preferable that both $Ar^{11}$ and $Ar^{12}$ be B-1, both $Ar^{11}$ and $Ar^{12}$ be B-2, or both $Ar^{11}$ and $Ar^{12}$ be B-3.

(Specific Examples of Partial Structures C and D)

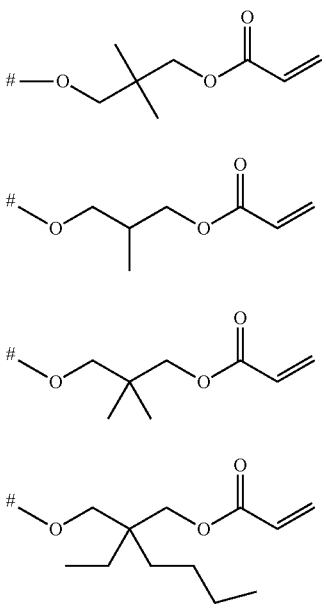

(C-1)

(C-2)

(C-3)

(C-4)

-continued

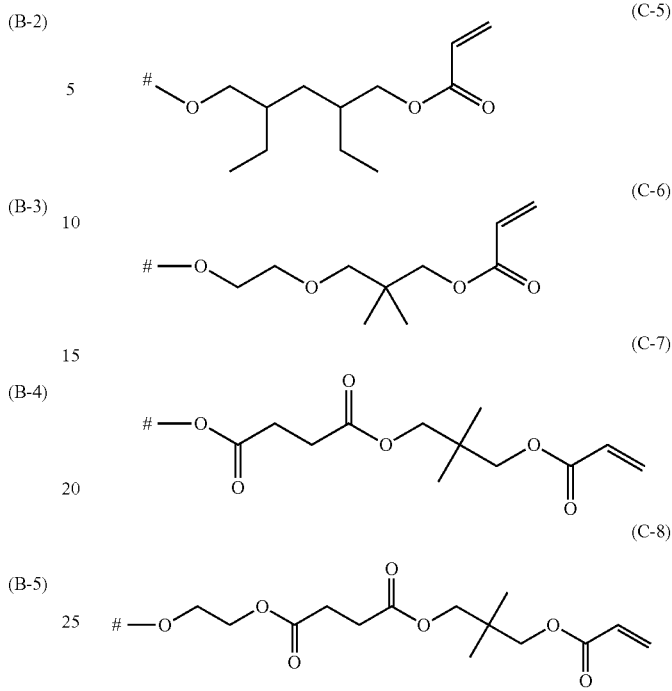

(C-5)

(C-6)

(C-7)

(C-8)

The symbol # indicates a binding position with the partial structure B.

Among the above structures, the partial structure C-1, C-7, or C-8 is preferable. The reason for this is because the compound represented by General Formula (A) becomes a mixture of structural isomers by the partial structure C-1, C-7, or C-8, and a content of the compound represented by General Formula (A) in a curable composition can then be made larger. In addition, stability after long-term storage can be improved.

<Device: Imaging Module>

The lens adhesive of the embodiment of the present invention is used in a device including an optical lens therein, and can prevent a deterioration due to light in the optical lens, and eventually in the device. Specifically, in a device to which a resin lens or a compound lens including a resin layer is attached, it is possible to prevent a deterioration due to light in the resin lens or the compound lens by disposing the adhesive layer formed from the lens adhesive of the embodiment of the present invention in a direction in which external light is incident on the resin lens or the compound lens of a housing (having a light shielding property). The adhesive layer can be provided, for example, as a part of the above-described cemented lens.

Examples of devices that use the lens adhesive of the embodiment of the present invention and include an optical lens therein include an imaging module that images an object with a lens optical system to form an image. Examples of targets to which the imaging module can be adopted include electronic devices such as a digital camera, a PC camera built in or externally attached to Personal Computer (PC), an interphone attached with a camera, a vehicle-mounted camera, an endoscope, and a portable terminal device having a imaging function. Examples of portable terminal devices include a mobile phone or a smartphone, a Personal Digital Assistants (PDA), a portable game machine, and the like.

FIG. 1 shows an example of the above-mentioned lens optical system including an adhesive layer formed from the lens adhesive of the embodiment of the present invention. A lens A (3), an adhesive layer (1), a lens B (4), and a lens C (5) are disposed in this order from an object (an object to be imaged) side (7) toward an image-formed surface side (8), and a cemented lens (2) consists of the lens A, the adhesive layer, and the lens B. A deterioration due to light can be prevented in a resin lens or a compound lens disposed as the lens B or the lens C on the image-formed surface side of the adhesive layer. In FIG. 1, each of the lens B and the lens C is a compound lens. In addition to the lens optical system shown in FIG. 1, it is possible to prevent a deterioration due to light in constituent lenses in, for example, the following lens optical systems:

(1) lens optical system which consists of only a cemented lens of the lens A that is a glass lens and the lens B that is a compound lens, and which does not have the lens C;

(2) lens optical system in which the lens A and the lens B are glass lenses and the lens C is a compound lens or a resin lens; and (3) lens optical system including one or more additional lenses in addition to the optical system of (1) or (2).

[Lens C]

As described above, the lens optical system in the imaging module including the adhesive layer formed from the lens adhesive of the embodiment of the present invention may include the lens C. In the present specification, the "lens C" refers to lenses other than a cemented lens, in which lenses are allowed to adhere to each other by the lens adhesive of the embodiment of the present invention, and lenses constituting the cemented lens, and refers to lenses disposed at a position farther away from an incident side of external light (an object (an object to be imaged) side) than the cemented lens including an adhesive layer formed from the lens adhesive of the embodiment of the present invention.

A material forming the lens C is not particularly limited, but the lens C is preferably a resin lens or a compound lens. The reason for this is because, when the lens C is a resin lens or a compound lens, an effect of inhibiting a deterioration due to light by absorption of ultraviolet rays in the cemented lens including the adhesive layer formed from the lens adhesive of the embodiment of the present invention is particularly enhanced.

The compound lens used as the lens C may have a resin layer on the surface thereof or in the inside thereof.

Preferable ranges and examples of resin layers of a resin lens or compound lens constituting the lens C are the same as those described above for the resin layer of a resin lens or compound lens constituting the lens B.

EXAMPLES

Hereinafter, the features of the present invention will be more specifically described with reference to Examples and Comparative Examples. In the following Examples, the materials to be used, amounts and ratios thereof, the details of the treatment and the treatment procedures, and the like may be suitably modified or changed without departing from the scope of the present invention. Accordingly, the scope of the present invention should not be limitedly interpreted by the following specific Examples.

Synthesis Example 1

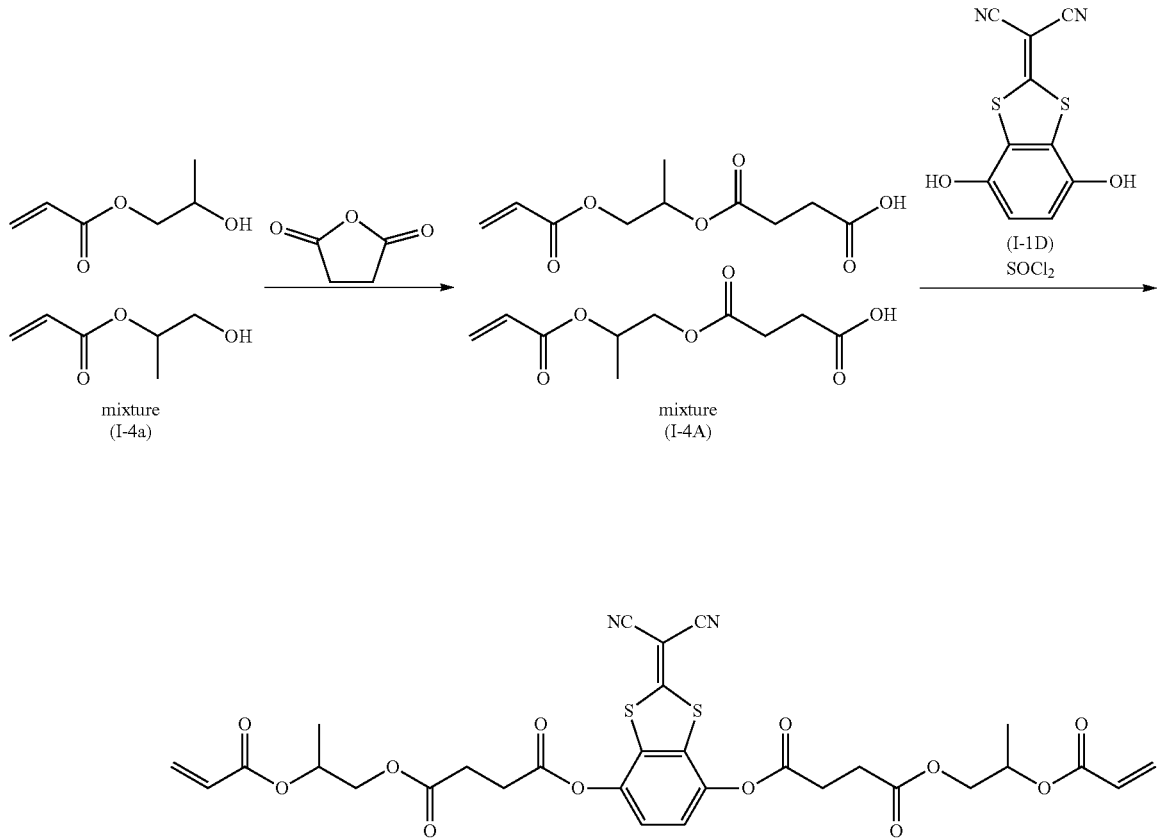

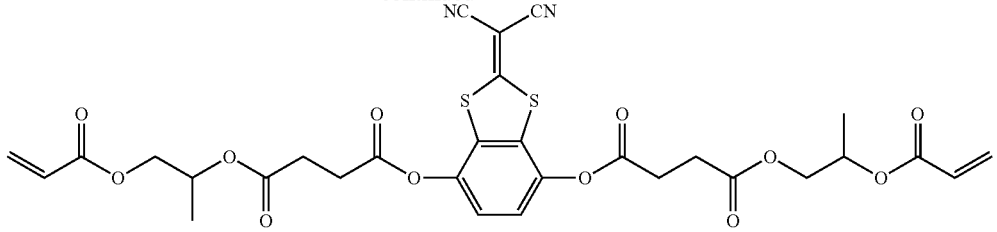

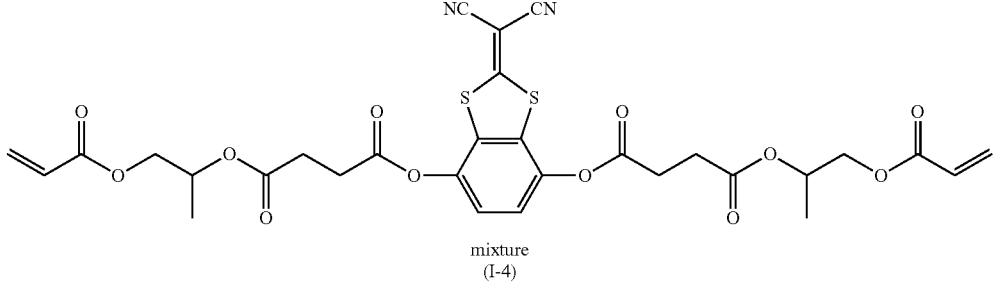

mixture
(I-4)

[Synthesis of Compound (I-1D)]

Synthesis of a compound (I-1D) was performed according to a method described in "Journal of Chemical Crystallography" (1997); 27 (9); p. 515-526.

[Synthesis of Compound (I-4A)]

A compound (I-4A) was synthesized according to a method for synthesizing a compound (I-4A) described in JP2016-081035A.

[Synthesis of Compound (I-4)]

15.5 g (67.4 mmol) of a carboxylic acid compound (I-4A), 185 mL of ethyl acetate, 46 mL of N,N-dimethylacetamide, and 60 mg of 2,6-di-t-butyl-4-methylphenol were mixed, and an internal temperature was cooled to 0° C. To the mixture, 7.75 g (65.1 mmol) of thionyl chloride was added dropwise at an internal temperature of 0° C. to 5° C. After stirring at 5° C. for 60 minutes, a solution of 6.85 g (27.6 mmol) of the compound (I-1D) and 52 mL of tetrahydrofuran (THF) was added dropwise at an internal temperature of 0° C. to 8° C.

Thereafter, 16.8 g of N,N-diisopropylethylamine was added dropwise at an internal temperature of 0° C. to 10° C. After stirring at an internal temperature of 20° C. to 25° C. for 1 hour, 40 mL of ethyl acetate, 165 mL of water, and 14 mL of concentrated hydrochloric acid were added and washed. The organic layer was washed with 140 mL of saturated saline and separated, and then washed with 100 mL of saturated saline and 10 mL of an aqueous solution of 7.5% by mass sodium bicarbonate to be separated. Thereafter, concentration was performed to obtain an oily composition, which was then purified by column chromatography, and thereby a compound (I-4) (yield 85%) was obtained.

$^1$H-NMR (400 MHz, CDCl$_3$): δ (ppm) 1.25-1.35 (d, 6H), 2.78 (t, 4H), 2.95 (t, 4H), 4.10-4.35 (m, 4H), 5.25 (sext, 2H), 5.83 (d, 2H), 6.05-6.15 (m, 2H), 6.40 (d, 2H), 7.33 (s, 2H)

Synthesis Example 2

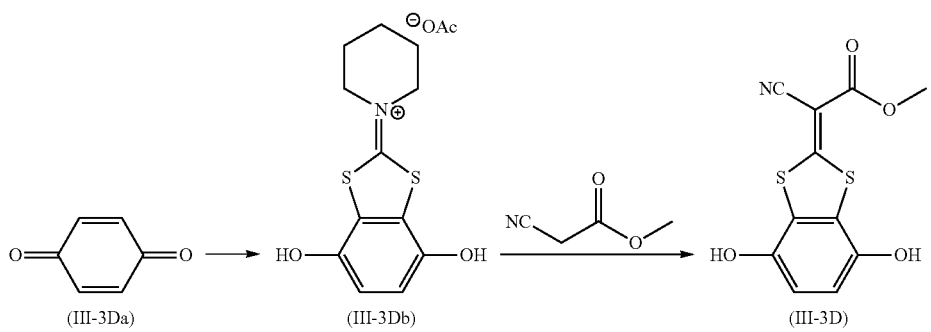

-continued
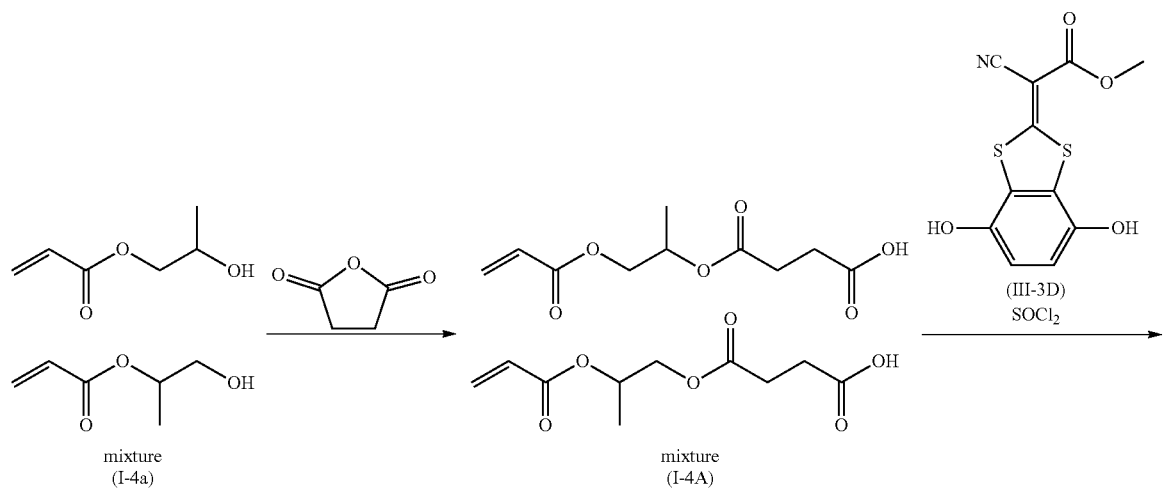
mixture (I-4a) → mixture (I-4A)
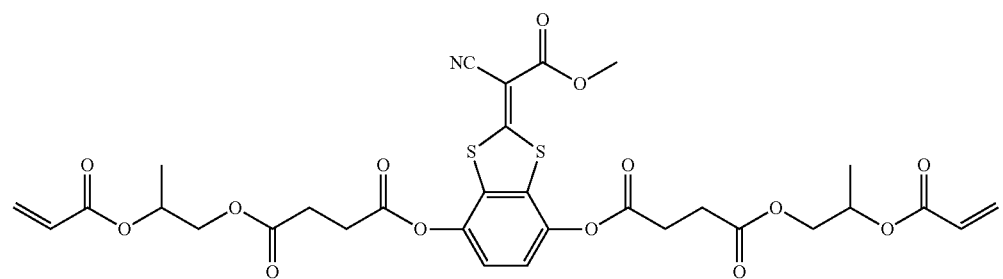
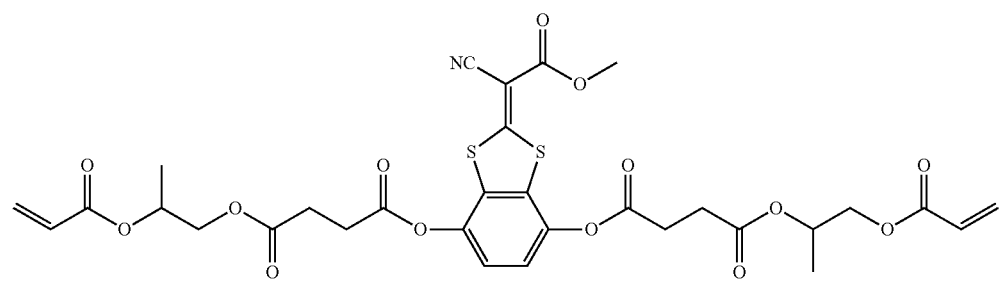
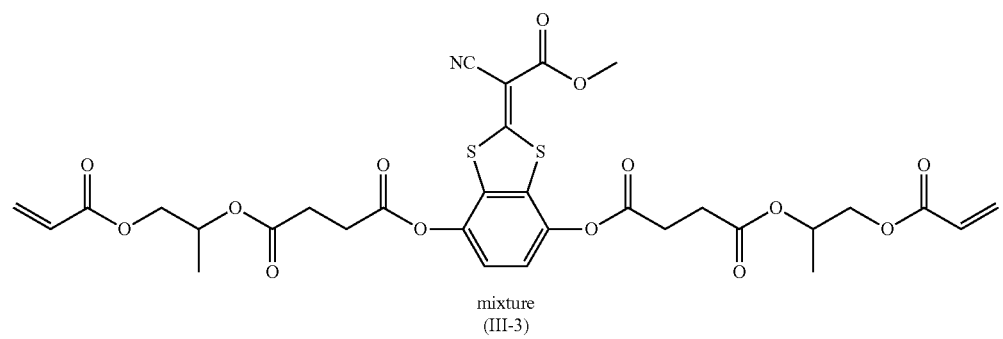
mixture (III-3)

[Synthesis of Compound (III-3Db)]

Synthesis of a compound (III-3Db) was performed according to a method described in "Journal of Organic Chemistry" (2004); 69 (6); p. 2164-2177.

[Synthesis of Compound (III-3D)]

5.0 g (15.3 mmol) of the compound (III-3Db), 1.66 g (16.80 mmol) of methyl cyanoacetate, and 25 mL of isopropyl alcohol were mixed and stirred for 3 hours under heating to reflux. Thereafter, the mixture was cooled to room temperature, 50 mL of water was added to the mixture, and the precipitated crystals were filtered. The obtained crystals were washed with a mixed solution of water-isopropyl alcohol (10 to 1) and a 0.5N hydrochloric acid solution, then dissolved in N,N-dimethylacetamide and filtered. Water was added to the obtained filtrate, the precipitated crystals were filtered, and thereby 2.2 g (7.82 mmol) of a compound (III-3D) (yield 51%) was obtained.

[Synthesis of Compound (III-3)]

A compound (III-3) (yield 86%) was obtained in the same manner as in Synthesis Example 1, except that the compound (I-1D) in the synthesis method of the compound (I-4) described in Synthesis Example 1 was changed to the compound (III-3D).

$^1$H-NMR (400 MHz, CDCl$_3$): δ (ppm) 1.25-1.35 (d, 6H), 2.78 (t, 4H), 2.95 (t, 4H), 3.89 (s, 3H), 4.10-4.35 (m, 4H), 5.25 (sext, 2H), 5.83 (d, 2H), 6.05-6.15 (m, 2H), 6.40 (d, 2H), 7.28 (s, 2H)

Synthesis Example 3

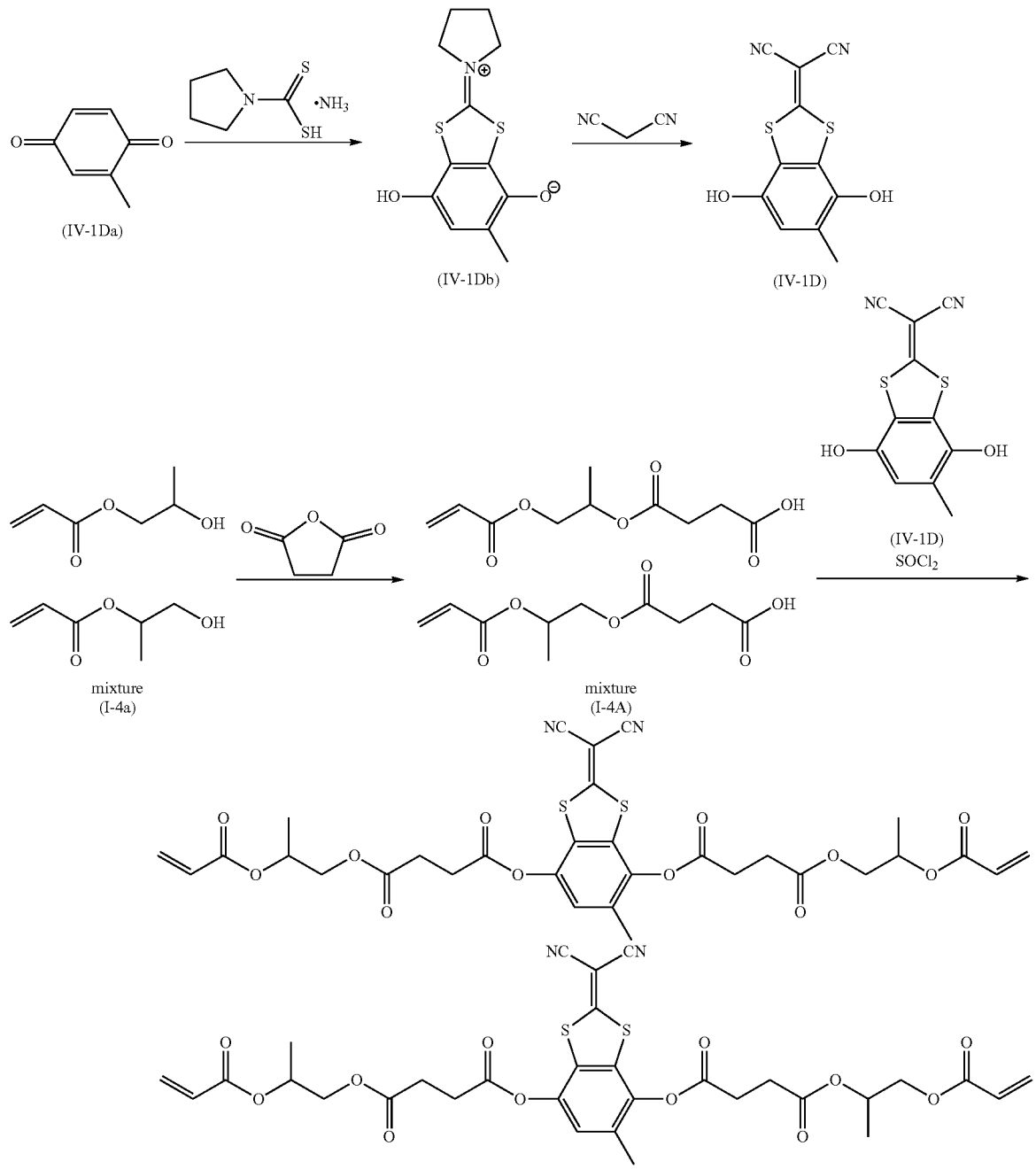

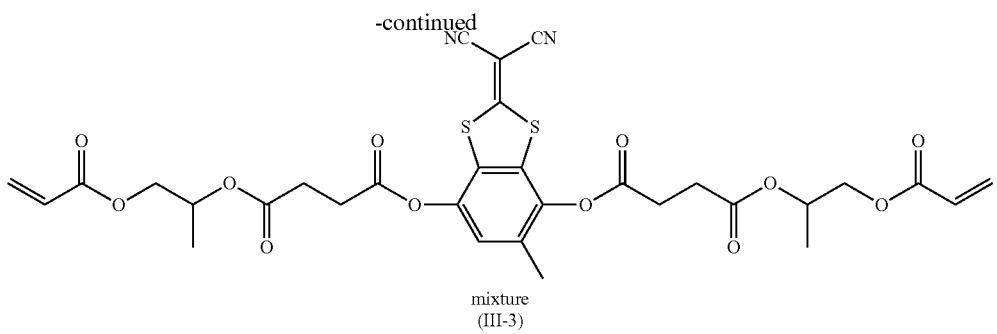

mixture
(III-3)

[Synthesis of Compound IV-1Db]

8.2 g (50.0 mmol) of 1-ammonium pyrrolidinecarbodithioate and 50 mL of N,N-dimethylformamide were mixed and cooled to 5° C. To the mixture, a solution of 6.7 g (55.0 mmol) of tolquinone (IV-1Da) in 40 mL of acetic acid was added dropwise and stirred at room temperature for 2 hours. Thereafter, the internal temperature was cooled to 5° C., and a solution of 5.9 g (55.0 mmol) of 1,4-benzoquinone in 40 mL of dimethyl sulfoxide was slowly added dropwise so that the internal temperature did not exceed 15° C. After stirring at room temperature for 1 hour, 1 L of water was added. To the mixture, 28% by mass aqueous sodium hydroxide solution was added until crystals were precipitated, the precipitated crystals were filtered and washed with water and methanol, and thereby 5.4 g (20.1 mmol) of a compound (IV-1Db) (yield 40%) was obtained.

[Synthesis of Compound IV-1D]

1.5 g (5.6 mmol) of the compound (IV-1Db), 410 mg (6.2 mmol) of malononitrile, 16 mL of isopropyl alcohol, 0.3 mL of acetic acid, and 0.2 mL of acetic anhydride were mixed, and the mixture was stirred with heating under reflux for 3 hours. Thereafter, the mixture was cooled to room temperature, water was added to the mixture, and the precipitated crystals were filtered, and thereby 1.1 g (4.2 mmol) of a compound (IV-1D) (yield 75%) was obtained.

[Synthesis of Compound IV-1]

A compound (IV-1) (yield 80%) was obtained in the same manner as in Synthesis Example 1, except that the compound (I-1D) in the synthesis method of the compound (I-4) described in Synthesis Example 1 was changed to the compound (IV-1D).

$^1$H-NMR (400 MHz, CDCl$_3$): δ (ppm) 1.25-1.35 (d, 6H), 2.78 (m, 4H), 2.95 (m, 4H), 4.10-4.35 (m, 4H), 5.24 (sext, 2H), 5.83 (d, 2H), 6.05-6.15 (m, 2H), 6.40 (d, 2H), 7.20 (s, 2H)

Synthesis Example 4

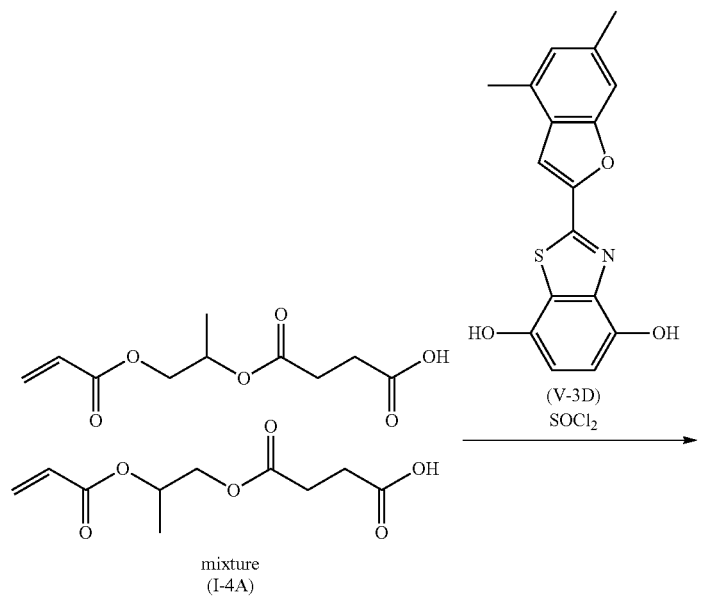

mixture
(I-4A)

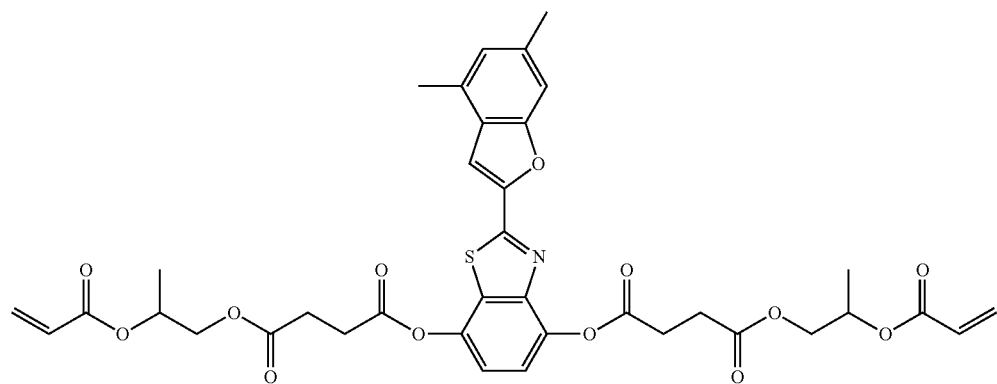
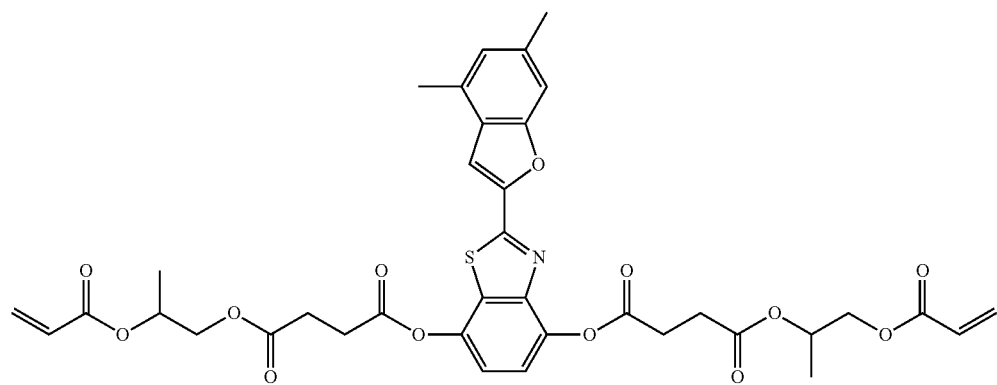
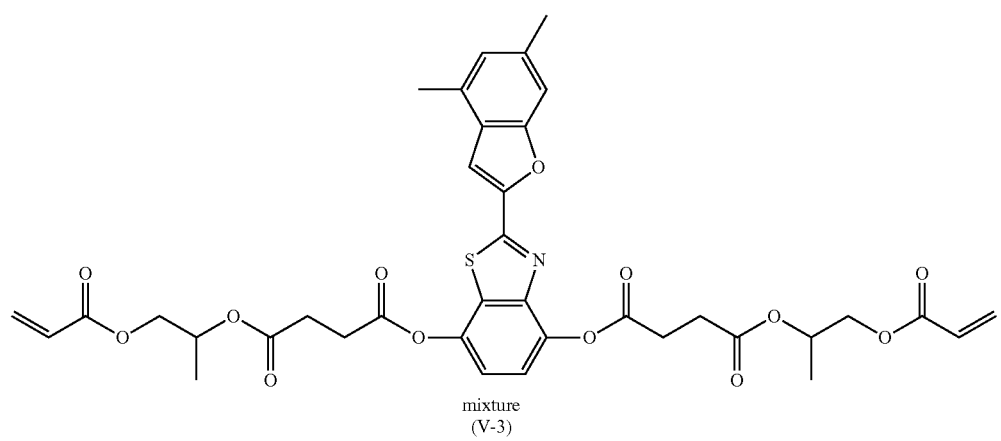
mixture
(V-3)

[Synthesis of V-3D]

A compound (V-3D) was synthesized with reference to a method for synthesizing a compound (11-d) described in paragraph 0282 of JP2013-071956A.

[Synthesis of Compound (V-3)]

A compound (V-3) (yield 82%) was obtained in the same manner as in Synthesis Example 1, except that the compound (I-1D) in the synthesis method of the compound (I-4) described in Synthesis Example 1 was changed to the compound (V-3D).

$^1$H-NMR (400 MHz, DMSO-d6): δ (ppm) 1.25-1.35 (d, 6H), 2.78 (t, 4H), 2.95 (t, 4H), 4.10-4.35 (m, 4H), 5.25 (sext, 2H), 5.83 (d, 2H), 6.05-6.15 (m, 2H), 6.40 (d, 2H), 7.03 (s, 1H), 7.35-7.45 (m, 3H) 7.80 (s, 1H)

Synthesis Example 5

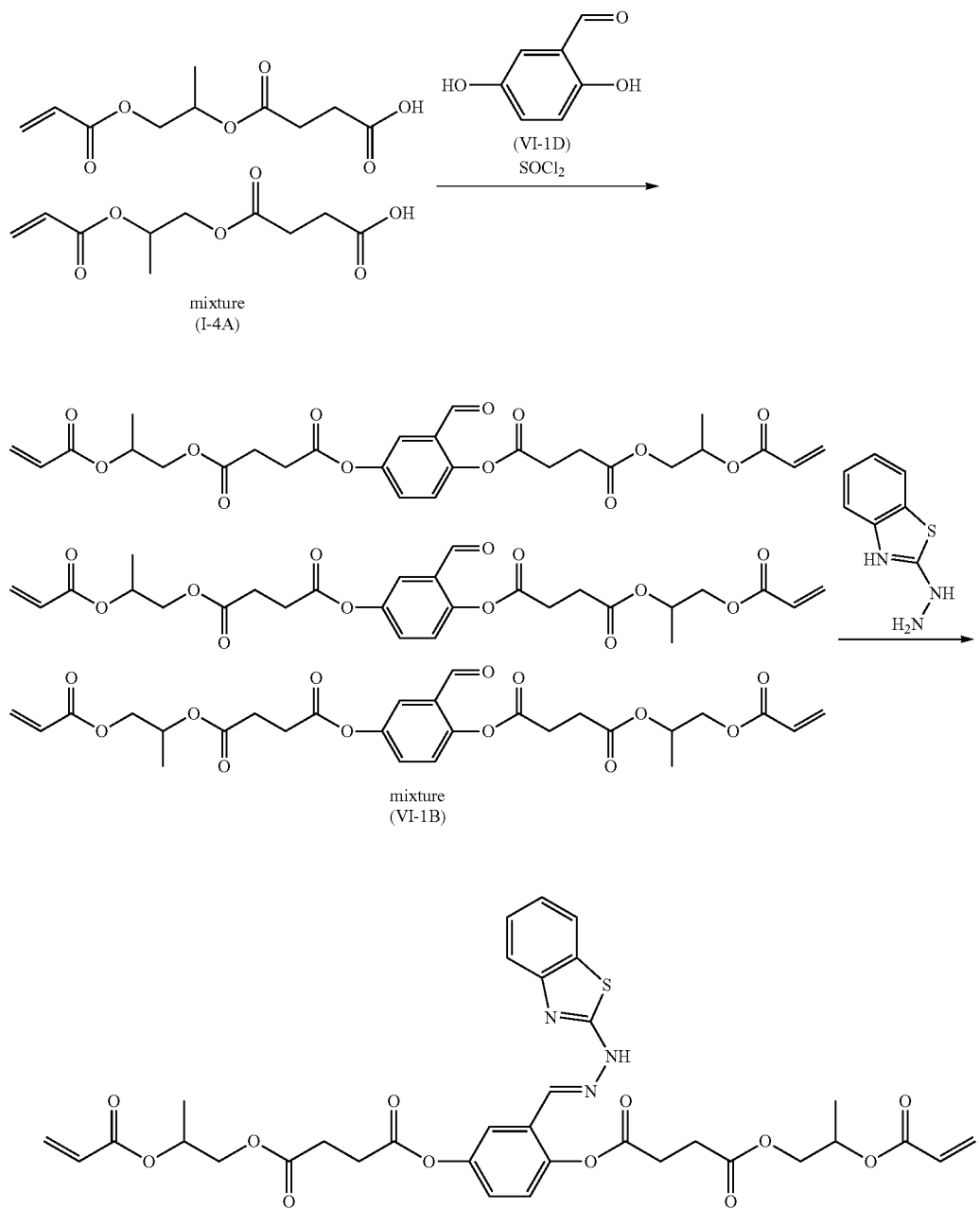

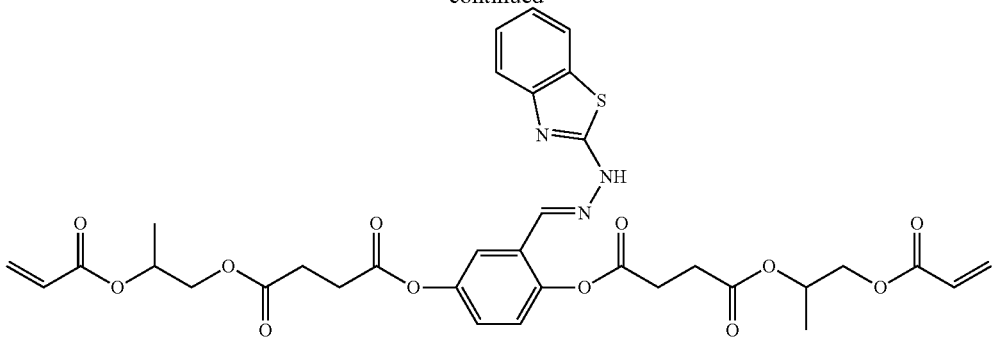

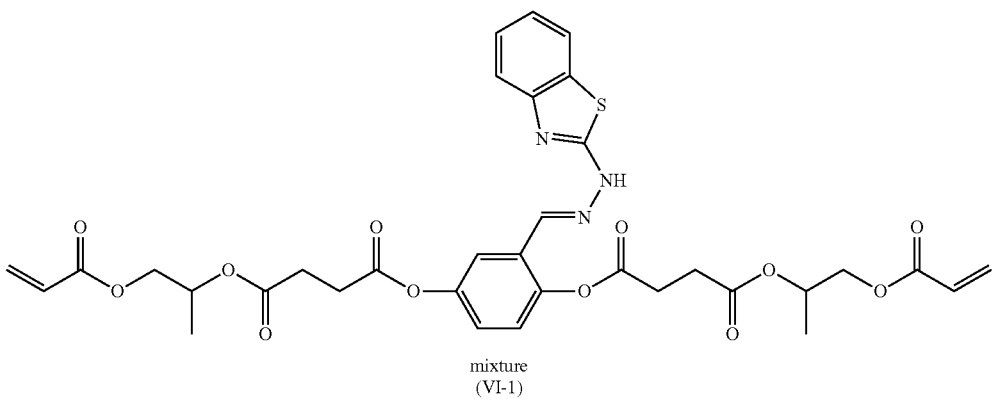

mixture
(VI-1)

[Synthesis of Compound (VI-1B)]

A compound (VI-1B) (yield 74%) was obtained in the same manner as in Synthesis Example 1, except that the compound (I-1D) in the synthesis method of the compound (I-4) described in Synthesis Example 1 was changed to 2,5-dihydroxybenzaldehyde (VI-1D).

[Synthesis of Compound (VI-1)]

0.26 g (0.46 mmol) of the compound (VI-1B), 99 mg (0.60 mmol) of 2-hydrazinobenzothiazole, 5.4 mg (0.01 mmol) of 10-camphorsulfonic acid, and 10 mL of tetrahydrofuran were mixed and stirred at room temperature for 12 hours. Ethyl acetate and water were added to the mixture for liquid separation, and the collected organic layer was washed with 1 N hydrochloric acid and saturated saline, and then dried over anhydrous sodium sulfate. Sodium sulfate was removed by filtration, the solvent was removed with a rotary evaporator, and purification was performed by silica gel chromatography, and thereby 0.22 g (0.31 mmol) of a compound (VI-1) (yield 67%) was obtained.

$^1$H-NMR (400 MHz, CDCl$_3$) δ (ppm): 1.25-1.35 (d, 6H), 2.78 (t, 4H), 2.85 (t, 4H), 4.10-4.35 (m, 2H), 5.25 (sext, 2H), 7.30 (d, 4H), 7.47 (br s, 1H), 7.60 (d, 1H), 7.80 (br d, 1H), 8.09 (s, 1H), 12.5 (br s, 1H)

Synthesis Example 6

[Synthesis of Compound (II-2)]

A compound (II-2) was synthesized according to a synthesis method of Example 4 described in JP2016-081035A.

Synthesis Example 7

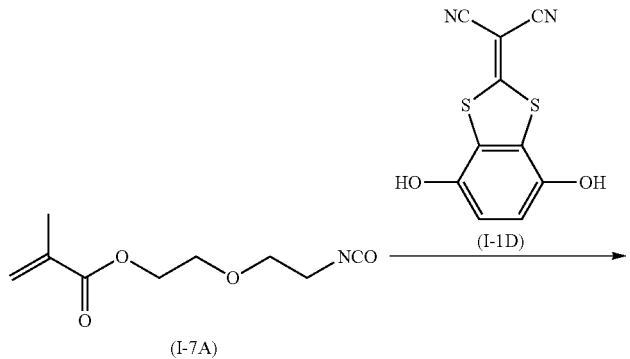

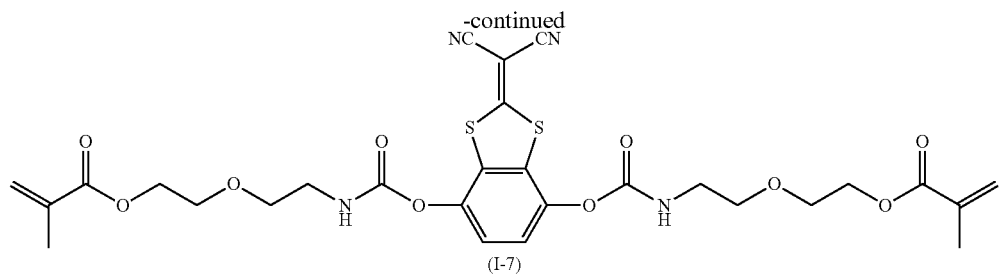
(I-7)

[Synthesis of Compound (I-7)]

3.9 g (19.5 mmol) of Karenz MOI-EG (I-7A, manufactured by Showa Denko K. K.), 2.7 g (10.9 mmol) of the compound (I-1D), 2 mL of N,N-dimethylacetamide, and 20 mL of chloroform were mixed, and the internal temperature was heated to 60° C. After stirring for 12 hours, the mixture was cooled to room temperature and further stirred for 12 hours. Next, after adding a saturated aqueous solution of sodium bicarbonate and stirring for 1 hour, liquid separation was performed. The collected organic layer was washed with 1 N hydrochloric acid and saturated saline, and then dried over anhydrous sodium sulfate, the solvent was removed with a rotary evaporator, and purification was performed by silica gel chromatography, and thereby 5.7 g (8.90 mmol) of a compound (I-7) (yield 82%) was obtained.

$^1$H-NMR (400 MHz, CDCl$_3$): δ (ppm) 1.95 (s, 6H), 3.37 (m, 4H), 3.60-3.70 (m, 8H), 4.20 (t, 4H), 5.15 (br, s, 2H), 5.58 (s, 2H), 6.13 (s, 2H), 7.32 (s, 2H)

Synthesis Example 8

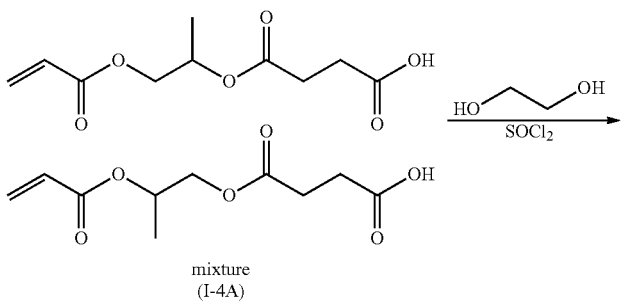
mixture
(I-4A)

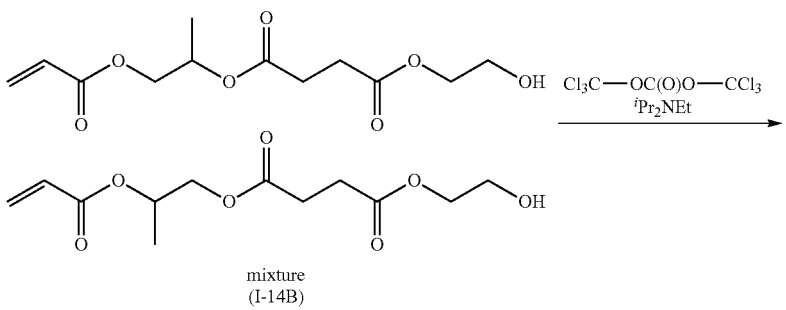
mixture
(I-14B)

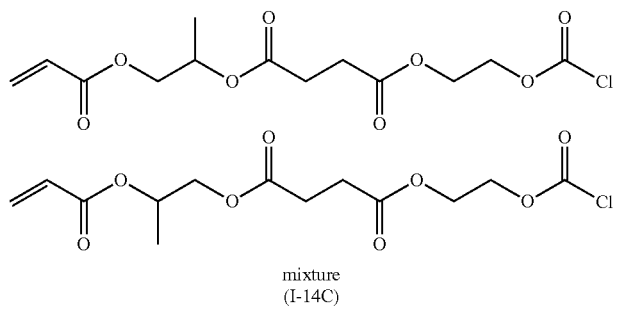
mixture
(I-14C)

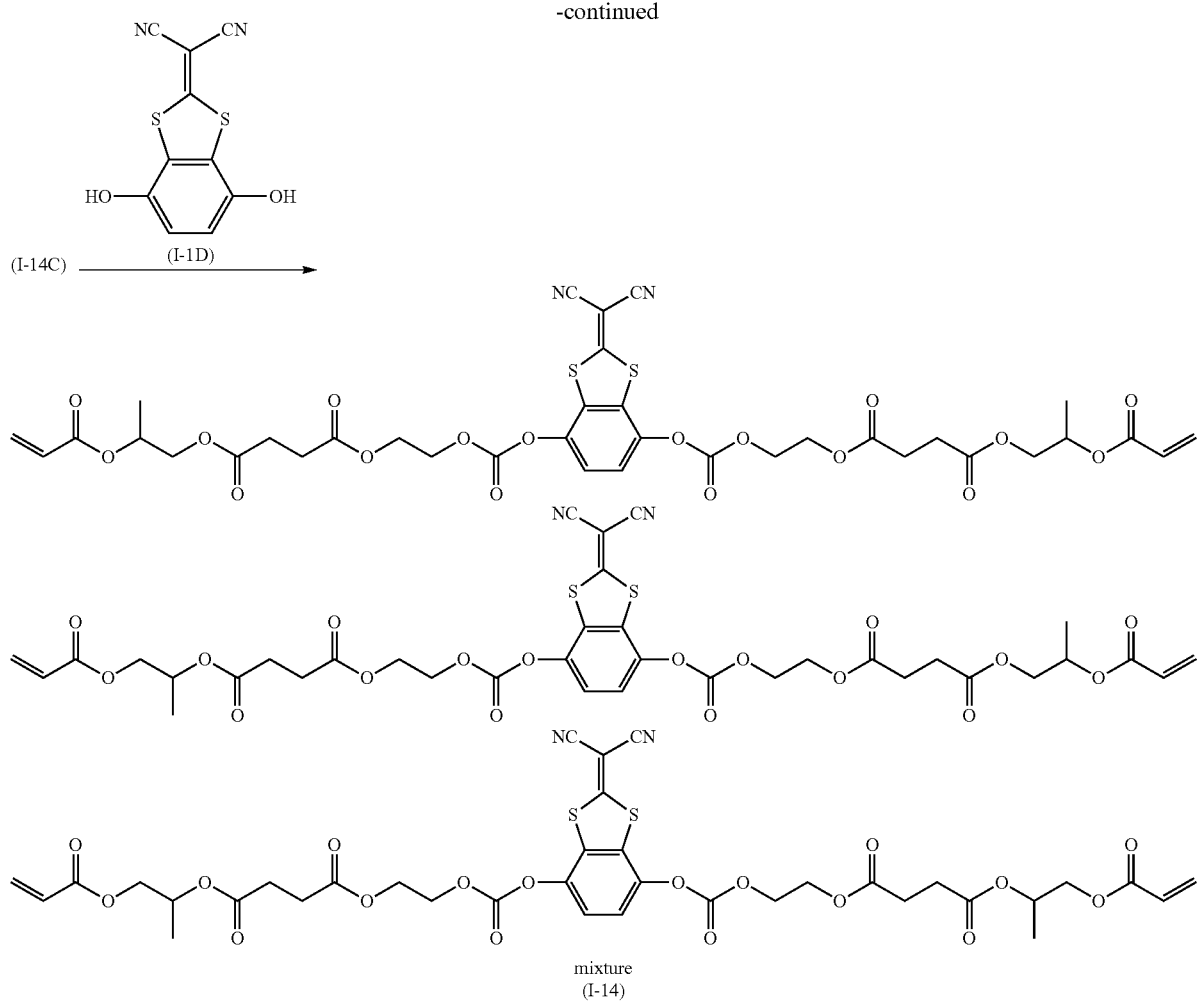

mixture (I-14)

[Synthesis of Compound (I-14B)]

8.00 g (29.2 mmol) of the carboxylic acid compound (I-4A), 28 mL of THF, 7 mL of N,N-dimethylacetamide, and 60 mg of 2,6-di-t-butyl-4-methylphenol were mixed, and an internal temperature was cooled to 0° C. To the mixture, 4.00 g (33.6 mmol) of thionyl chloride was added dropwise at an internal temperature of 0° C. to 5° C., and the mixture was stirred at 5° C. for 60 minutes. To the obtained mixture, a solution of 10.3 g (166 mmol) of ethylene glycol and 20 mL of THF was added dropwise at an internal temperature of 0° C. to 8° C., and then stirred at an internal temperature of 20° C. to 25° C. for 8 hours.

Thereafter, the reaction solution to which 100 mL of ethyl acetate was added was washed with 100 mL of 1 N hydrochloric acid and 30 mL of 7% by mass aqueous sodium carbonate solution and separated. Thereafter, concentration was performed to obtain an oily composition, which was then purified by column chromatography, and thereby 5.8 g of a compound (I-14B) (yield 72%) was obtained.

[Synthesis of Compound (I-14C)]

A mixed solution of 1.83 g (6.19 mmol) of triphosgene, 22.5 mL of ethyl acetate, 4.90 g of the compound (I-14B), 2.9 g (19.6 mmol) of N,N-diisopropylethylamine and 11 mL of ethyl acetate was added dropwise at 25° C. to 30° C. After stirring for 2 hours, the mixture was cooled to 0° C., washed with 17 mL of 2 N hydrochloric acid and 17 mL of saturated saline, and separated. After drying with anhydrous sodium sulfate, the solvent was removed with a rotary evaporator, and thereby 5.4 g of a compound (I-14C) which is a transparent oil (yield 90%) was obtained.

[Synthesis of Compound (I-14)]

6.75 g of the chlorocarbonic acid ester compound (I-14C) (purity 88.4%), 50 mL of ethyl acetate, 12.5 mL of N,N-dimethylacetamide, and 55 mg of 2,6-di-t-butyl-4-methylphenol were mixed, and the internal temperature was cooled to 0° C. To the mixture, 1.87 g of the compound (I-1D) and a solution of 25 mL of TH were added dropwise at an internal temperature of 0° C. to 8° C.

Thereafter, 4.60 g of N,N-diisopropylethylamine was added dropwise at an internal temperature of 0° C. to 10° C. After stirring at an internal temperature of 20° C. to 25° C. for 1 hour, 10 mL of ethyl acetate, 45 mL of water, and 4.5 mL of concentrated hydrochloric acid were added and washed. The organic layer was washed with 50 mL of saturated saline and separated, and then washed with 50 mL of saturated saline and 5 mL of an aqueous solution of 7.5% by mass sodium bicarbonate to be separated. Thereafter, concentration was performed to obtain an oily composition, which was then purified by column chromatography, and thereby a compound (I-14) (yield 75%) was obtained.

$^1$H-NMR (400 MHz, CDCl$_3$): δ (ppm) 1.25-1.35 (d, 6H), 2.65-2.75 (m, 8H), 4.10-4.20 (m, 2H), 4.23 (t, 2H), 4.43 (d, 4H), 4.52 (d, 4H), 5.15-5.25 (m, 2H), 5.83 (m, 2H), 6.05-6.15 (m, 2H), 6.40 (d, 2H), 7.48 (s, 2H)

Synthesis Example 9

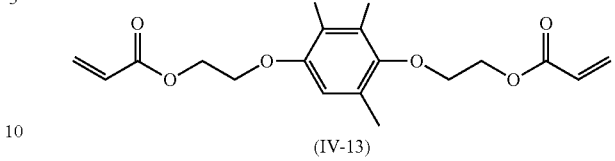

(IV-13)

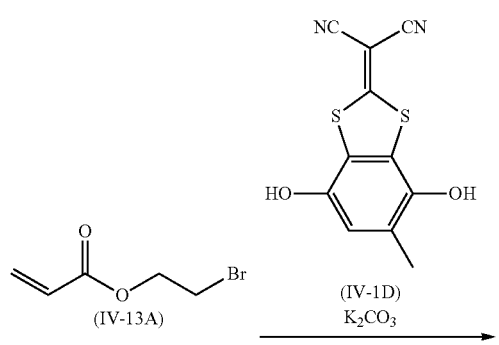

[Synthesis of Compound (IV-13)]

2.06 g (11.5 mmol) of 2-bromoethyl acrylate (IV-13A), 1.26 g (4.8 mmol) of the compound (IV-1D), 2.0 g (14.4 mmol) of potassium carbonate, 10 mg of 2,6-di-t-butyl-4-methylphenol, and 20 mL of THF were mixed, and the internal temperature was heated to 65° C. After stirring for 8 hours, the mixture was cooled to 25° C., 100 mL of ethyl acetate was added, the collected organic layer was washed with 1 N hydrochloric acid and saturated saline, and then dried over anhydrous sodium sulfate, the solvent was removed with a rotary evaporator, and purification was performed by silica gel chromatography, and thereby 1.58 g of a compound (IV-13) (yield 72%) was obtained.

$^1$H-NMR (400 MHz, CDCl$_3$): δ (ppm) 2.35 (s, 3H), 4.15 (m, 2H), 4.33 (m, 2H), 4.45-4.60 (m, 4H), 5.92 (dd, 2H), 6.18 (m, 2H), 6.48 (dd, 2H), 6.73 (s, 1H)

Synthesis Example 10

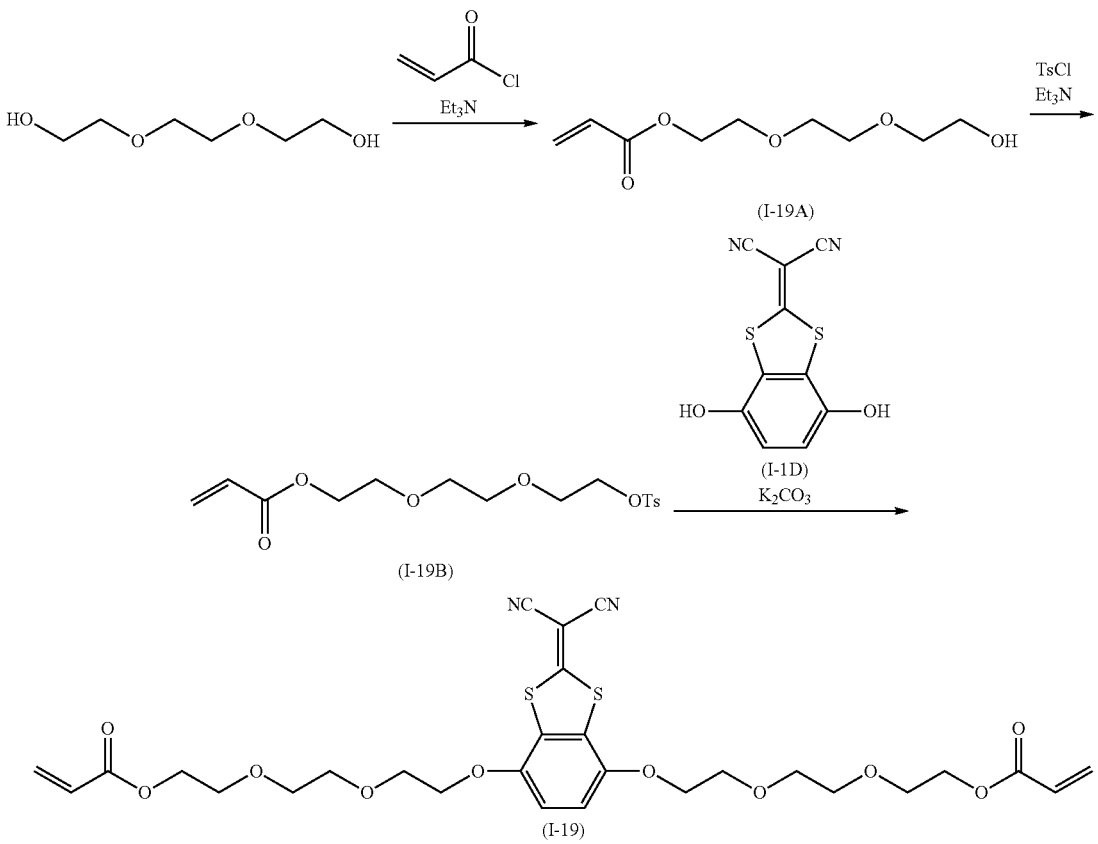

[Synthesis of Compound (I-19A)]

33.2 g (0.22 mol) of triethylene glycol, 490 mg of 2,6-di-t-butyl-4-methylphenol, 43 mL of N,N-dimethylacetamide, and 200 mL of THF were mixed, and the internal temperature was cooled to 0° C. 20 g (0.22 mol) of acryloyl chloride was added dropwise over 30 minutes, and thereafter, the internal temperature was set to 40° C. and the mixture was stirred for 3 hours. After filtering the precipitated salt, the solvent was removed with a rotary evaporator, purification was performed by silica gel chromatography, and thereby 20.3 g of a compound (I-19A) (yield 45%) was obtained.

[Synthesis of Compound (I-19B)]

5.0 g (24.5 mmol) of the compound (I-19A), 4.95 g (26.0 mmol) of p-toluenesulfonic acid chloride, 2.9 g (28.7 mmol) of triethylamine, 110 mg of 2,6-di-t-butyl-4-methylphenol, and 25 mL of ethyl acetate were mixed, and the internal temperature was heated to 50° C. After stirring for 5 hours, the mixture was cooled to 25° C., the collected organic layer was washed with 1 N hydrochloric acid and saturated saline, and then dried over anhydrous sodium sulfate, the solvent was removed with a rotary evaporator, and purification was performed by silica gel chromatography, and thereby 8.0 g of a compound (I-19B) (yield 91%) was obtained.

[Synthesis of Compound (I-19)]

7.0 g (19.5 mmol) of the compound (I-19B), 2.20 g (8.8 mmol) of the compound (I-1D), 9.55 g (29.3 mmol) of cesium carbonate, 50 mg of 2,6-di-t-butyl-4-methylphenol, and 50 mL of THF were mixed, and the internal temperature was heated to 70° C. After stirring for 5 hours, the mixture was cooled to 25° C., 100 mL of ethyl acetate was added, the collected organic layer was washed with 1 N hydrochloric acid and saturated saline, and then dried over anhydrous sodium sulfate, the solvent was removed with a rotary evaporator, and purification was performed by silica gel chromatography, and thereby 4.2 g of a compound (I-19) (yield 77%) was obtained.

$^1$H-NMR (solvent: DMSO-d6) δ (ppm): 3.55-3.65 (m, 8H), 3.65 (d, 4H), 3.76 (d, 4H), 4.20 (d, 4H), 4.26 (d, 4H), 5.93 (d, 2H), 6.10-6.20 (m, 2H), 6.32 (d, 2H), 7.21 (s, 2H)

Synthesis Example 11

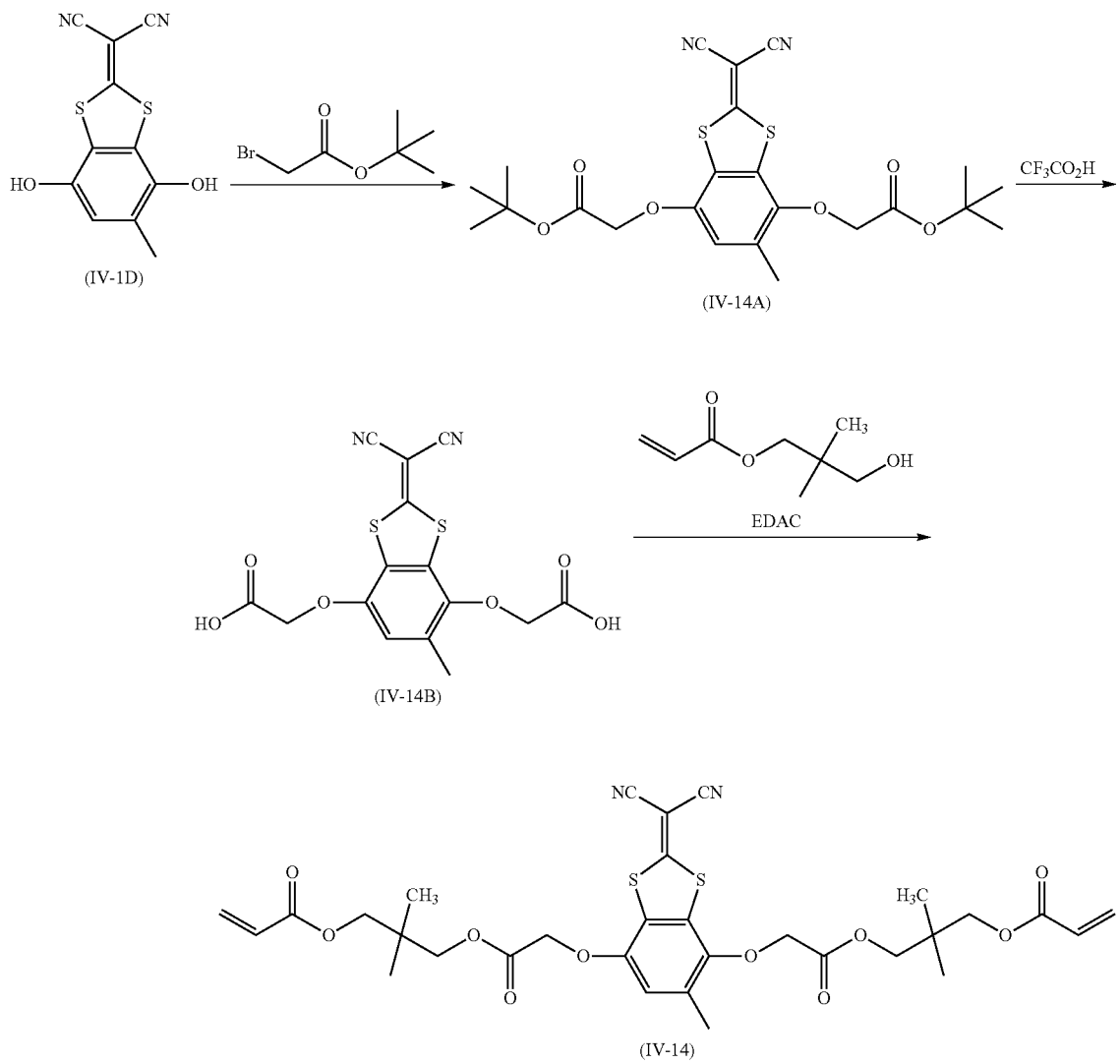

[Synthesis of Compound (IV-14A)]

55.8 g (285.9 mmol) of t-butyl bromoacetate, 30 g (114.4 mmol) of the compound (IV-1D), 111.8 g (343.1 mmol) of cesium carbonate, 3.7 g (11.4 mmol) of tetrabutylammonium, 300 mL of THF, and 150 mL of N,N-dimethylacetamide were mixed, and the internal temperature was heated to 75° C. After stirring for 5 hours, the mixture was cooled to 25° C., 750 ml of water was added, and the precipitated solid was filtered. By washing with water and methanol, a compound (IV-14A) was obtained (yield 92%).

[Synthesis of Compound (IV-14B)]

After mixing 50 g (102 mmol) of the t-butyl ester compound (IV-14A) and 500 mL of dichloromethane, 150 mL of trifluoroacetic acid was added and stirred at 25° C. for 2 hours. The internal temperature was cooled to 5° C., the precipitated crystals were filtered and washed with dichloromethane, and thereby a compound (IV-14B) (yield 98%) was obtained.

[Synthesis of Compound (IV-14)]

33.0 g (87.2 mmol) of the carboxylic acid compound (IV-14B), 500 mL of dichloromethane, 26.1 g (200.6 mmol) of hydroxypropyl acrylate, 1.1 g (8.7 mmol) of N,N-dimethylaminopyridine, and 38.3 g (200.6 mmol) of 1-ethyl-3-(3-dimethylaminopropyl) carbodiimide hydrochloride (abbreviation: EDAC) were mixed. After stirring at 40° C. for 2 hours, 300 mL of 1 N aqueous hydrochloric acid was added, washed and separated. An oily composition was obtained by performing dehydration and filtration with magnesium sulfate, and concentration, and thereafter, purification was performed by column chromatography. Thereby, a compound (IV-14) was obtained (yield 60%).

[1] H-NMR (400 MHz, CDCl$_3$): δ (ppm) 1.25-1.35 (d,6H), 2.36 (s,3H), 4.10-4.30 (m,2H), 4.30-4.45 (m,2H), 4.52 (d,2H), 4.72 (d,2H), 5.20-5.40 (m,2H), 5.83 (m,2H), 6.05-6.15 (m,2H), 6.40 (d,2H), 6.65 (d,1H)

<Synthesis Example 12>

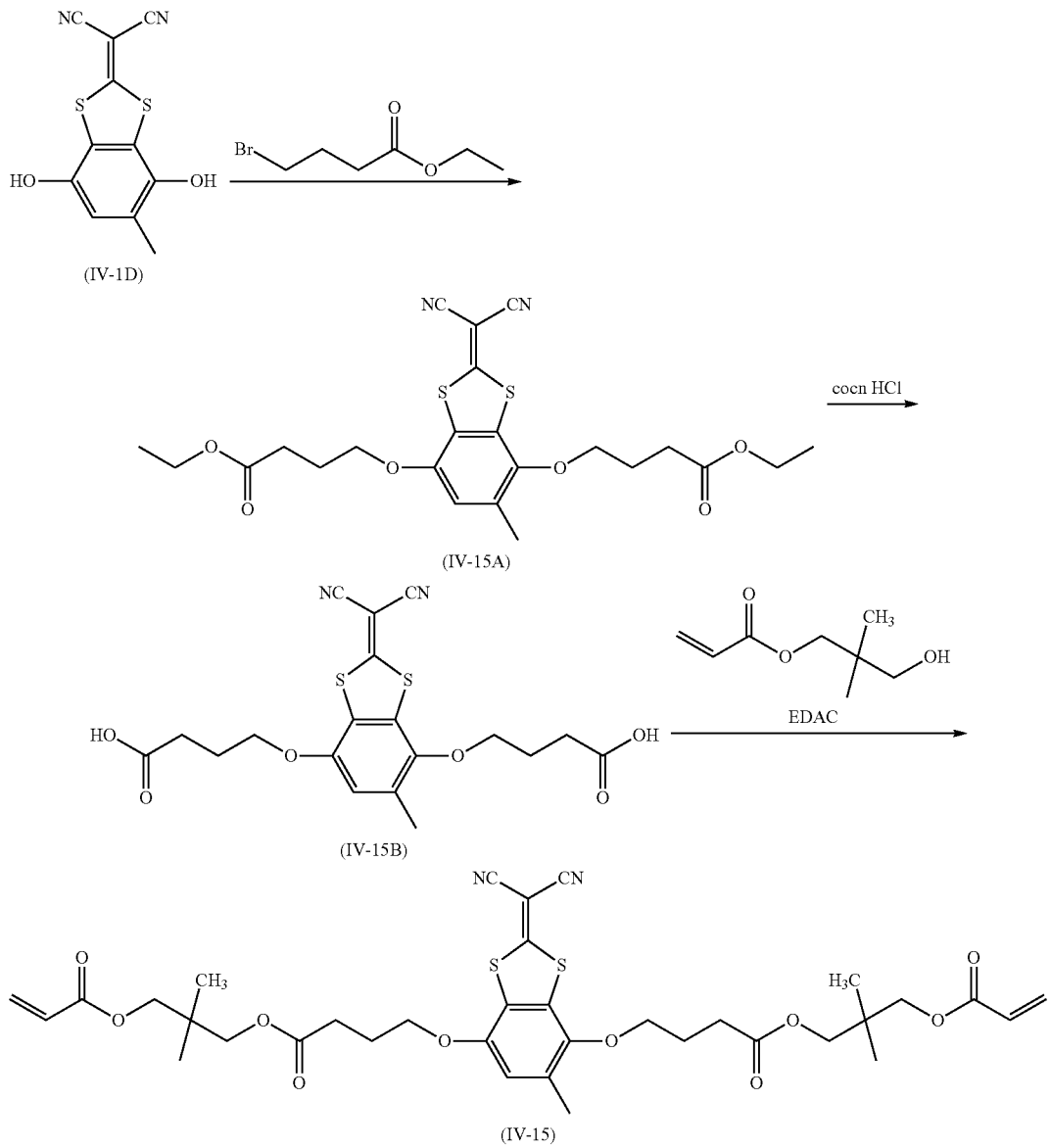

[Synthesis of Compound (IV-15A)]

A compound (IV-15A) (yield 75%) was obtained in the same manner except that t-butyl bromoacetate in the synthesis method of the compound (IV-14A) described in Synthesis Example 11 was changed to 4-bromoethyl acetate.

[Synthesis of Compound (IV-15B)]

2.5 g (102 mmol) of the ester compound (IV-15A), 5 mL of concentrated hydrochloric acid, and 25 mL of acetic acid were mixed and then stirred at 60° C. for 1 hour. Thereafter, 80 mL of water was added, and the precipitated solid was filtered. The obtained solid was purified by column chromatography, and thereby a compound (IV-15B) (yield 80%) was obtained.

[Synthesis of Compound (IV-15)]

A compound (IV-15) (yield 55%) was obtained in the same manner except that the compound (IV-14B) in the synthesis method of the compound (IV-14) described in Synthesis Example 11 was changed to the compound (IV-15B).

$^1$ H-NMR (400 MHz, CDCl$_3$): δ (ppm) 1.20-1.35 (m,6H), 2.10-2.20 (m,4H), 2.32 (s,3H), 2.60-2.75 (m,4H), 3.91 (t,2H), 4.10-4.30 (m,6H), 5.24 (sext,2H), 5.84 (d,2H), 6.05-6.15 (m,2H), 6.40 (d,2H), 6.70 (s,1H)

<Preparation of lens adhesives (A-1) to (A-16)>

A component (A), a component (B), and a photoinitiator (IRGACURE 819) were mixed to make the composition shown in Table 1, the mixture was stirred to make it uniform, and thereby a lens adhesive was prepared.

For the component (A) of each lens adhesive, a light absorption spectrum of a solution diluted with tetrahydrofuran (THF) was measured using UV-2550 manufactured by Shimadzu Corporation, and it was confirmed that a wavelength (nm) shown in Table 1 had a maximum value (λmax).

In addition, a refractive index of a cured material of each of the lens adhesives was obtained by the following procedure. An adhesive composition was injected into a transparent glass mold having a diameter of 10 mm and a thickness of 1 mm and irradiated with ultraviolet rays of 15 mW/cm$^2$ for 20 seconds using an Execure 3000 (manufactured by Hoya Corporation) to obtain a cured material. The obtained cured material was taken out of the transparent glass mold, and a refractive index at a wavelength of 587 nm was measured using an Abbe meter (manufactured by ATAGO CO., LTD.).

TABLE 1

| Adhesive | | A1 | A2 | A3 | A4 | A5 | A6 | A7 | A8 |
|---|---|---|---|---|---|---|---|---|---|
| Component (A) | V-3 | 70 | | | | | | | |
| | VI-1 | | 70 | | | | | | |
| | I-4 | | | 70 | | | | | |
| | III-3 | | | | 70 | | | | |
| | IV-1 | | | | | 60 | | | |
| | I-7 | | | | | | 70 | | |
| | I-14 | | | | | | | 70 | |
| | IV-13 | | | | | | | | 25 |
| | I-9 | | | | | | | | |
| | IV-14 | | | | | | | | |
| | IV-15 | | | | | | | | |
| Component (B) | Monomer 3 | 29 | 29 | 29 | 29 | 39 | 29 | 29 | 50 |
| | Monomer 4 | | | | | | | | 24 |
| | Monomer 7 | | | | | | | | |
| Component (C) | SHIKOH UV-3000B | | | | | | | | |
| | KURARAY LIQUID RUBBER UC-203M | | | | | | | | |
| Photoinitiator | Irgacure819 | 1 | 1 | 1 | 1 | 1 | 1 | 1 | 1 |
| | Total | 100 | 100 | 100 | 100 | 100 | 100 | 100 | 100 |
| | λmax (nm) of component (A) | 368 | 346 | 365 | 362 | 369 | 367 | 364 | 373 |
| | Refractive index of cured material | 1.582 | 1.573 | 1.556 | 1.555 | 1.551 | 1.561 | 1.548 | 1.560 |
| Adhesive | | A9 | A10 | A11 | A12 | A13 | A14 | A15 | A16 |
| Component (A) | V-3 | | | | | | | | |
| | VI-1 | | | | | | | | |
| | I-4 | | | | | | | | |
| | III-3 | | | | | | | | |
| | IV-1 | | 85 | 18 | 13 | | | | |
| | I-7 | | | | | | | | |
| | I-14 | | | | | | | | |
| | IV-13 | | | | | | | | |
| | I-9 | 50 | | | | | | | |
| | IV-14 | | | | | 40 | | | |
| | IV-15 | | | | | | 40 | 40 | 40 |
| Component (B) | Monomer 3 | 49 | 14 | 50 | 50 | 20 | 20 | | |
| | Monomer 4 | | | 31 | 36 | | | | |
| | Monomer 7 | | | | | 39 | 39 | 39 | 39 |

TABLE 1-continued

| Component (C) | SHIKOH UV-3000B | | | | | | | 20 | |
|---|---|---|---|---|---|---|---|---|---|
| | KURARAY LIQUID RUBBER UC-203M | | | | | | | | 20 |
| Photoinitiator | Irgacure819 | 1 | 1 | 1 | 1 | 1 | 1 | 1 | 1 |
| | Total | 100 | 100 | 100 | 100 | 100 | 100 | 100 | 100 |
| | λmax (nm) of component (A) | 371 | 369 | 369 | 369 | 373 | 374 | 374 | 374 |
| | Refractive index of cured material | 1.545 | 1.576 | 1.512 | 1.507 | 1.553 | 1.551 | 1.549 | 1.550 |

Numerical values in the table are % by mass

In production of the following cemented lenses, an adhesive (H19) having the composition shown in Table 2 and described in JP2012-523485A was used as an adhesive of the comparative examples.

TABLE 2

| | H19 |
|---|---|
| Irgacure819 | 0.22 |
| Brominated aromatic urethane acrylate (CN2600) | 22.41 |
| Tribromophenyl acrylate (BR30) | 15.33 |
| 9,9-bis{4-(2-acryloyloxyethoxy)phenyl}fluorene (NK-BPEF) | 15.33 |
| Vinyl resin (NTT #6205) | 31.44 |
| Acrylic oligomer (CN 131B) | 5.26 |
| Pentaerythritol tetrakis(3-mercaptopropionate) | 3 |

Numerical values in the table are parts by mass

<Production of Cemented Lens>

In a work box purged with nitrogen, a lens adhesive was applied to one surface of a horizontally installed lens B. Next, a lens A was superimposed on the applied adhesive, and was spread out so that air bubbles did not enter. At this time, an application amount was adjusted so that a film thickness of the lens adhesive layer at the center part became 30 m. Next, irradiation with ultraviolet rays of 300 mJ/cm$^2$ was performed from the side of the lens A using Execure 3000 (manufactured by HOYA CORPORATION) to cure the lens adhesive. Thereby, cemented lenses R1 to R39 shown in Table 4 were obtained.

As the lens A, BK7 (a glass lens, manufactured by OHARA INC.) was used. As the lens B, any of the following lenses was used.

BK7 (a glass lens, manufactured by OHARA INC.)
OKP4 (a resin lens, manufactured by Osaka Gas Chemicals Co., Ltd.)
H1 to H4 (a compound lens, produced by the following procedure)

In a case where the compound lenses H1 to H4 were used as the lens B, a surface on a resin layer side was used as a cemented surface.

(Production of compound lenses H1 to H4)

The lenses were produced as described below with reference to the description in WO2017/115649A. As a curable composition, compositions F1 to F4 having compositional ratios shown in Table 3 were respectively used for H1 to H4. 200 mg of the curable composition was injected into a molding mold whose surface was treated with chromium nitride, the entire surface of the curable composition that was not in contact with the molding mold was covered with a transparent glass lens (glass material=BK7, convex lens with a diameter of 33 mm, a center thickness of 3 mm, a radius of curvature of the surface in contact with the curable composition=44.3 mm, a radius of curvature of the surface not in contact with the curable composition=330.9 mm), and the curable composition was spread to have a diameter of 30 mm. After obtaining this state, irradiation with ultraviolet rays of 300 mJ/cm$^2$ was performed from above the glass lens using Execure 3000 (manufactured by HOYA CORPORATION). Next, while maintaining the state sandwiched between the molding mold and the glass lens, the temperature was raised to 200° C. while applying a pressure of 0.196 MPa (2 kgf/cm$^2$) to the curable composition. Thereafter, the cured material of the curable composition and the molding mold were separated at a speed of 0.05 mm/sec to produce a compound lens.

TABLE 3

| | Curable composition F1 | Curable composition F2 | Curable composition F3 | Curable composition F4 |
|---|---|---|---|---|
| M-1 | 70.9 | | | |
| M-2 | | 70.9 | | |
| M-3 | | | 70.9 | |
| M-4 | | | | 70.9 |
| 2-Phenoxyethyl acrylate | 22.7 | 22.7 | 22.7 | 22.7 |
| β-Caryophyllene | 4.5 | 4.5 | 4.5 | 4.5 |
| Irgacure819 | 0.1 | 0.1 | 0.1 | 0.1 |
| Perbutyl O | 1.0 | 1.0 | 1 | 1 |
| Percumyl H-80 | 0.7 | 0.7 | 0.7 | 0.7 |
| JP-506H | 0.1 | 0.1 | 0.1 | 0.1 |
| Abbe number of cured material | 22.7 | 20.5 | 20.9 | 23.2 |

TABLE 3-continued

| Curable composition F1 | Curable composition F2 | Curable composition F3 | Curable composition F4 |
|---|---|---|---|

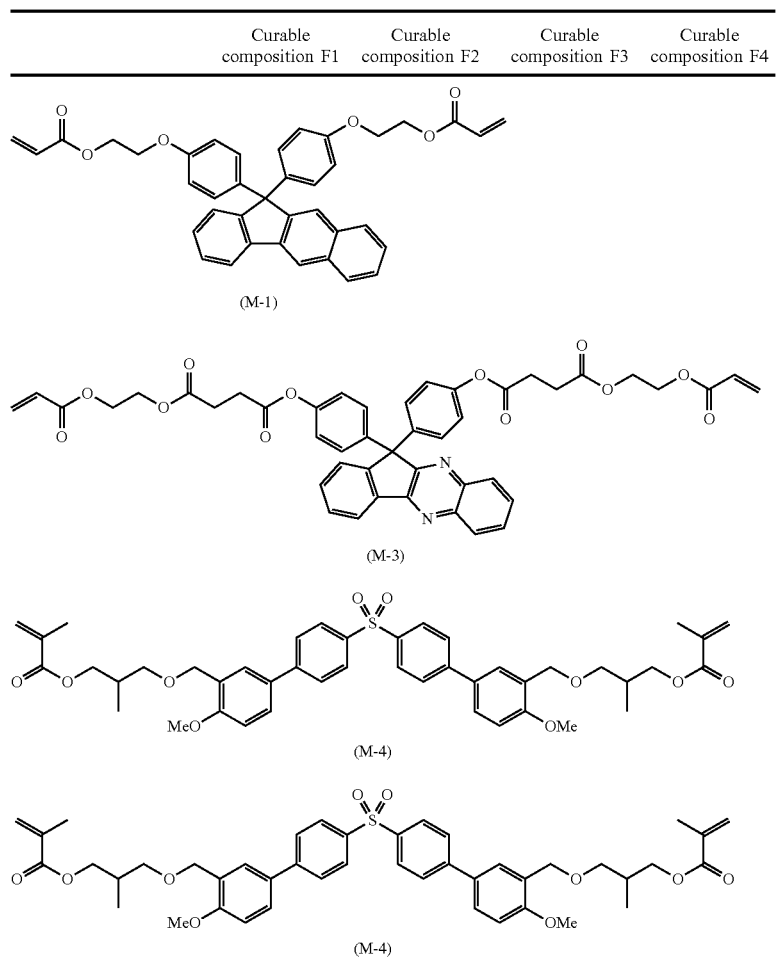

(M-1)

(M-3)

(M-4)

(M-4)

Abbe numbers of each of the cured materials of the curable compositions F1 to F4 shown in Table 3 were determined as follows. A curable composition was injected into a transparent glass mold having a diameter of 10 mm and a thickness of 1 mm and irradiated with ultraviolet rays of 15 mW/cm$^2$ for 20 seconds using an Execure 3000 (manufactured by Hoya Corporation) to obtain a semi-cured material. Subsequently, the obtained semi-cured material was taken out of the transparent glass mold and heated at 200° C. for 5 minutes using a hot plate to obtain a cured material. An Abbe number of the obtained cured material was measured using an Abbe meter (manufactured by ATAGO CO., LTD.).

TABLE 4

| | Lens A | Lens B | Adhesive |
|---|---|---|---|
| R1 | BK7 | BK7 | A1 |
| R2 | BK7 | BK7 | A2 |
| R3 | BK7 | BK7 | A3 |
| R4 | BK7 | BK7 | A4 |
| R5 | BK7 | BK7 | A5 |
| R6 | BK7 | BK7 | A6 |
| R7 | BK7 | BK7 | A7 |
| R8 | BK7 | BK7 | A8 |
| R9 | BK7 | BK7 | A9 |
| R10 | BK7 | BK7 | A10 |
| R11 | BK7 | BK7 | A11 |

TABLE 4-continued

| | Lens A | Lens B | Adhesive |
|---|---|---|---|
| R12 | BK7 | BK7 | A12 |
| R13 | BK7 | BK7 | H19 |
| R14 | BK7 | OKP4 | A1 |
| R15 | BK7 | OKP4 | A2 |
| R16 | BK7 | OKP4 | A3 |
| R17 | BK7 | OKP4 | A5 |
| R18 | BK7 | OKP4 | H19 |
| R19 | BK7 | H1 | A1 |
| R20 | BK7 | H1 | A2 |
| R21 | BK7 | HI | A3 |
| R22 | BK7 | HI | A5 |
| R23 | BK7 | HI | H19 |
| R24 | BK7 | H3 | A1 |
| R25 | BK7 | H3 | A2 |
| R26 | BK7 | H3 | A3 |
| R27 | BK7 | H3 | A4 |
| R28 | BK7 | H3 | A5 |
| R29 | BK7 | H3 | A6 |
| R30 | BK7 | H3 | A7 |
| R31 | BK7 | H3 | A8 |
| R32 | BK7 | H3 | A9 |
| R33 | BK7 | H3 | H19 |
| R34 | BK7 | H2 | A3 |
| R35 | BK7 | H2 | A5 |
| R36 | BK7 | H2 | H19 |
| R37 | BK7 | H4 | A3 |
| R38 | BK7 | H4 | A5 |
| R39 | BK7 | H4 | H19 |

TABLE 4-continued

|  | Lens A | Lens B | Adhesive |
|---|---|---|---|
| R40 | BK7 | BK7 | A13 |
| R41 | BK7 | BK7 | A14 |
| R42 | BK7 | BK7 | A15 |
| R43 | BK7 | BK7 | A16 |
| R44 | BK7 | H3 | A13 |
| R45 | BK7 | H3 | A14 |
| R46 | BK7 | H3 | A15 |
| R47 | BK7 | H3 | A16 |

<Non-Defective Rate, Heat Shock Resistance Test, and Moisture-Heat Resistance Test in Examples 1 to 20, Examples 46 to 49, and Comparative Examples 1 to 3>

100 samples of cemented lenses R1 to R23 and R40 to R43 were produced. A visual evaluation was performed, and an appearance inspection of the obtained lenses was performed using a microscope, and lenses in which no bubbles were observed at a cemented surface were determined to be non-defective products. A percentage of non-defective products was evaluated as a non-defective rate, and evaluation was performed according to the following standards.

A: A non-defective rate was 80% or more.
B: A non-defective rate was 70% or more and less than 80%.
C: A non-defective rate was less than 70%.

In addition, a heat shock resistance test and a moisture-heat resistance test were performed on the cemented lenses determined to be non-defective products in the above test by the following methods. In the heat shock resistance test, ten samples of each of the cemented lenses were heated at 100° C. for 48 hours, and then the temperature was returned to room temperature, and the samples were further cooled to −40° C., allowed to elapse for 48 hours, and then the temperature was returned to room temperature. In the moisture-heat resistance test, ten samples of each of the cemented lenses were stored for 48 hours in an environment of 50° C. and 85% humidity, and then the temperature was returned to room temperature. For each of the cemented lenses that were subjected to the heat shock resistance test and the moisture-heat resistance test, a visual evaluation was performed, and an appearance inspection for cracks and peeling was performed using a microscope, and lenses that did not change before and after the test were determined as non-defective products. A percentage of non-defective products was evaluated as a non-defective rate, and evaluation was performed according to the following standards.

A: A non-defective rate was 90% or more.
B: A non-defective rate was 80% or more and less than 90%.
C: A non-defective rate was 70% or more and less than 80%.
D: A non-defective rate was less than 70%.

TABLE 5

|  | Example 1 | Example 2 | Example 3 | Example 4 | Example 5 | Example 6 | Example 7 | Example 8 |
|---|---|---|---|---|---|---|---|---|
| Lens | R1 | R2 | R3 | R4 | R5 | R6 | R7 | R8 |
| Non-defective rate | A | A | A | A | A | A | A | A |
| Heat shock resistance | C | B | B | B | B | B | B | B |
| Moisture-heat resistance | B | C | B | B | B | C | B | A |

|  | Example 9 | Example 10 | Example 11 | Example 12 | Example 46 | Example 47 | Example 48 | Example 49 | Comparative Example 1 |
|---|---|---|---|---|---|---|---|---|---|
| Lens | R9 | R10 | R11 | R12 | R40 | R41 | R42 | R43 | R13 |
| Non-defective rate | A | B | A | A | A | A | A | A | C |
| Heat shock resistance | B | B | B | B | B | B | A | A | D |
| Moisture-heat resistance | A | C | B | B | A | A | A | A | D |

|  | Example 13 | Example 14 | Example 15 | Example 16 | Comparative Example 2 |
|---|---|---|---|---|---|
| Lens | R14 | R15 | R16 | R17 | R18 |
| Non-defective rate | A | A | A | A | B |
| Heat shock resistance | B | B | A | A | D |
| Moisture-heat resistance | B | C | B | B | D |

|  | Example 17 | Example 18 | Example 19 | Example 20 | Comparative Example 3 |
|---|---|---|---|---|---|
| Lens | R19 | R20 | R21 | R22 | R23 |
| Non-defective rate | A | A | A | A | B |
| Heat shock resistance | B | A | A | A | D |
| Moisture-heat resistance | B | C | B | B | D |

Based on the results shown in Table 5, the cemented lens produced using the adhesive of the embodiment of the present invention showed high heat shock resistance as compared to the cemented lens produced using the adhesive for comparison, even in a case where any of a glass lens, a resin lens, or a compound lens was used as the lens B.

<Evaluation of Light Fastness of Cemented Lenses of Examples 21 to 33, Examples 50 to 53, and Comparative Examples 4 to 6>

Light fastness of each of the cemented lenses R24 to R33 and R44 to R47 produced using the compound lens as the lens B was evaluated as follows.

The produced cemented lens was irradiated with ultraviolet rays of 75 J/cm² from the lens A side using Execure 3000 (manufactured by HOYA CORPORATION). Before and after ultraviolet irradiation, measurement of ultraviolet-visible transmittance was performed at the center part of the cemented lens (diameter: 5 mm), and a rate of change in transmittance at a wavelength of 420 nm was obtained and evaluated according to the following standards.

A: A rate of change was less than 10%.
B: A rate of change was 10% or more and less than 20%.
C: A rate of change was 20% or more and less than 30%.
D: A rate of change was 30% or more.

TABLE 6

|  | Example 21 | Example 22 | Example 23 | Example 24 | Example 25 | Example 26 | Example 27 |
|---|---|---|---|---|---|---|---|
| Lens | R24 | R25 | R26 | R27 | R28 | R29 | R30 |
| Evaluation | B | C | A | B | A | A | B |

|  | Example 28 | Example 29 | Example 50 | Example 51 | Example 52 | Example 53 | Comparative Example 4 |
|---|---|---|---|---|---|---|---|
| Lens | R31 | R32 | R44 | R45 | R46 | R47 | R33 |
| Evaluation | A | B | A | A | A | A | D |

|  | Example 30 | Example 31 | Comparative Example 5 | Example 32 | Example 33 | Comparative Example 6 |
|---|---|---|---|---|---|---|
| Lens | R34 | R35 | R36 | R37 | R38 | R39 |
| Evaluation | A | A | D | A | A | D |

<Evaluation of Light Fastness of Compound Lens Irradiated with Ultraviolet Rays Through Cemented Lens in Examples 34 to 45, Examples 54 to 57, and Comparative Example 7>

The cemented lens was superimposed to cover the entire surface of the compound lens H3, and the compound lens H3 was irradiated with ultraviolet rays of 75 J/cm² using Execure 3000 through the cemented lens. Before and after ultraviolet irradiation, measurement of ultraviolet-visible transmittance was performed at the center part of the compound lens H3 (diameter: 5 mm), and a rate of change in transmittance at a wavelength of 420 nm was obtained and evaluated according to the following standards. R1 to R13 and R40 to R43 were respectively used as the cemented lenses.

A: A rate of change was less than 10%.
B: A rate of change was 10% or more and less than 20%.
C: A rate of change was 20% or more and less than 30%.
D: A rate of change was 30% or more.

TABLE 7

|  | Example 34 | Example 35 | Example 36 | Example 37 | Example 38 | Example 39 | Example 40 | Example 41 | Example 42 |
|---|---|---|---|---|---|---|---|---|---|
| Lens | R1 | R2 | R3 | R4 | R5 | R6 | R7 | R8 | R9 |
| Evaluation | B | C | A | B | A | A | B | A | B |

|  | Example 43 | Example 44 | Example 45 | Example 54 | Example 55 | Example 56 | Example 57 | Comparative Example 7 |
|---|---|---|---|---|---|---|---|---|
| Lens | R10 | R11 | R12 | R40 | R41 | R42 | R43 | R13 |
| Evaluation | A | B | C | A | A | A | A | D |

It is found that, in Examples 44 and 45, an amount of the compound IV-1 (component (A)) added to the adhesive used for the cemented lens was smaller than that in Example 38, and light fastness of the compound lens H3 was reduced.

Explanation of References

1: adhesive layer
2: cemented lens
3: lens A
4: lens B
5: lens C
6: resin layer
7: object side
8: image-formed surface side
9: axis

What is claimed is:

1. A lens adhesive comprising:
a compound represented by General Formula 1, $$Pol_1\text{-}Sp_1\text{-}L_1\text{-}Ar\text{-}L_2\text{-}Sp_2\text{-}Pol_2 \quad \text{(General Formula 1)}$$

in General Formula 1, Ar is any of aromatic rings represented by General Formulas 2-1 to 2-4,

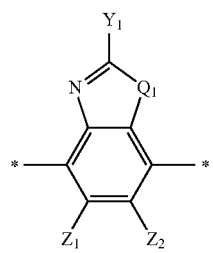

General Formula 2-1

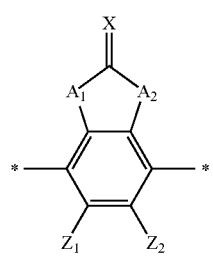

General Formula 2-2

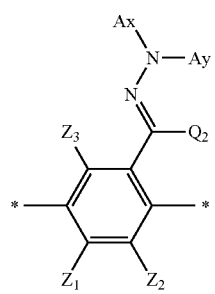

General Formula 2-3

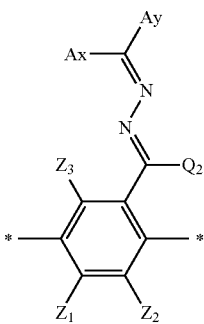

General Formula 2-4 in the formulas, $Q_1$ represents —S—, —O—, or $NR_{11}$—, where $R_{11}$ represents a hydrogen atom or an alkyl group having 1 to 6 carbon atoms, $Y_1$ represents an alkyl group which has 1 to 6 carbon atoms and may have a substituent, an aromatic hydrocarbon group which has 6 to 12 carbon atoms and may have a substituent, or an aromatic heterocyclic group which has 3 to 12 carbon atoms and may have a substituent, $Z_1$, $Z_2$, and $Z_3$ each independently represent a hydrogen atom, an aliphatic hydrocarbon group which has 1 to 20 carbon atoms and may have a substituent, an alkoxy group which has 1 to 20 carbon atoms and may have a substituent, an alicyclic hydrocarbon group which has 3 to 20 carbon atoms and may have a substituent, a monovalent aromatic hydrocarbon group which has 6 to 20 carbon atoms and may have a substituent, a halogen atom, a cyano group, a nitro group, —$NR_{12}R_{13}$, or $SR_{12}$, where $Z_1$ and $Z_2$ may be bonded to each other to form an aromatic hydrocarbon ring which may have a substituent or an aromatic heterocyclic ring which may have a substituent, and $R_{12}$ and $R_{13}$ each independently represent a hydrogen atom or an alkyl group having 1 to 6 carbon atoms, $A_1$ and $A_2$ each independently represent a group selected from the group consisting of —O—, —$NR_{21}$—, —S—, and CO—, where $R_{21}$ represents a hydrogen atom or a substituent, X represents O, S, C to which a hydrogen atom or a substituent is bonded, or N to which a hydrogen atom or a substituent is bonded, Ax represents an organic group which has 1 to 30 carbon atoms and has at least one aromatic ring selected from the group consisting of an aromatic hydrocarbon ring and an aromatic heterocyclic ring; and Ay represents a hydrogen atom, an alkyl group which has 1 to 6 carbon atoms and may have a substituent, or an organic group which has 1 to 30 carbon atoms and has at least one aromatic ring selected from the group consisting of an aromatic hydrocarbon ring and an aromatic heterocyclic ring, where the aromatic ring included in Ax and Ay may have a substituent, and Ax and Ay may be bonded to each other to form a ring which may have a substituent, $Q_2$ represents a hydrogen atom, or an alkyl group which has 1 to 6 carbon atoms and may have a substituent, $L_1$ and $L_2$ each independently represent a single bond, or a linking group selected from the group consisting of —O—, —S—, —C(=O)—, —OC(=O)—, —C(=O)O—, —OC(=O)O—, —$NR_{101}$C(=O)—, —C(=O)$NR_{102}$—, —OC(=O)$NR_{103}$—, —$NR_{104}$C(=O)O—, —SC(=O)—, and C(=O)S—, where $R_{101}$, $R_{102}$, $R_{103}$, and $R_{104}$ each independently represent -$Sp_3$-$Pol_3$ or a halogen atom, $Sp_1$ and $Sp_2$ each represent a single bond, or a linking group selected from the group consisting of a linear alkylene group which has 1 to 30 carbon atoms and may have a substituent, and a group in which one or two or more non-adjacent —$CH_2$—'s are substituted by —O—, —S—, —C(=O)—, —OC(=O)—, —C(=O)O—, —OC(=O)O—, —$NR_{201}$C(=O)—, —C(=O)$NR_{202}$—, —OC(=O)$NR_{203}$—, —$NR_{204}$C(=O)O—, —SC(=O)—, or —C(=O)S— in a linear alkylene group which has 2 to 30 carbon atoms and may have a substituent, where $R_{201}$, $R_{202}$, $R_{203}$, and $R_{204}$ each independently represent -$Sp_4$-$Pol_4$ or a halogen atom, $Sp_3$ and $Sp_4$ each independently represent a single bond or a divalent linking group, and $Pol_1$, $Pol_2$, $Pol_3$, and $Pol_4$ each independently represent a hydrogen atom or a polymerizable group, and wherein the compound represented by General Formula 1 has at least one polymerizable group.

2. The lens adhesive according to claim 1, wherein the lens adhesive includes a polymer having an ethylenically unsaturated group.

3. A method of producing a cemented lens comprising adhesion of two or more lenses using the lens adhesive according to claim 1.

4. The method according to claim 3, wherein Ar is an aromatic ring represented by General Formula 2-2.

5. The method according to claim 3, wherein any of $L_1$ or $L_2$ is —O—, —OC(=O)—, —OC(=O)O—, or O—C(=O)NH—.

6. The method to claim 3, wherein any of $L_1$ or $L_2$ is —O—; and any of $Sp_1$ or $Sp_2$ is a linking group selected from the group consisting of a linear alkylene group which has 1 to 30 carbon atoms and may have a substituent, and a group in which one or two or more non-adjacent —$CH_2$—'s are substituted by —O—, —S—, —C(=O)—, —OC(=O)—, —C(=O)O—, —OC(=O)O—, —$NR_{201}$C(=O)—, —C(=O)$NR_{202}$—, —OC(=O)$NR_{203}$—, —$NR_{204}$C(=O)O—, —SC(=O)—, or —C(=O)S— in a linear alkylene group which has 2 to 30 carbon atoms and may have a substituent and in which a terminal on an $L_1$ side or an $L_2$ side is —$CH_2$—.

\* \* \* \* \*